United States Patent [19]
Shefer

[11] Patent Number: 6,050,129
[45] Date of Patent: Apr. 18, 2000

[54] PROCESS FOR TESTING DIFFUSIVITY, ODOR CHARACTER AND ODOR INTENSITY OF A FRAGRANCE MATERIAL AND FRAGRANCE DIFFUSION EVALUATION APPARATUS FOR CARRYING OUT SUCH PROCESS

[75] Inventor: Shmuel David Shefer, East Brunswick, N.J.

[73] Assignee: International Flavors & Fragrances Inc., New York, N.Y.

[21] Appl. No.: 08/961,561

[22] Filed: Oct. 30, 1997

[51] Int. Cl.[7] .................................................. G01N 31/00

[52] U.S. Cl. ........................................ 73/23.34; 73/31.07

[58] Field of Search ................................ 73/23.34, 31.07, 73/19.01, 19.12

[56] References Cited

U.S. PATENT DOCUMENTS

| | | | |
|---|---|---|---|
| 4,770,027 | 9/1988 | Ehara et al. | 73/23.34 |
| 4,884,435 | 12/1989 | Ehara | 73/23.34 |
| 5,369,978 | 12/1994 | Mookherjee et al. | 73/23.34 |

*Primary Examiner*—Hezron Williams
*Assistant Examiner*—Michael Cygan
*Attorney, Agent, or Firm*—Arthur L. Liberman

[57] ABSTRACT

Described is a fragrance diffusion evaluation apparatus for testing the diffusivity, odor character and odor intensity of a fragrance material and a process for using same. The apparatus includes one or two hollow cylinders, each having a test sample suspended therein, devices for passing air through the inside of each of the cylinders and exit ports in each of the cylinders for the air flow where the intensity and aroma character are measured as a function of time and as a function of temperature. The sample is weighed initially and at time intervals, while the air is flowing through each of the cylinders at a fixed or variable rate.

19 Claims, 44 Drawing Sheets

FIG.1-A
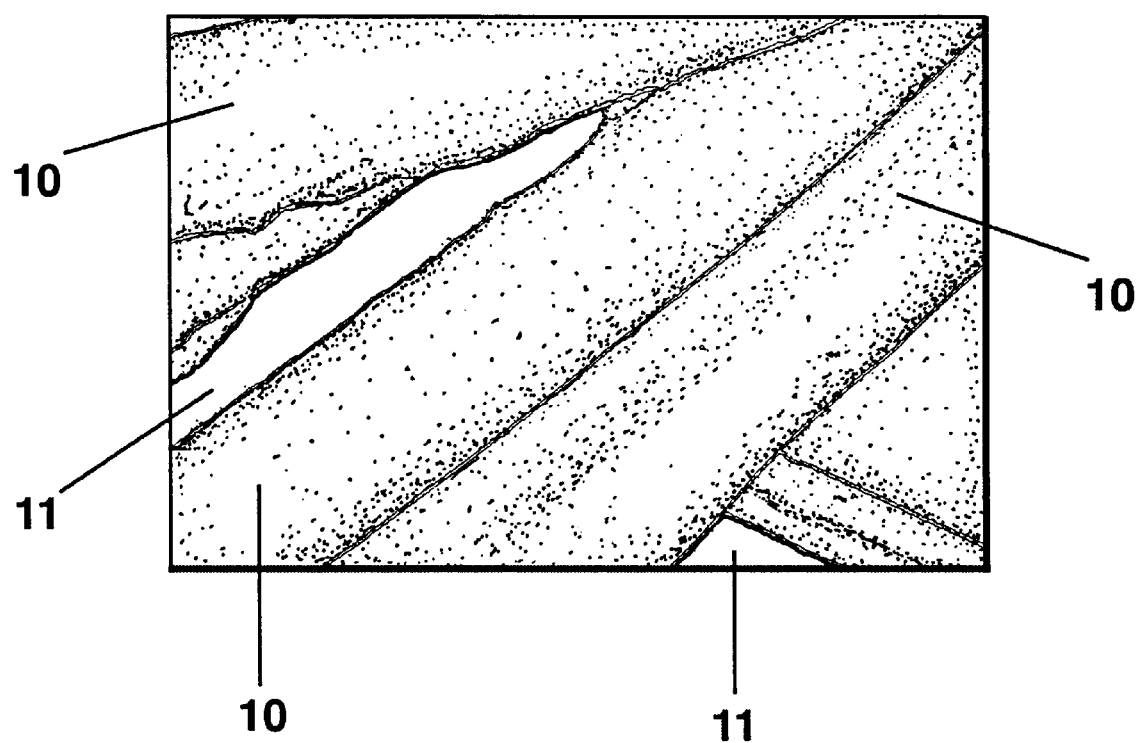

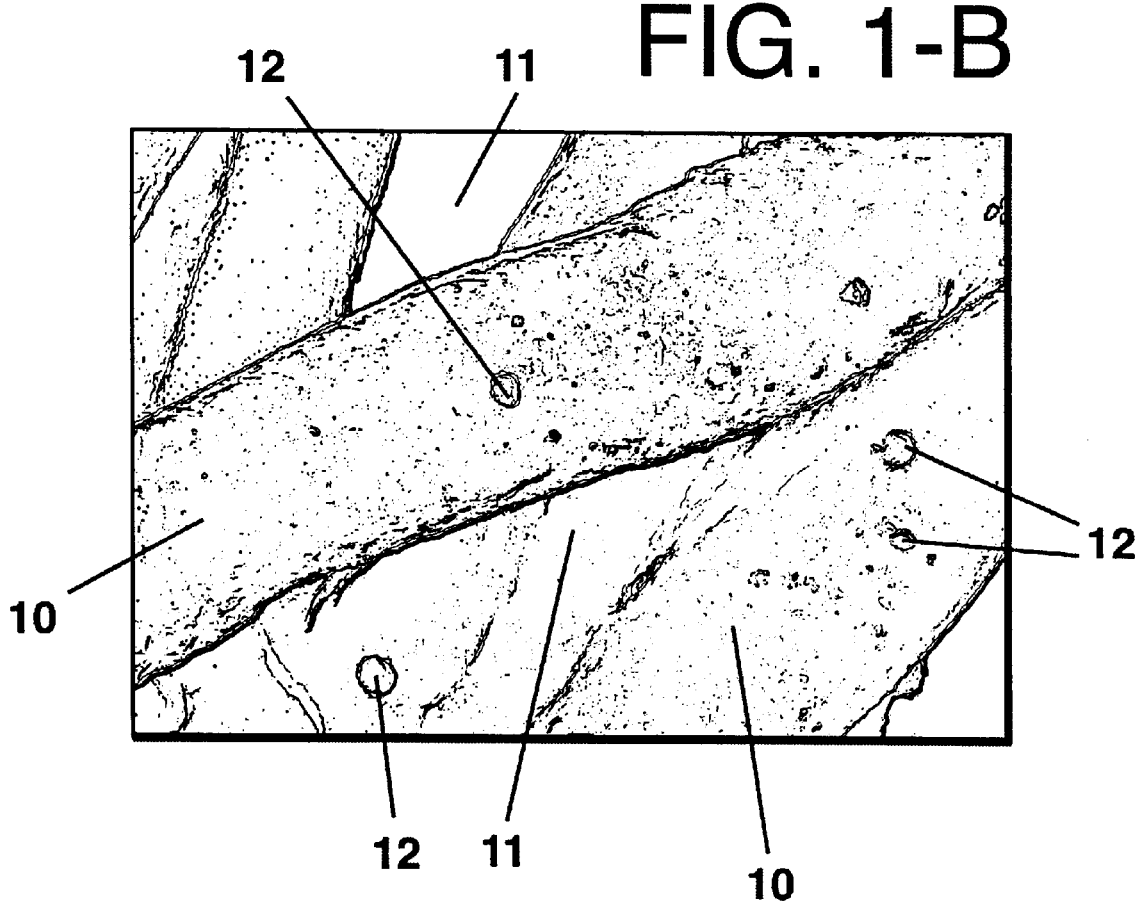
FIG. 1-B

FIG.2-A
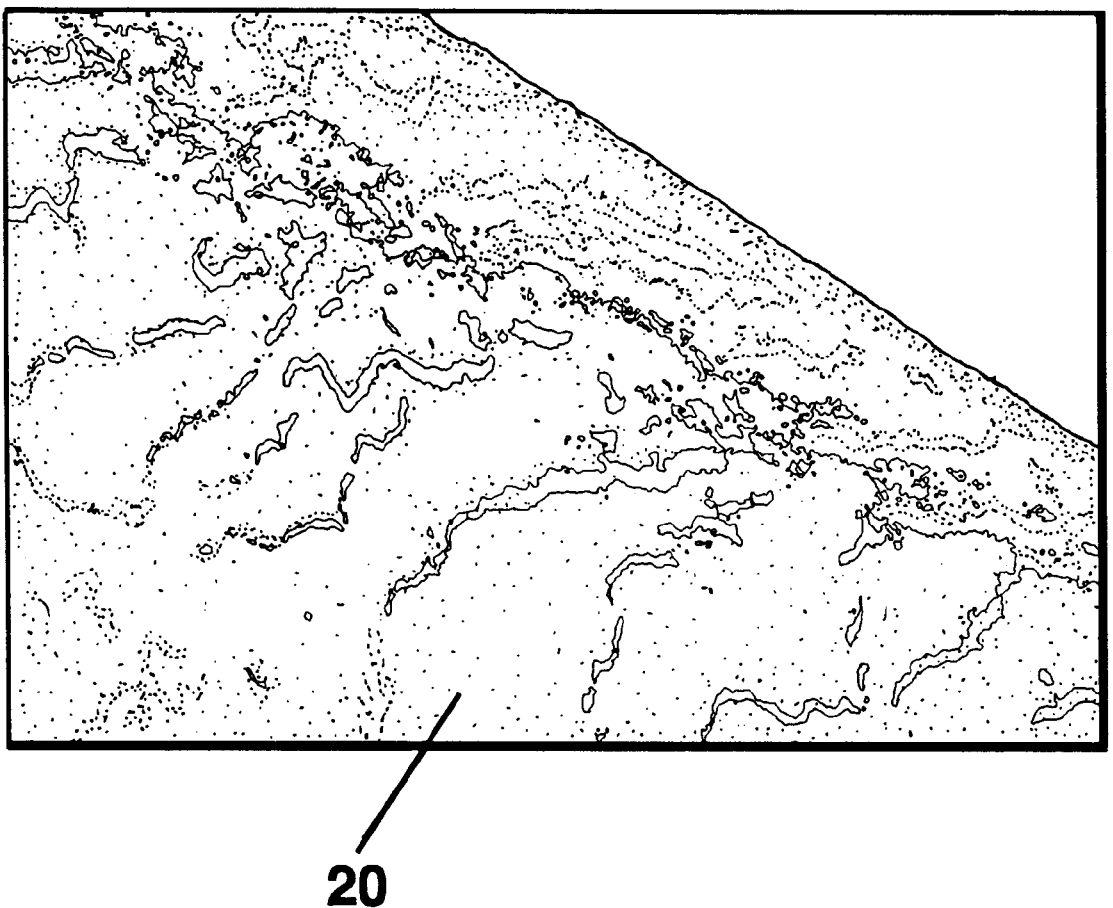
20

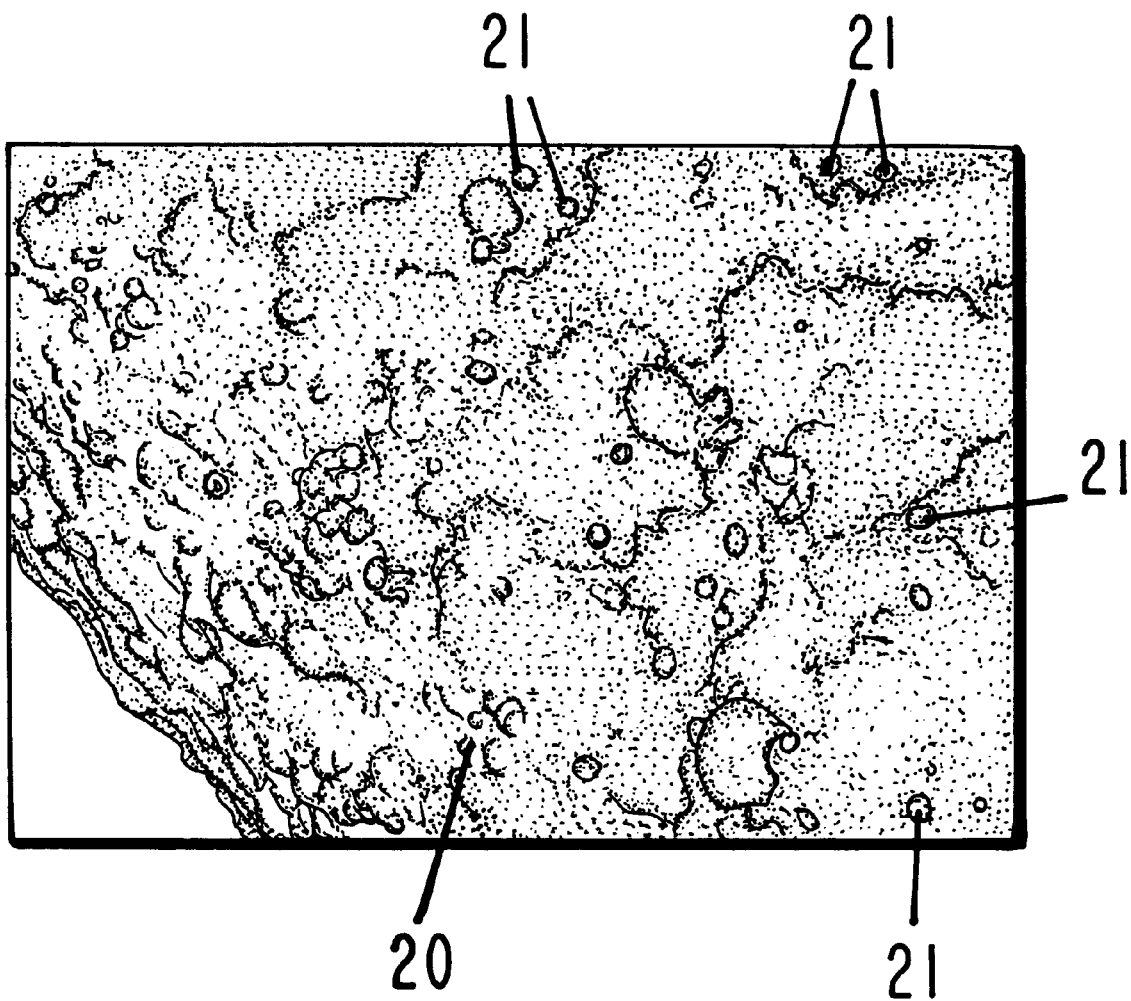
FIG.2-B

FIG.2-C
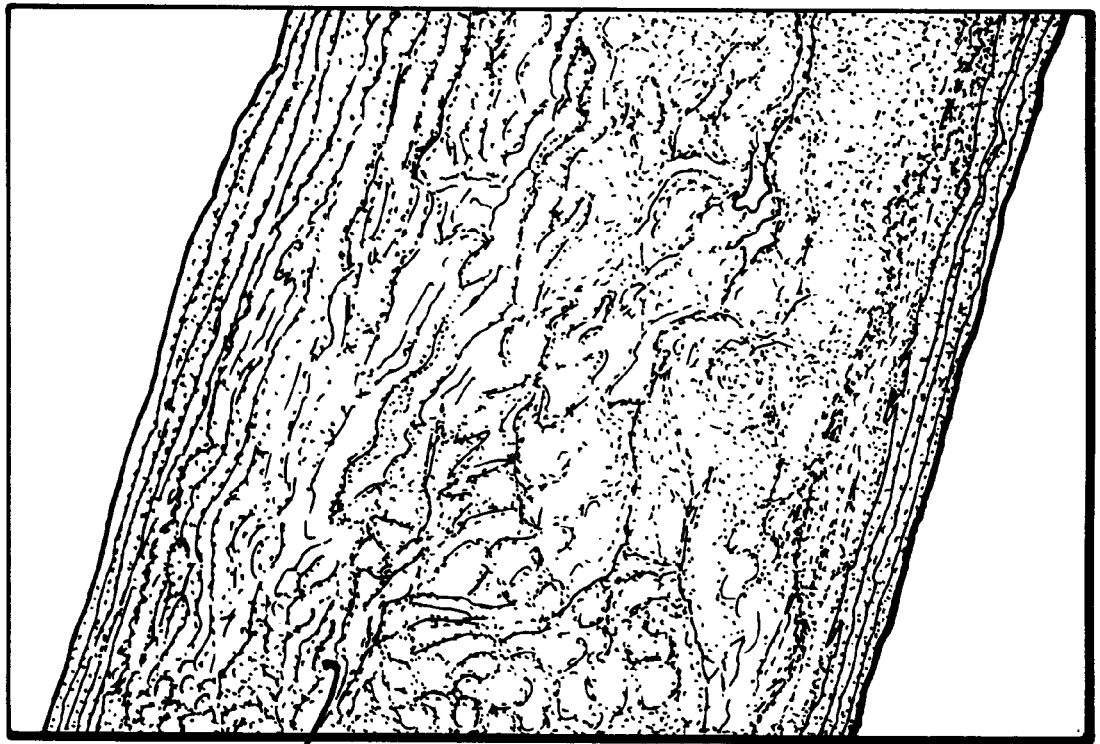
23

FIG.2-D
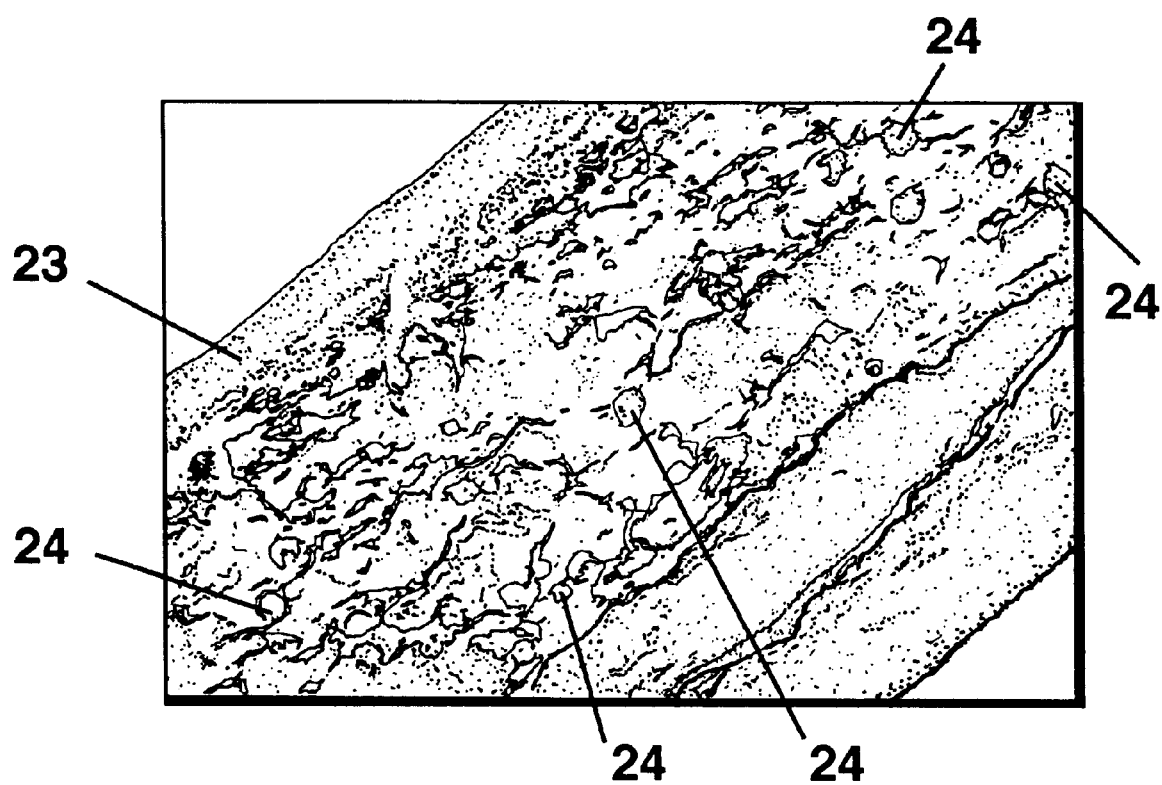

FIG.3-A
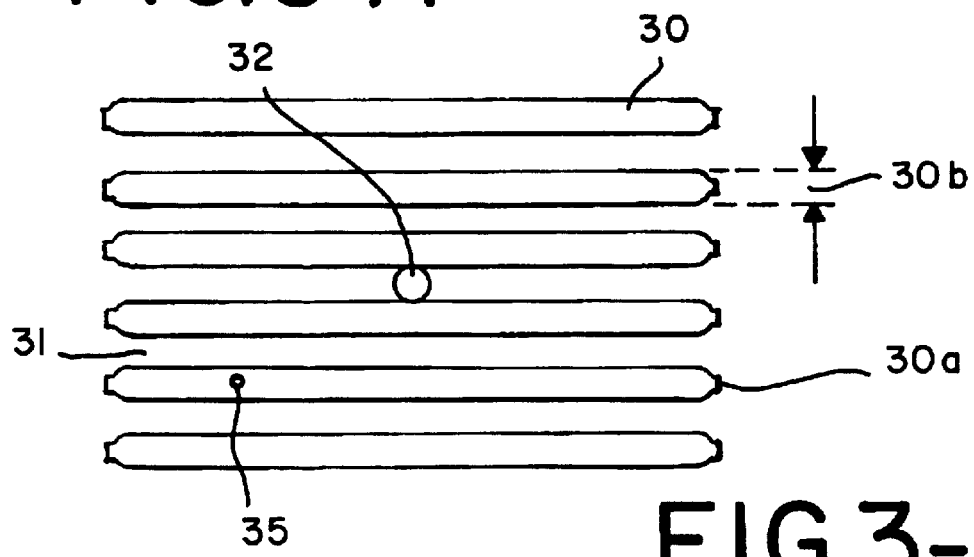
FIG.3-B
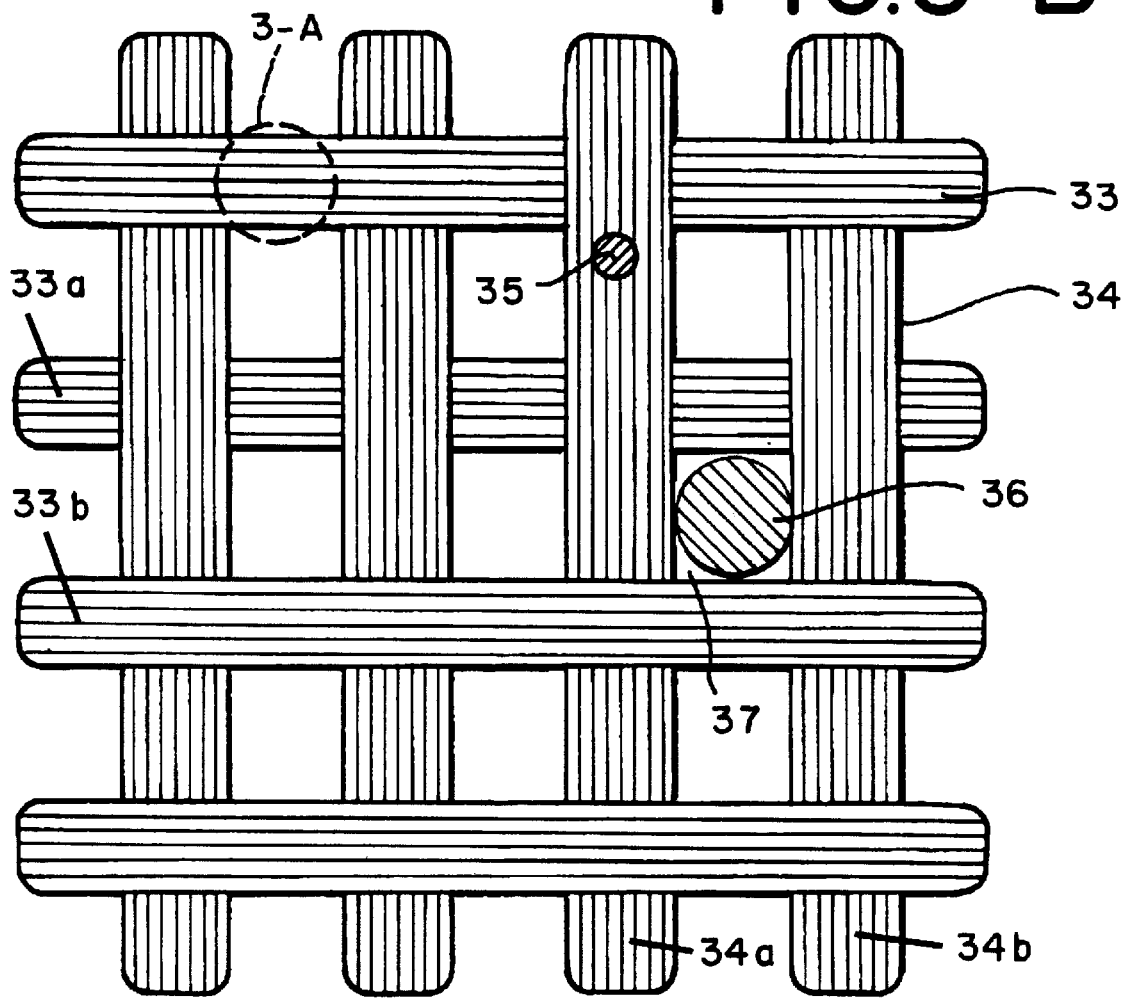

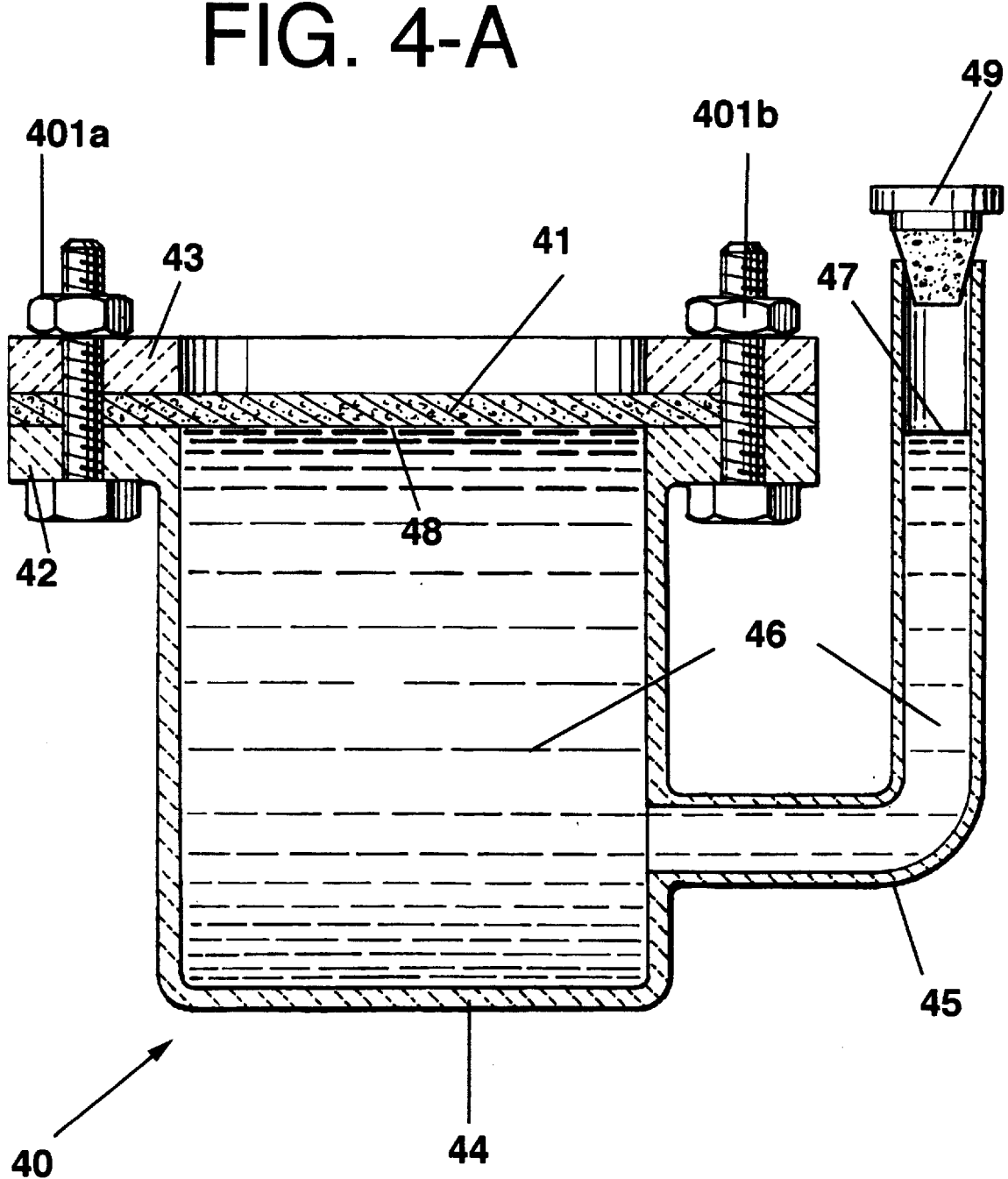
FIG. 4-A

FIG.4-B
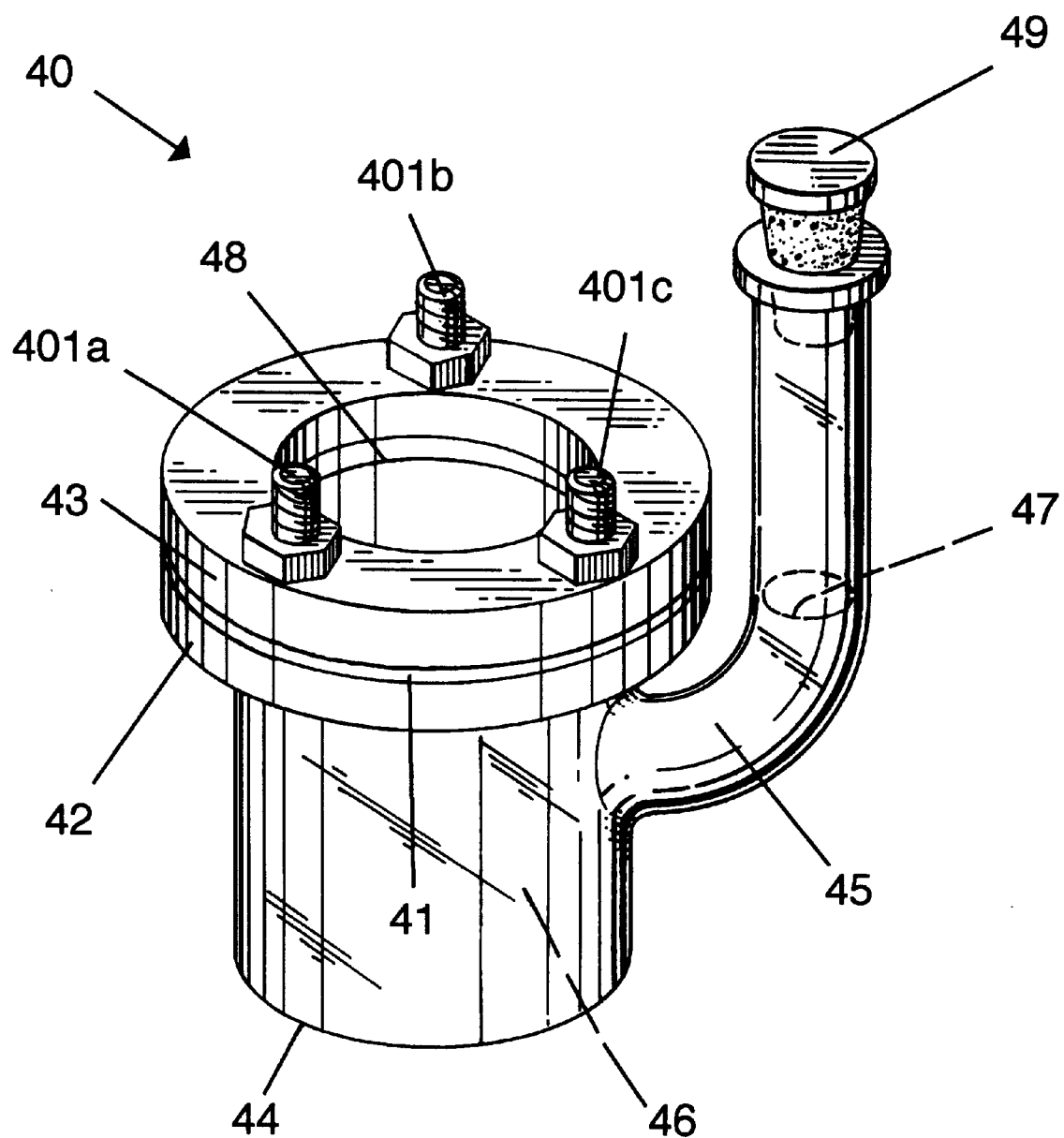

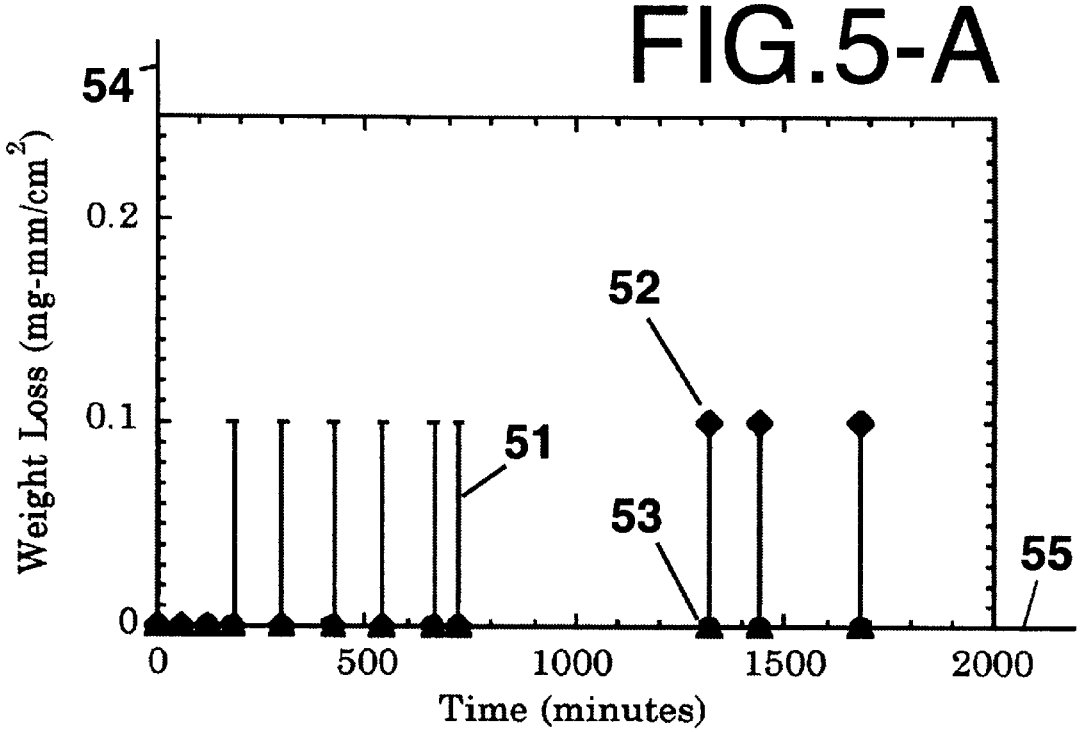
FIG.5-A
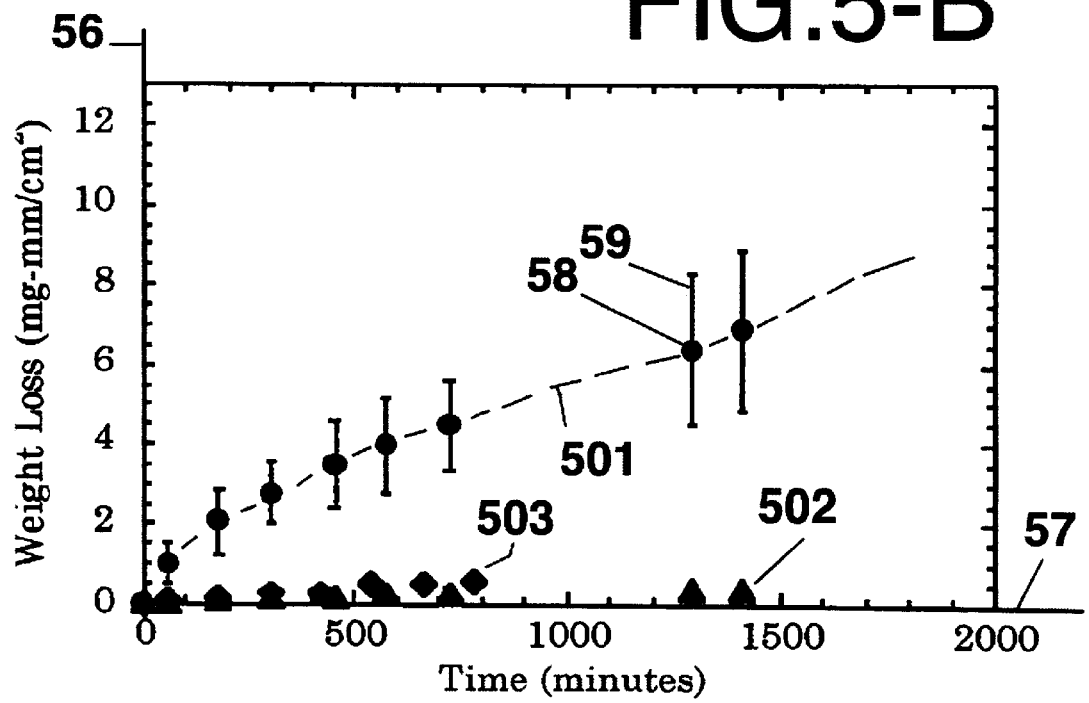
FIG.5-B

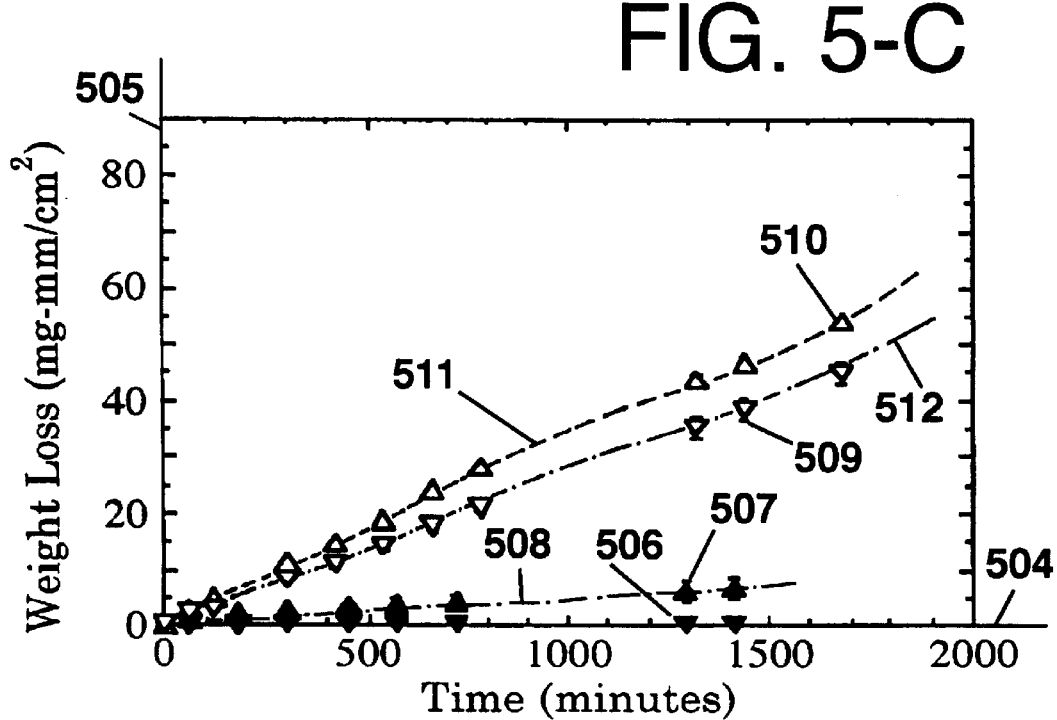
FIG. 5-C
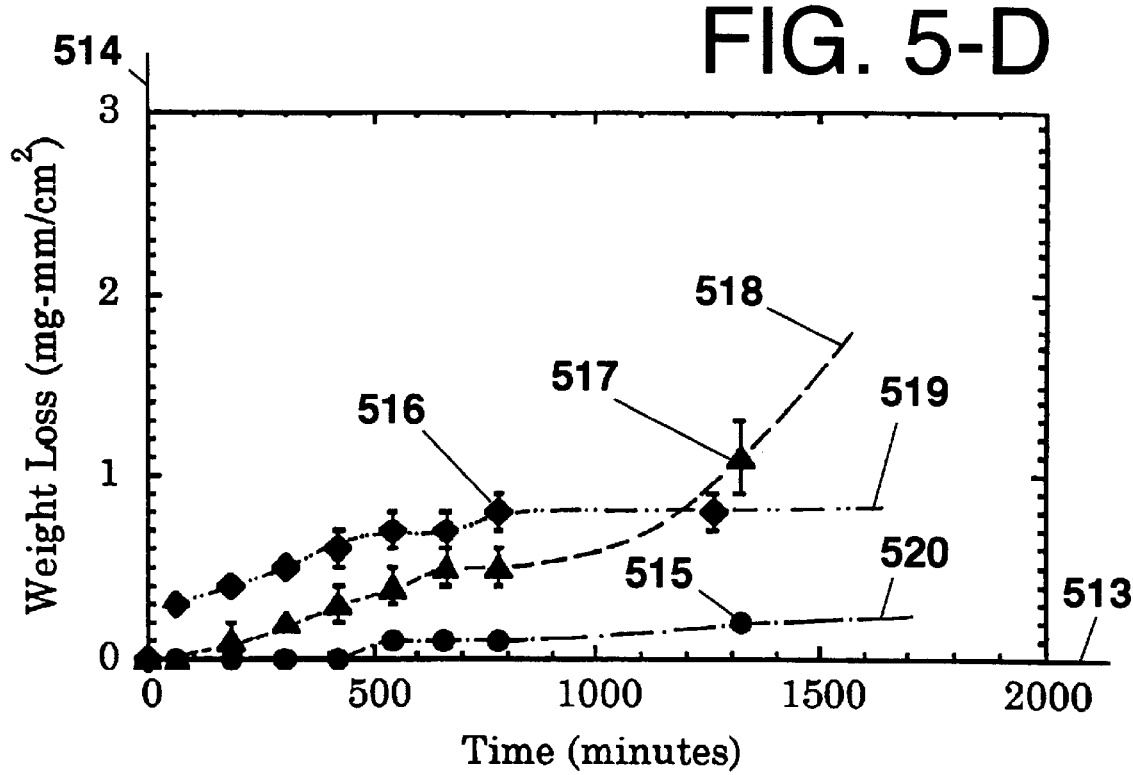
FIG. 5-D

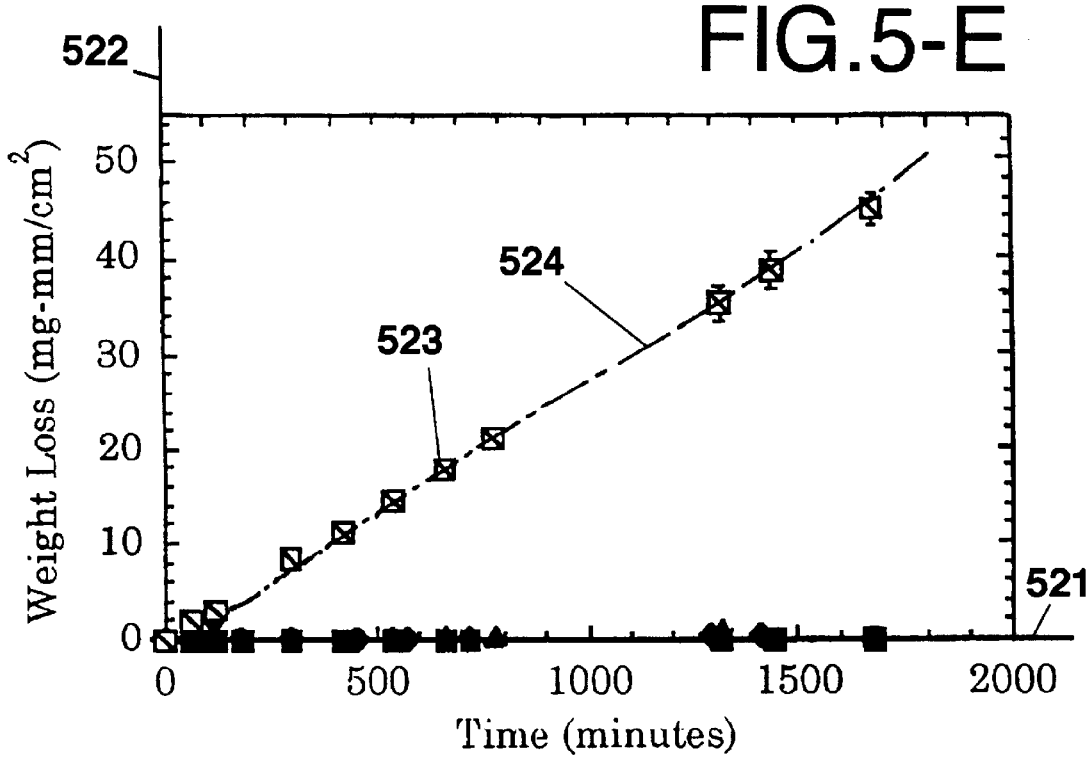
FIG.5-E
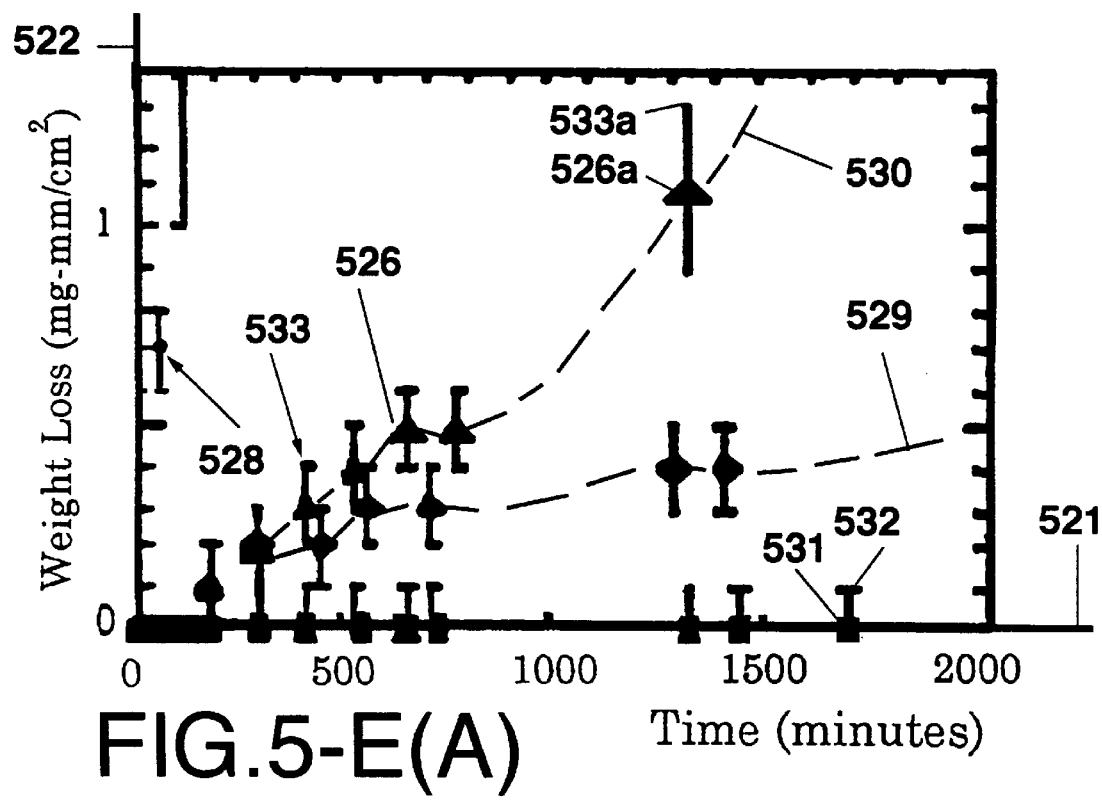
FIG.5-E(A)

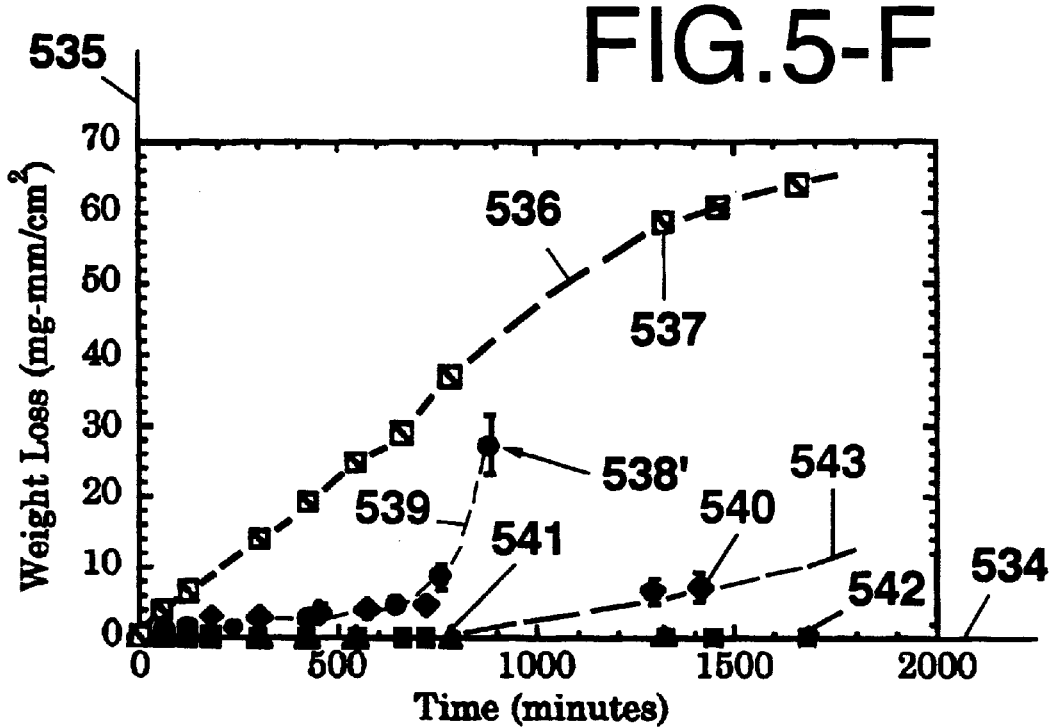
FIG.5-F
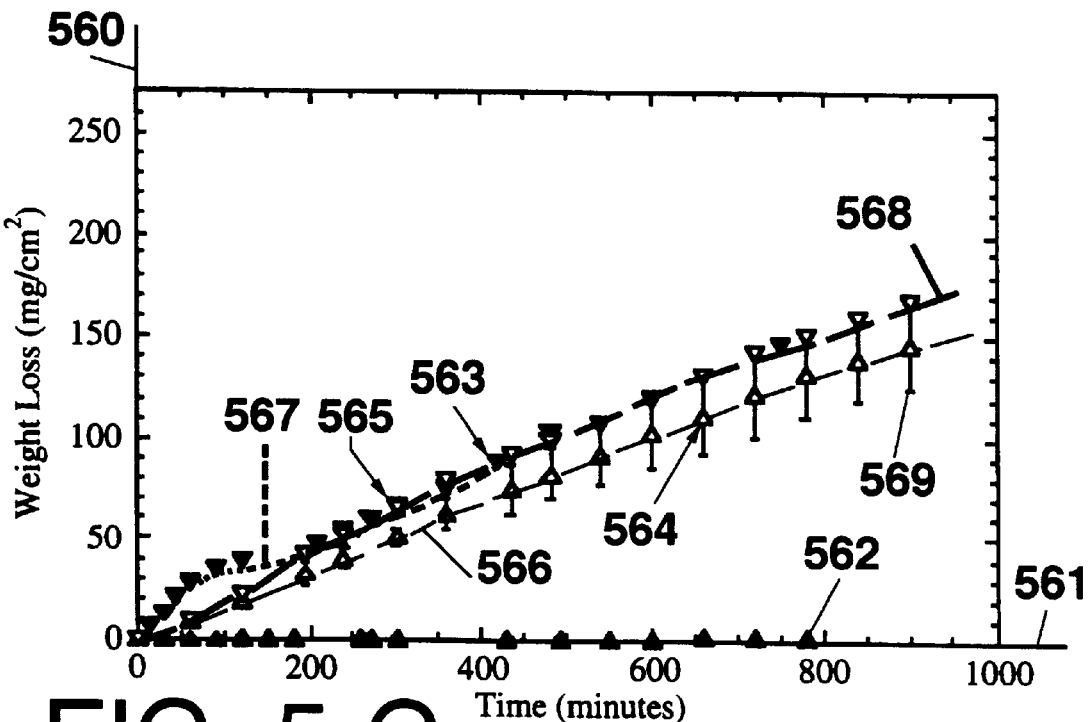
FIG. 5-G

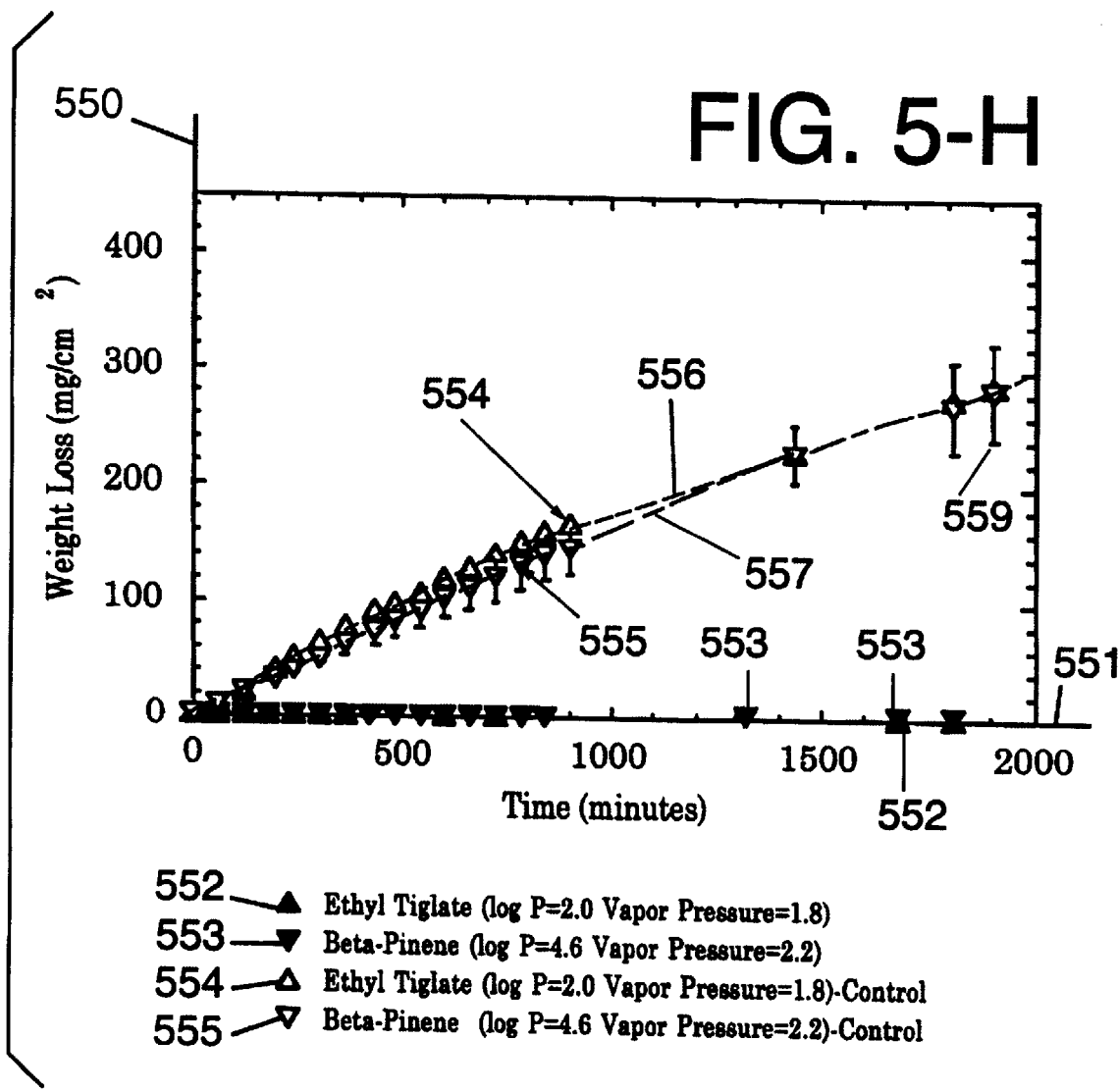

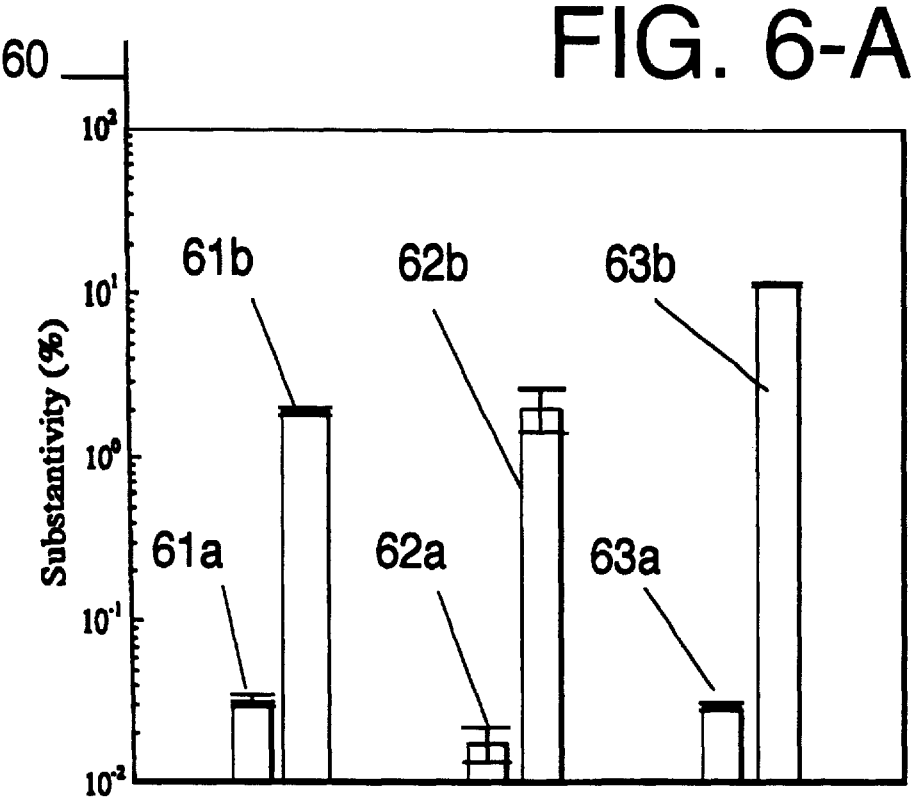
FIG. 6-A
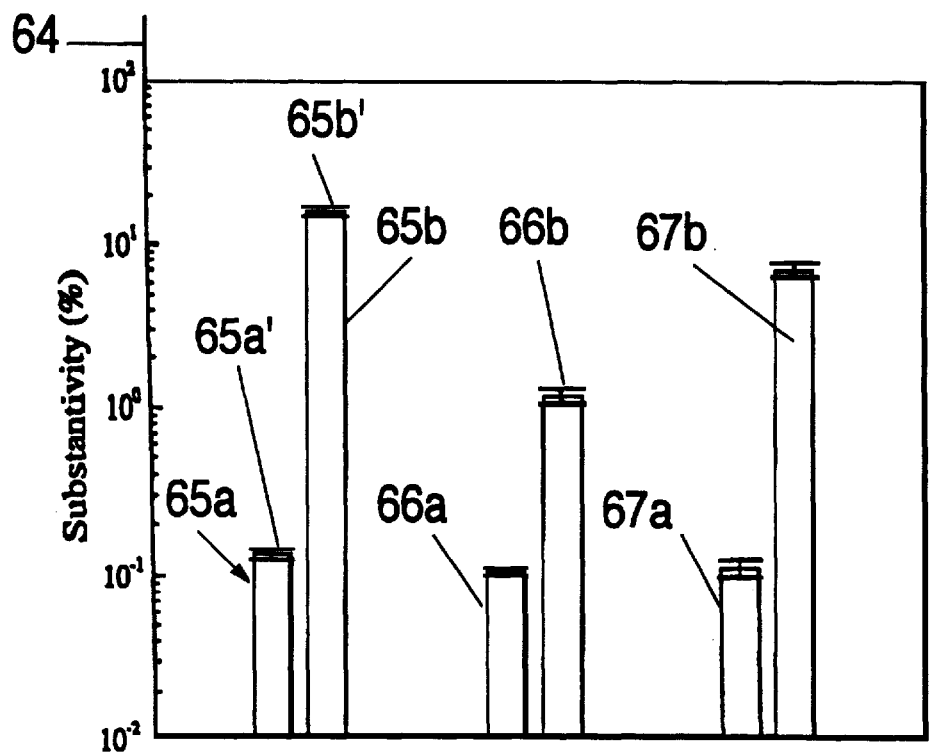
FIG. 6-B

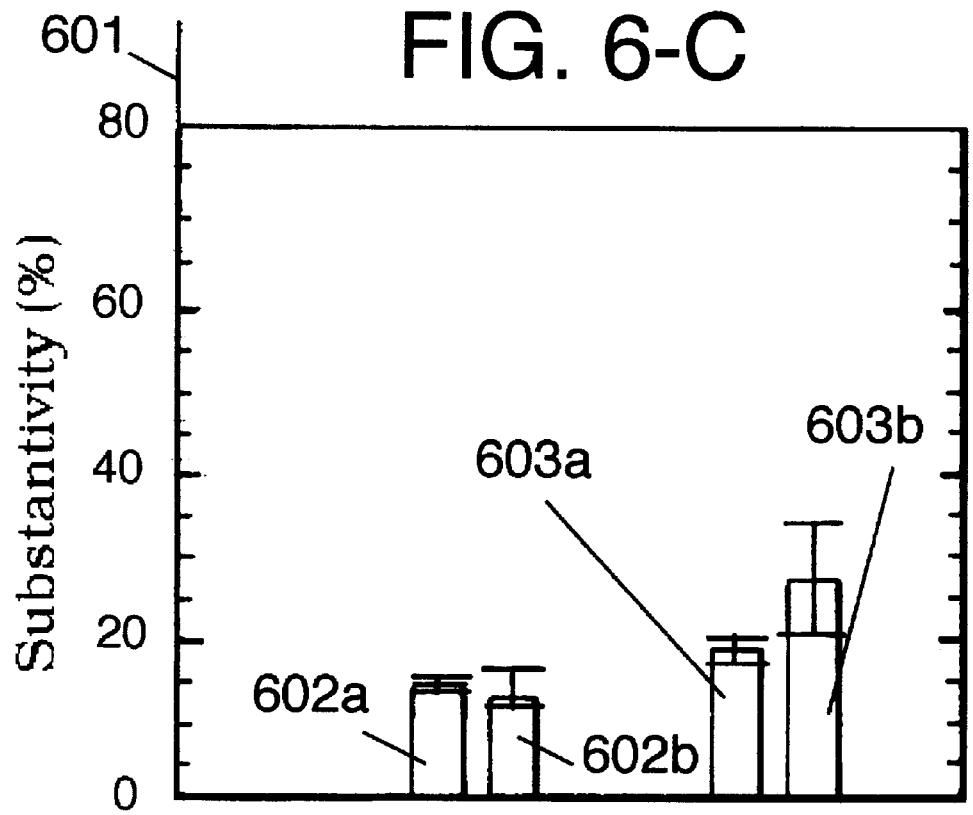
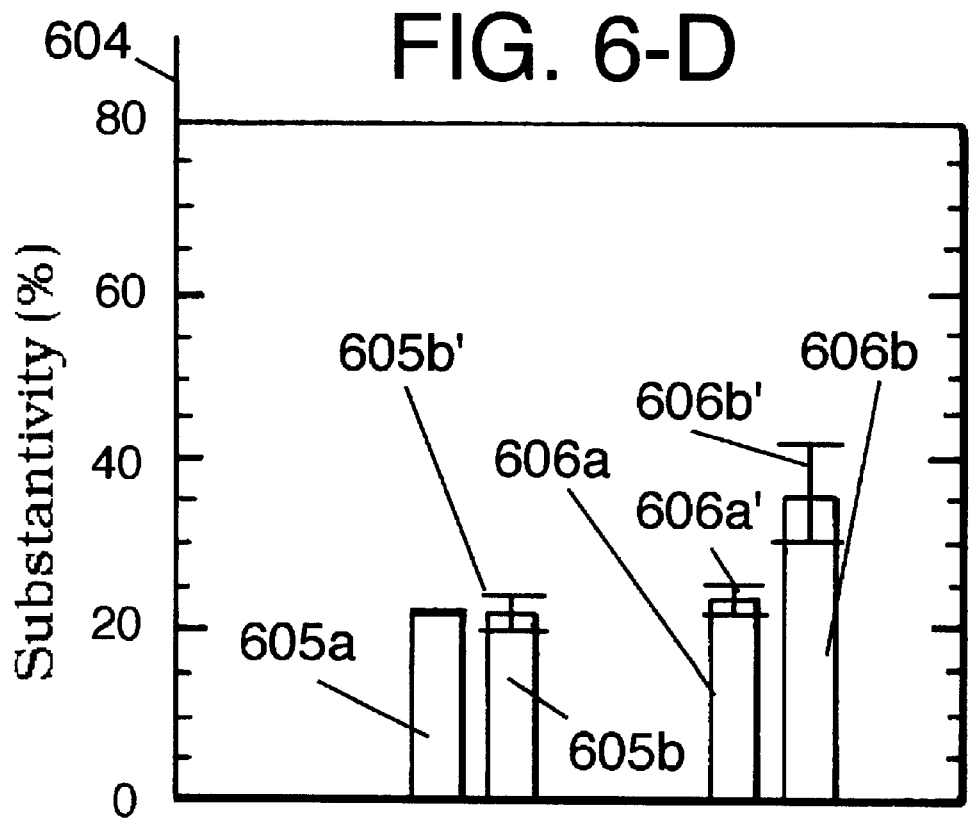

FIG. 7-A
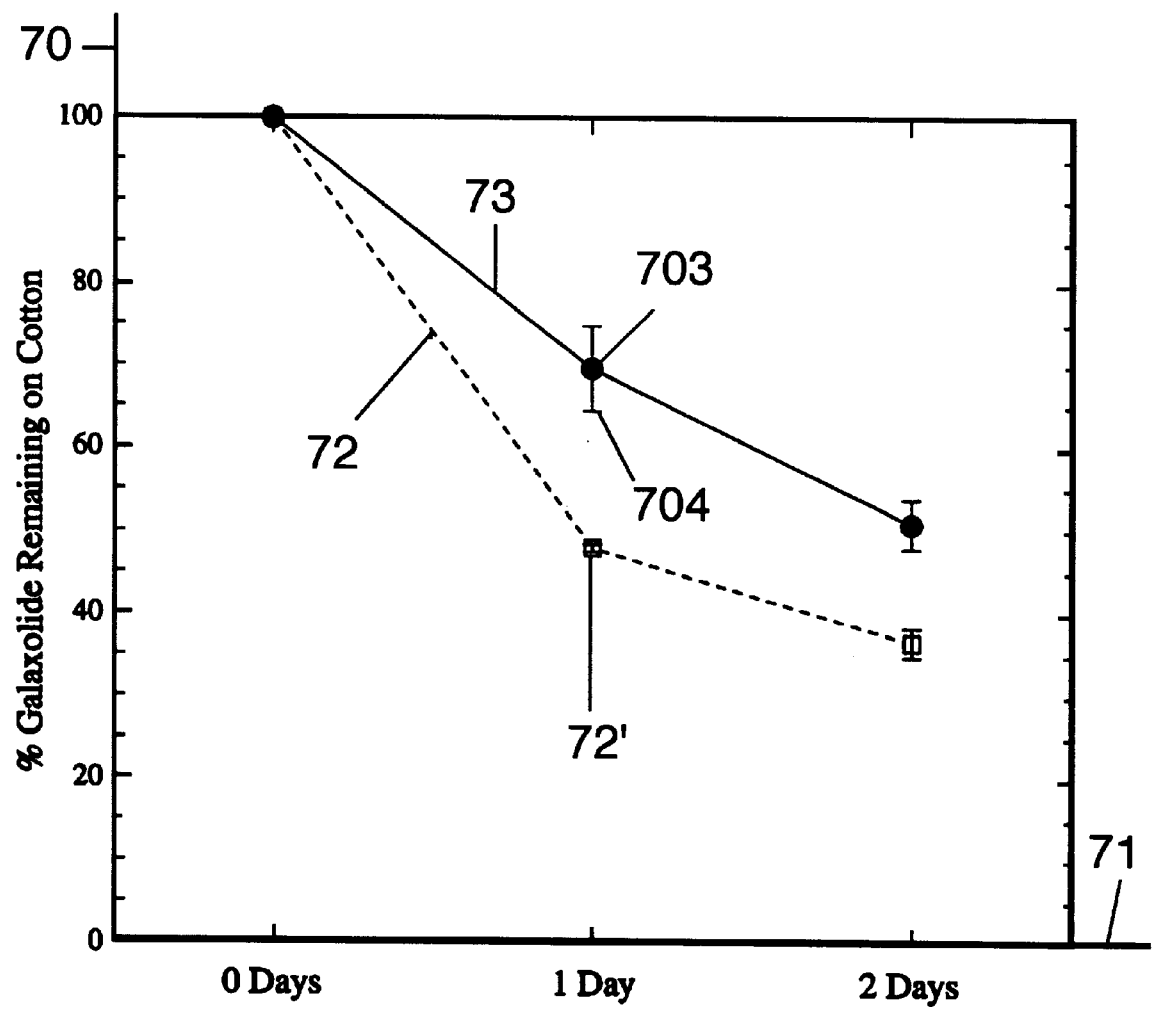

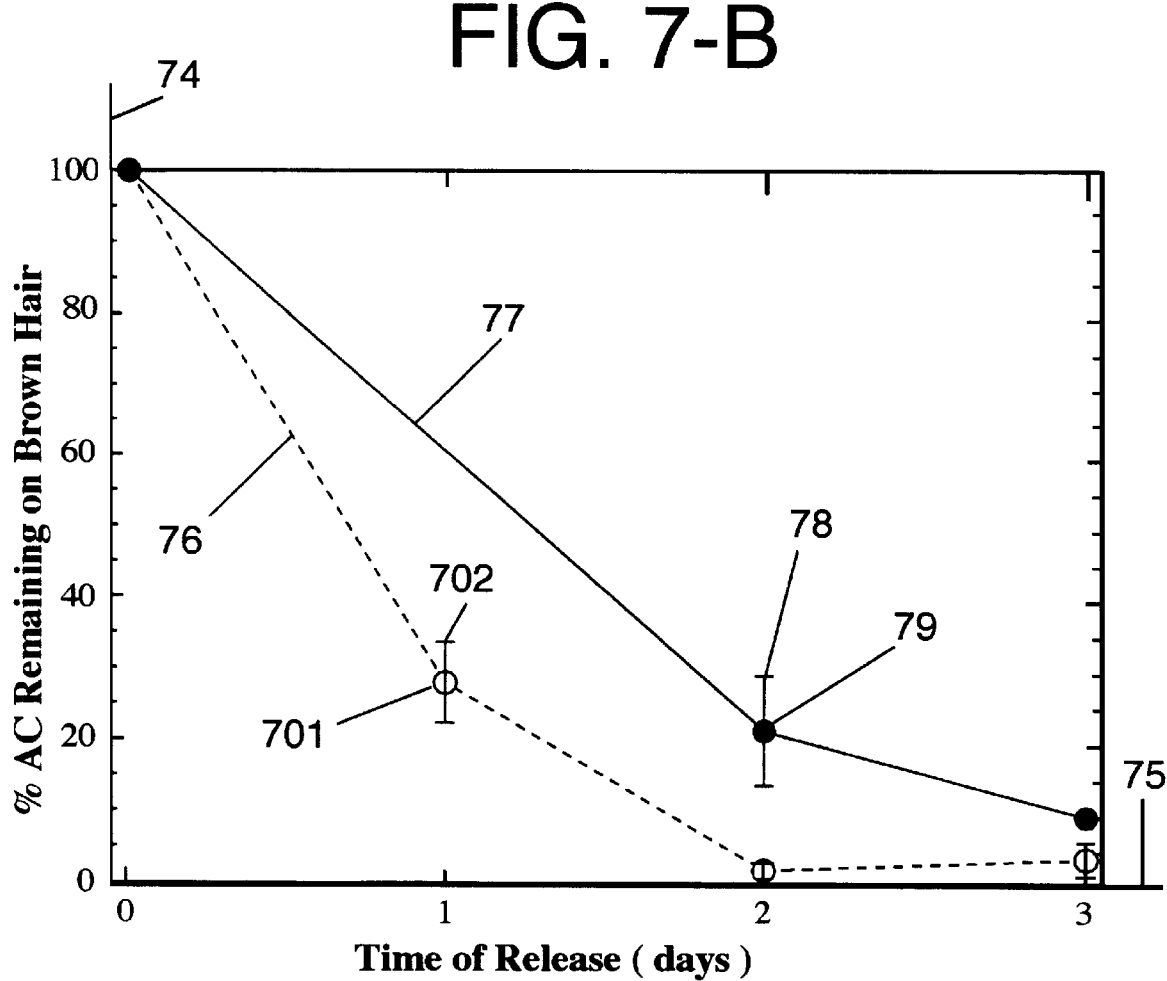

FIG. 8-A
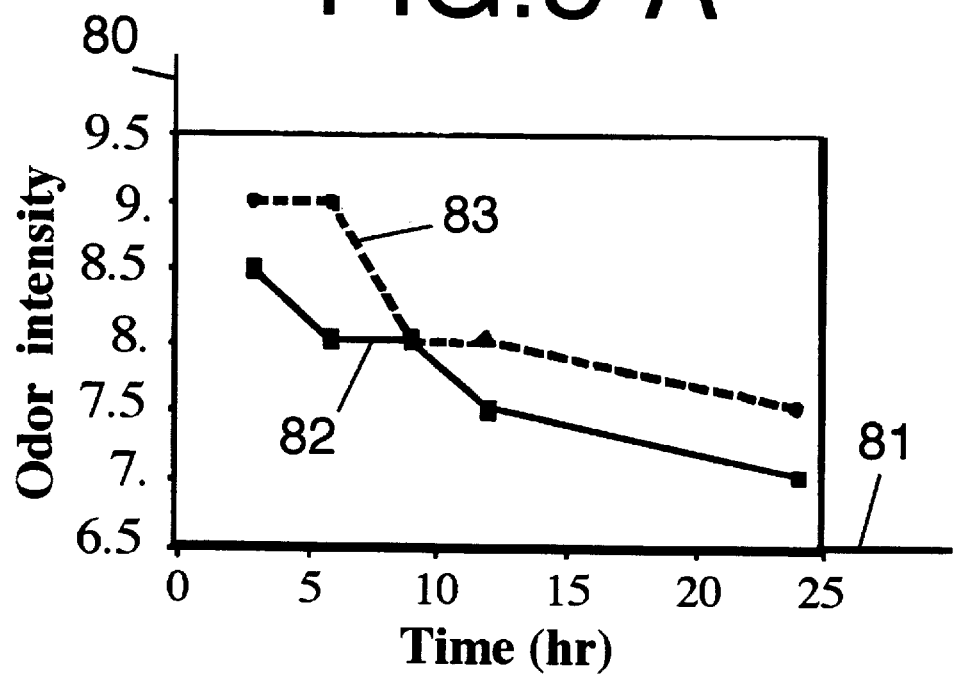
FIG. 8-B
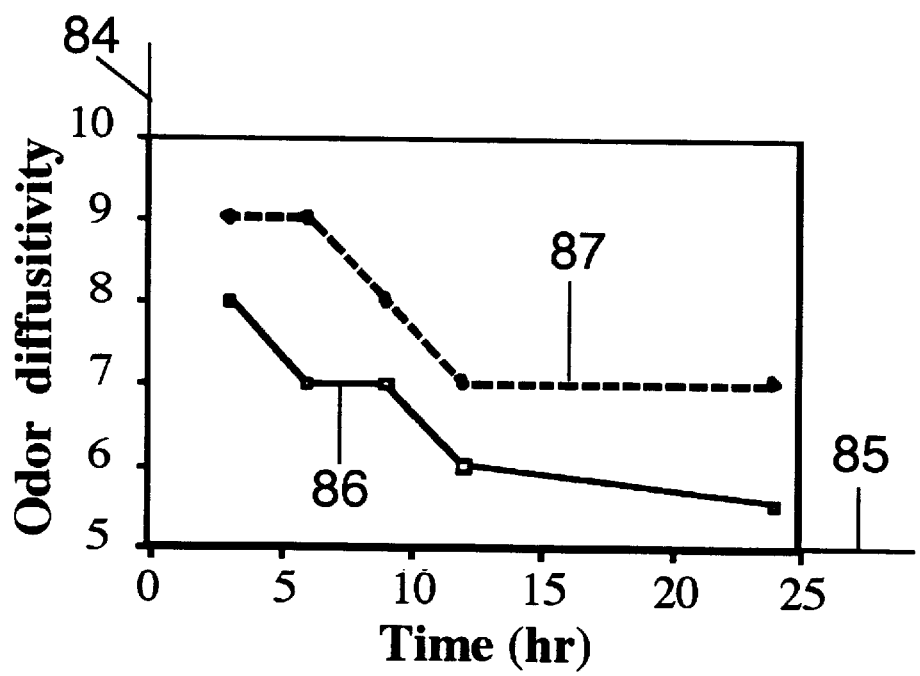

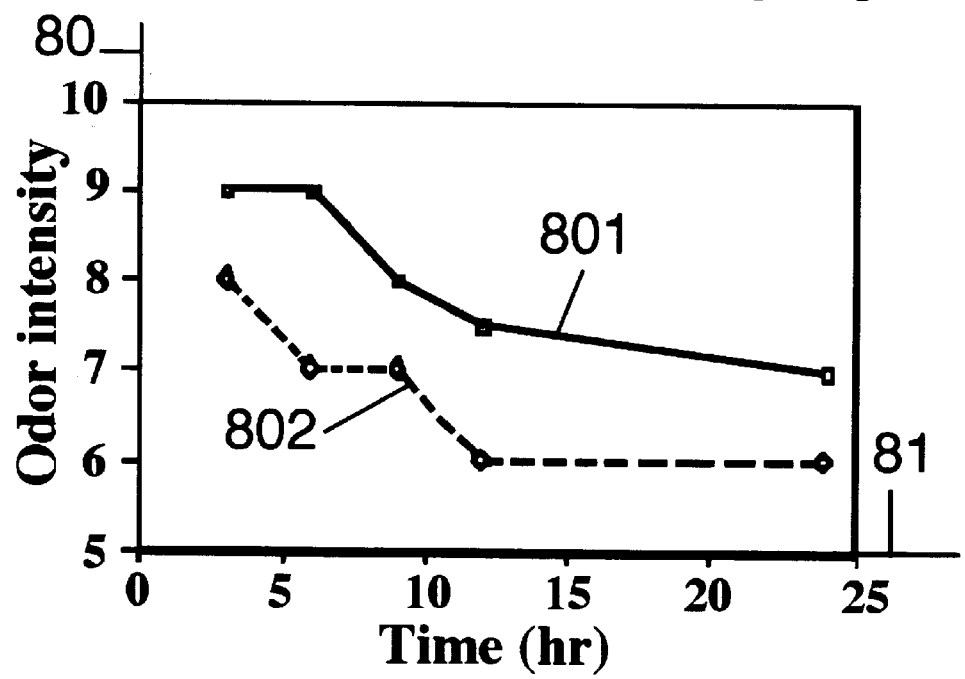
FIG. 8-C
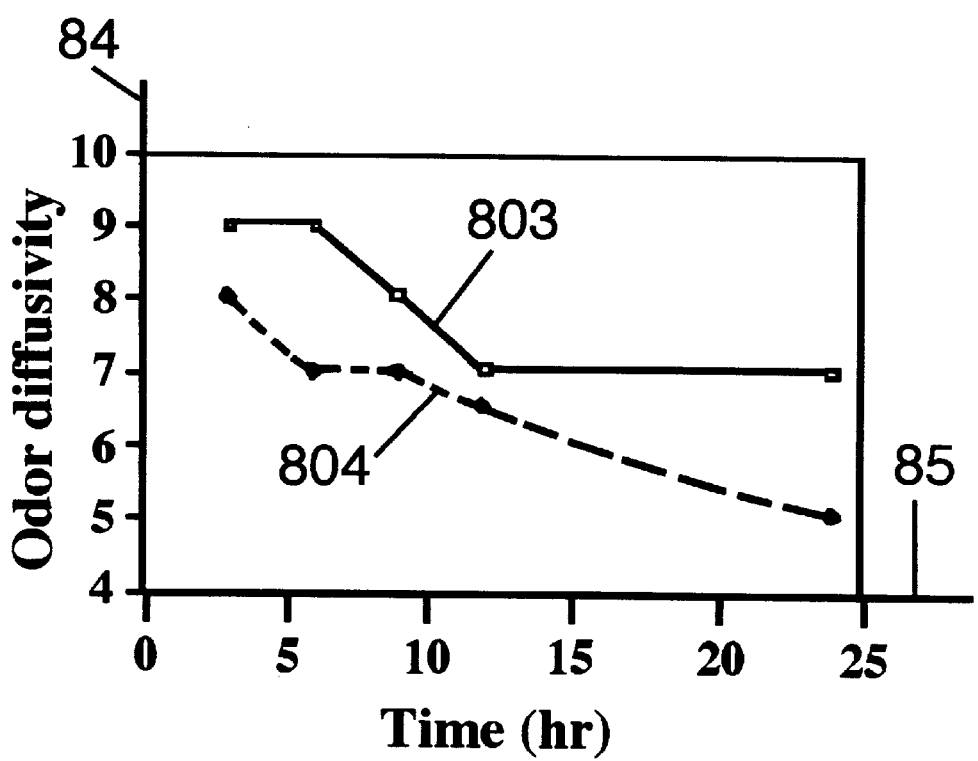
FIG. 8-D

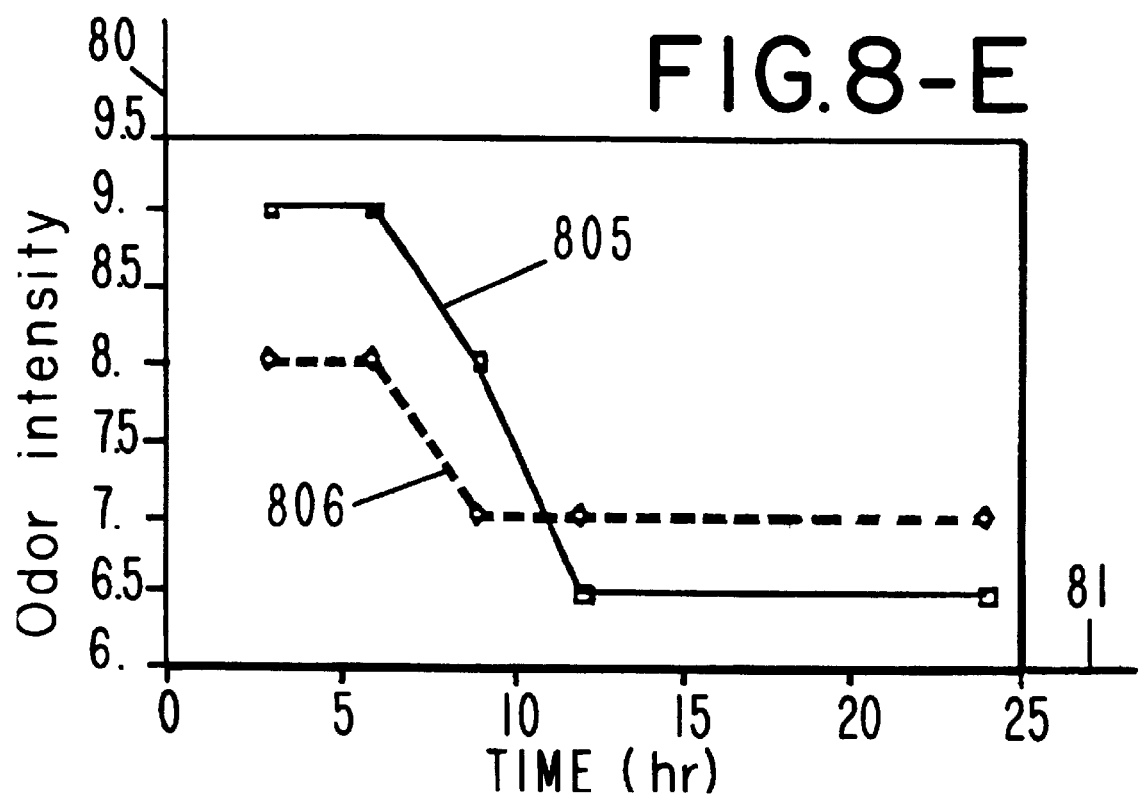
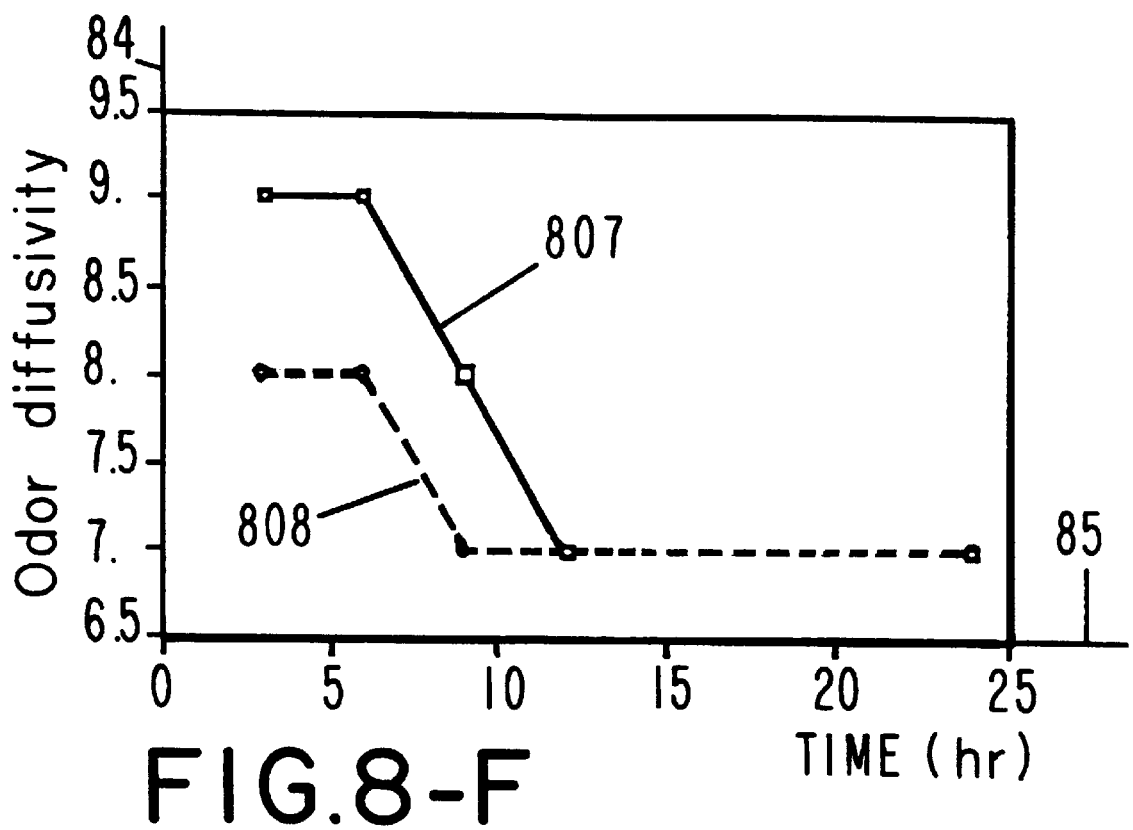

FIG. 8-G
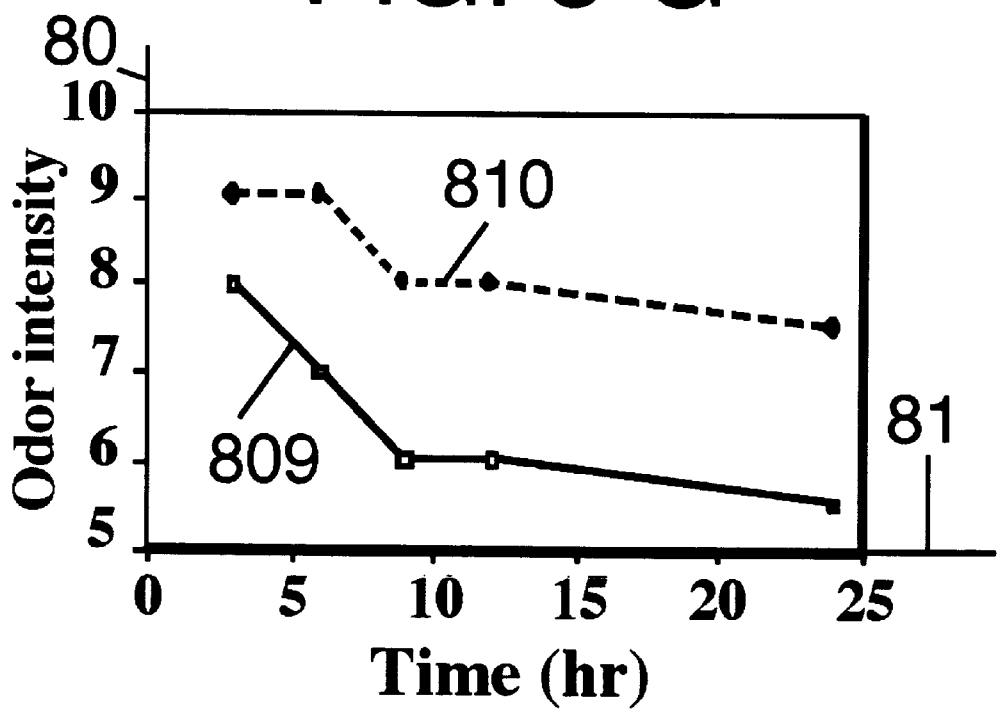
FIG. 8-H
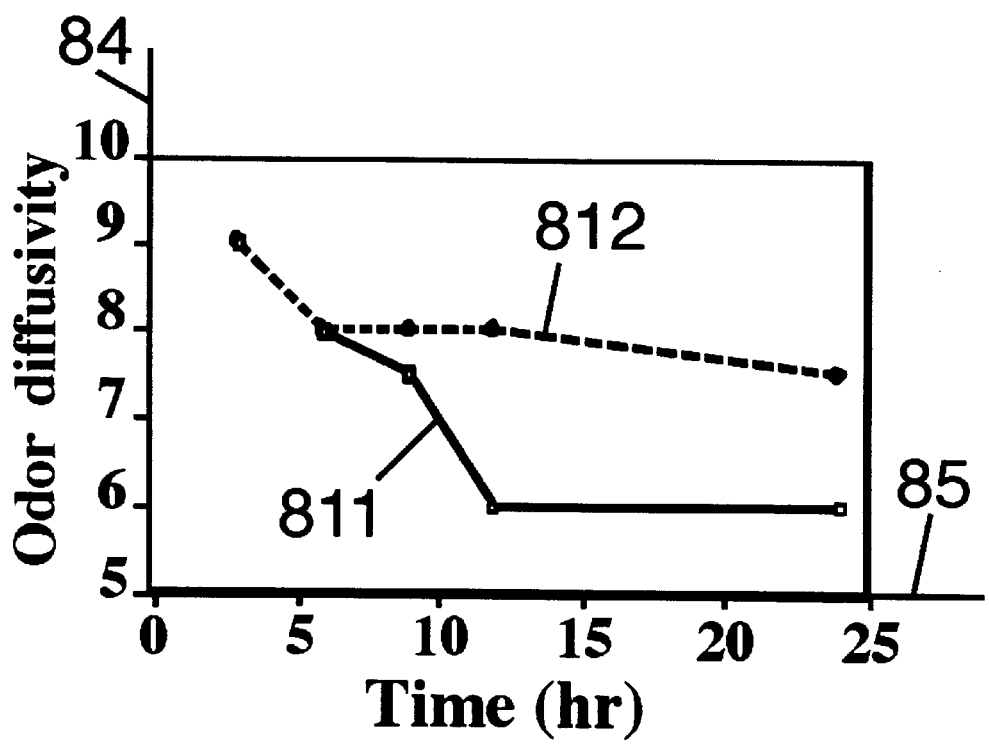

FIG. 8-I
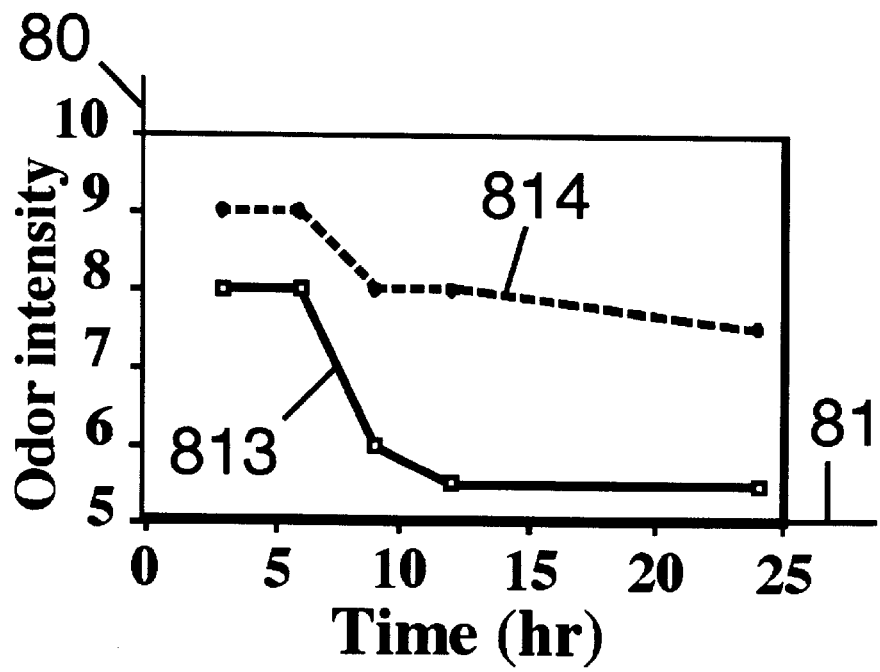
FIG. 8-J
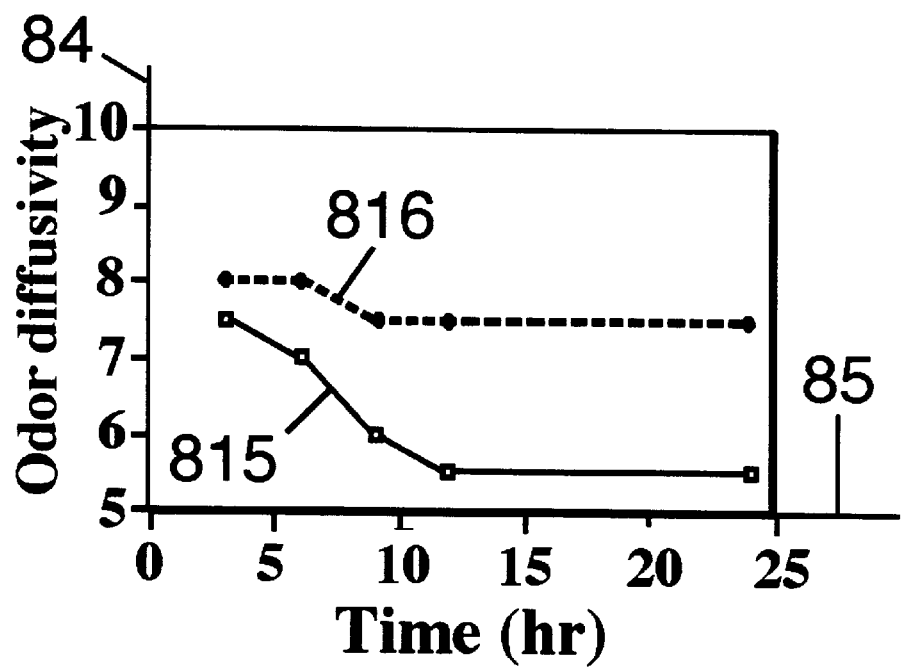

FIG. 8-K
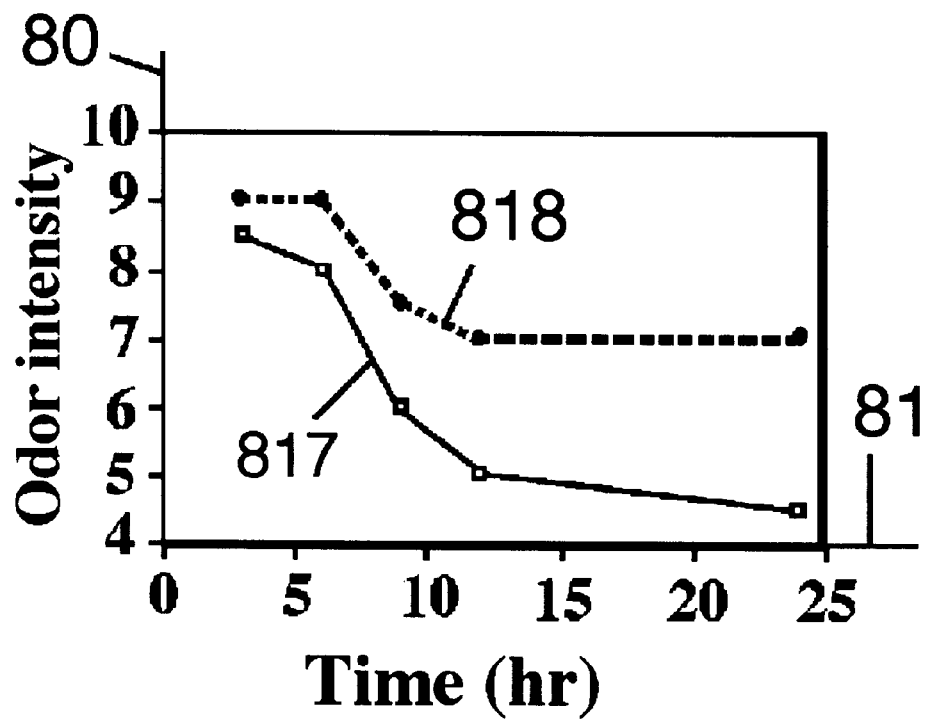
FIG. 8-L
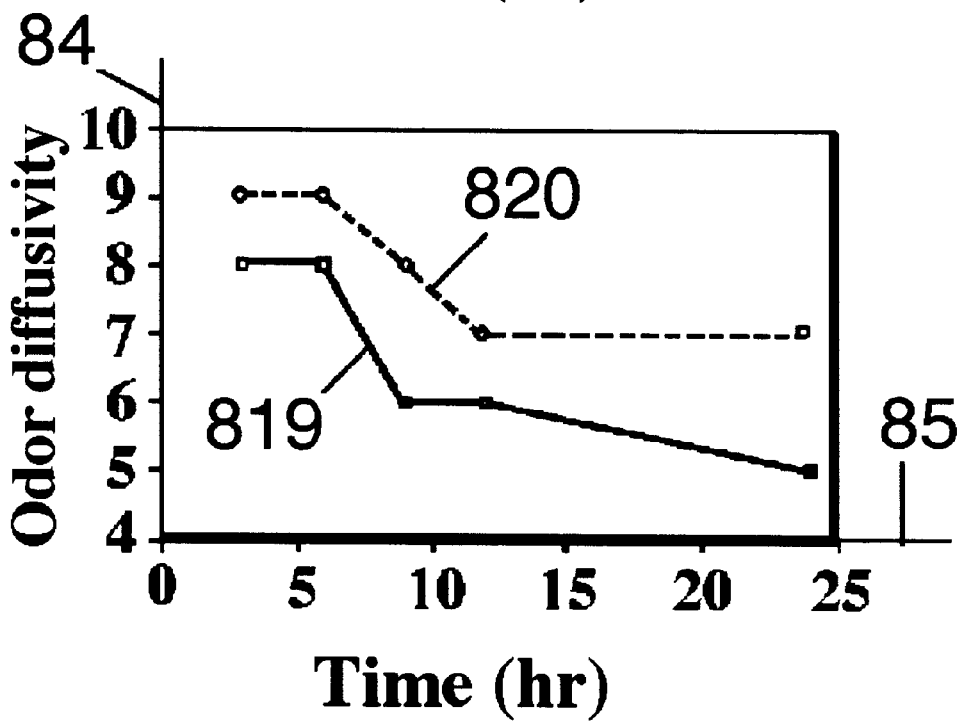

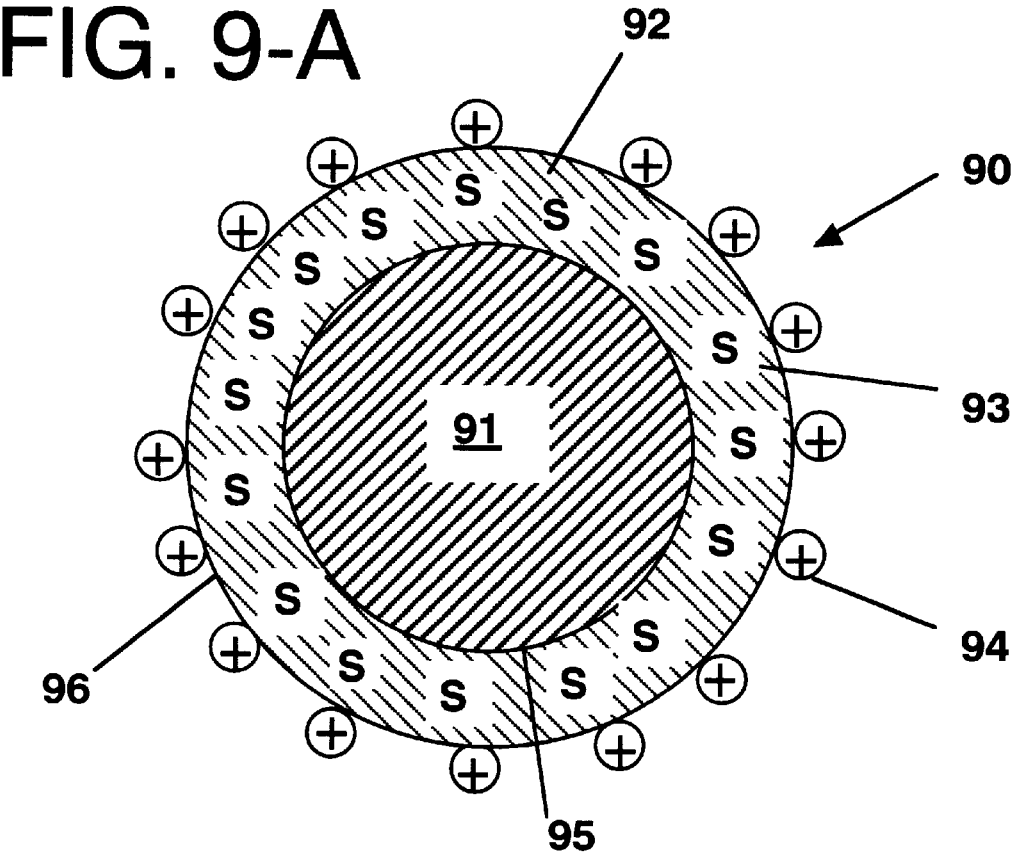
FIG. 9-A
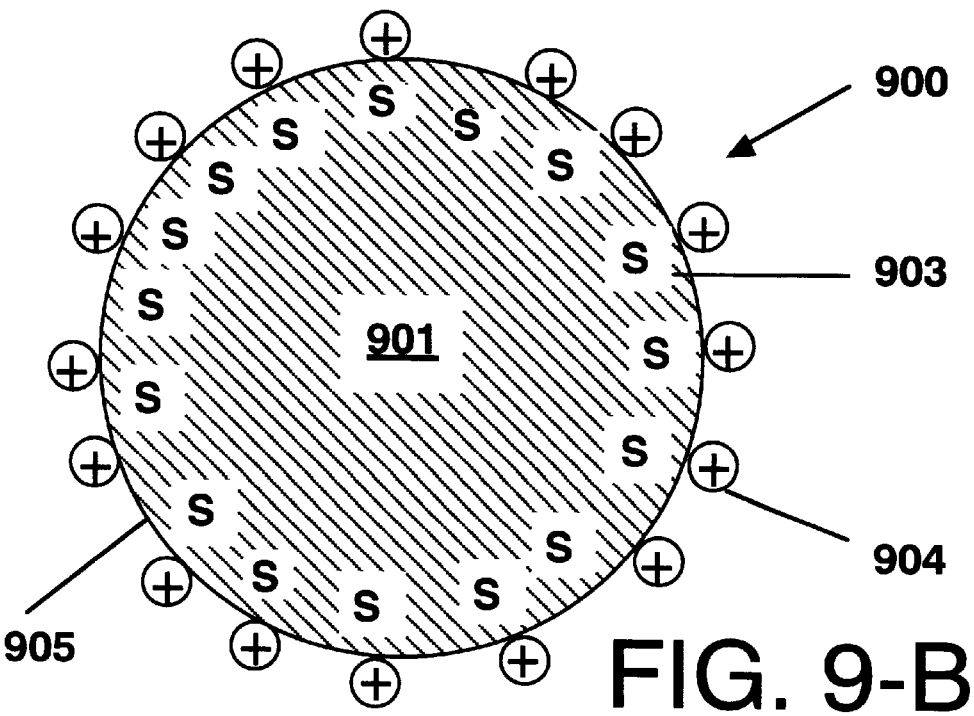
FIG. 9-B

FIG. 9-C
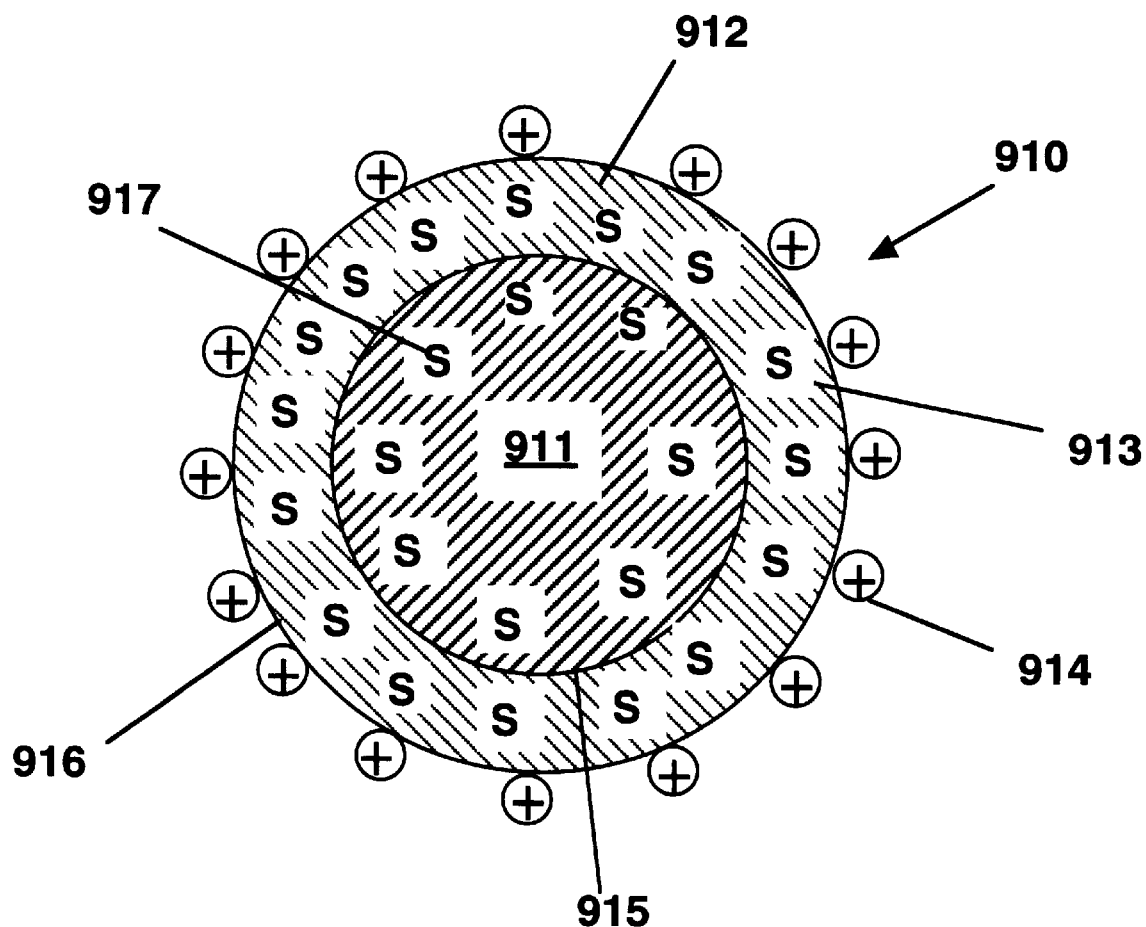

FIG.10-A
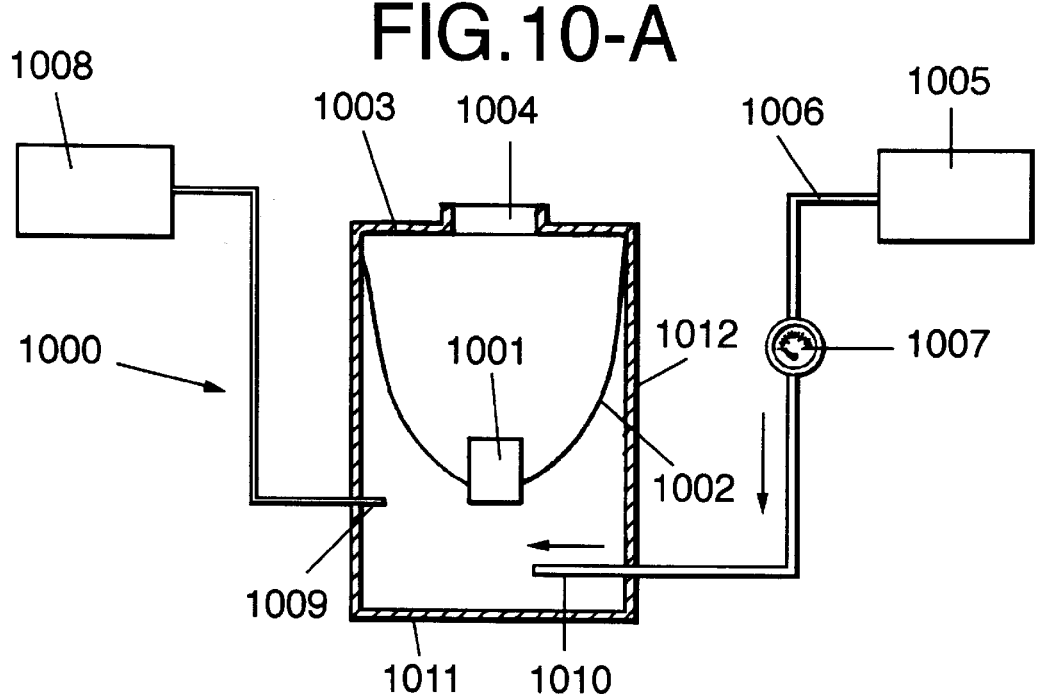
FIG.10-B
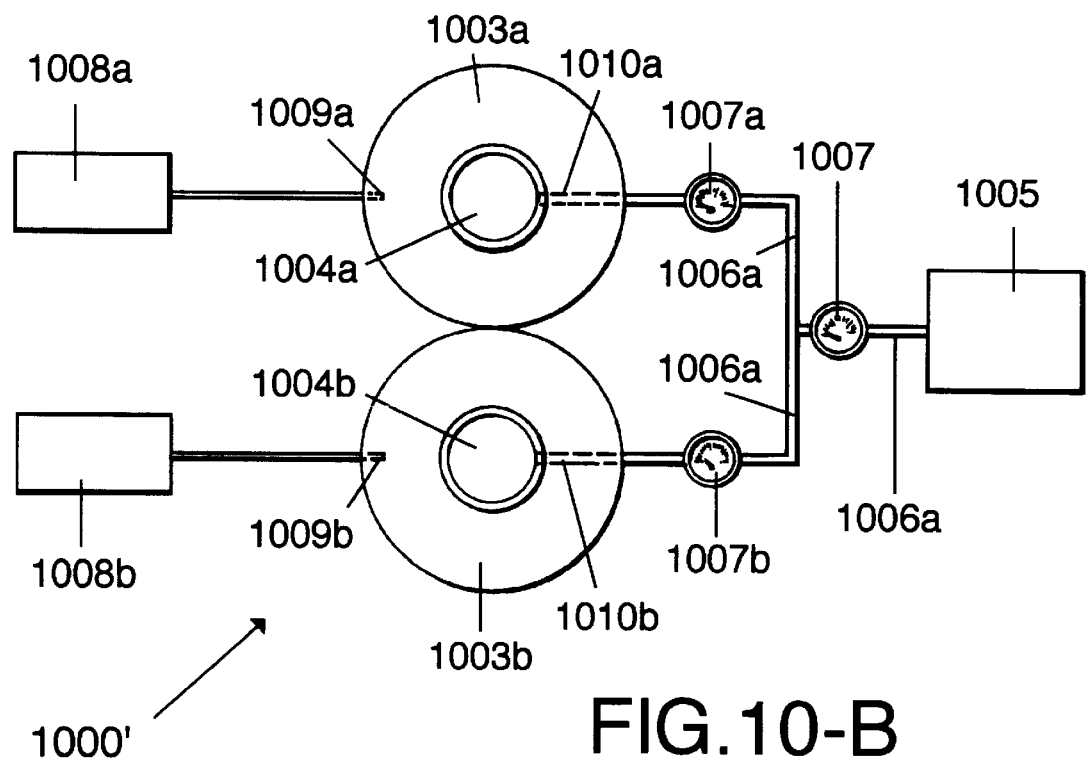

FIG.11-A
PRIOR ART
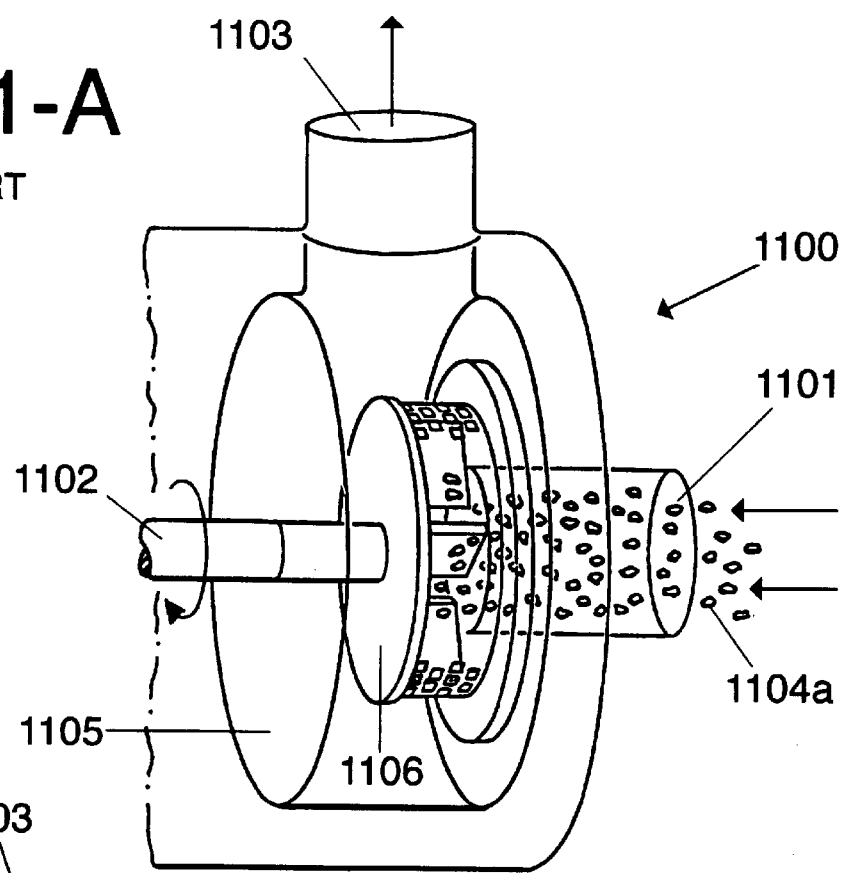
FIG.11-B
PRIOR ART
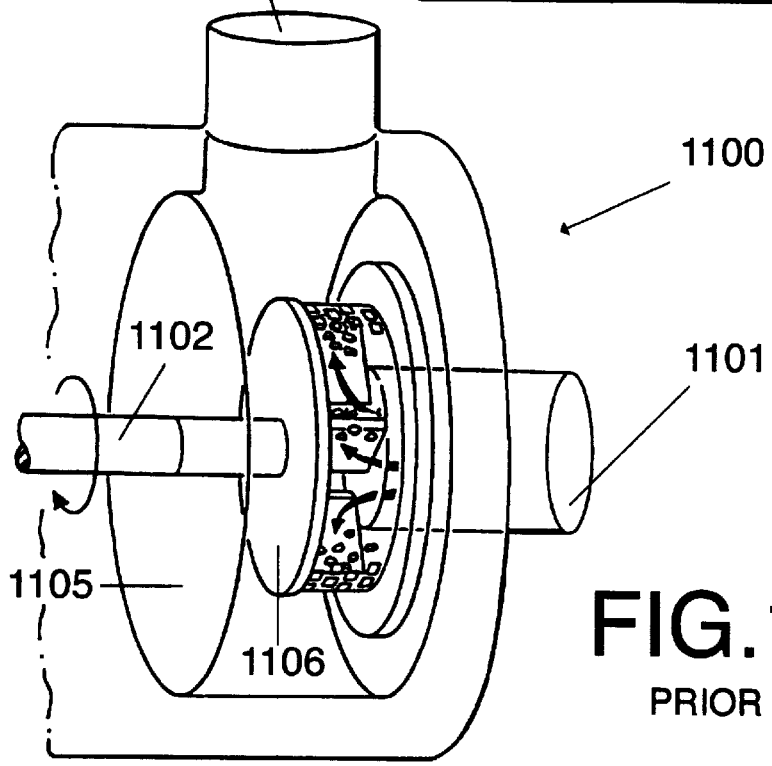

FIG. 11-C
PRIOR ART
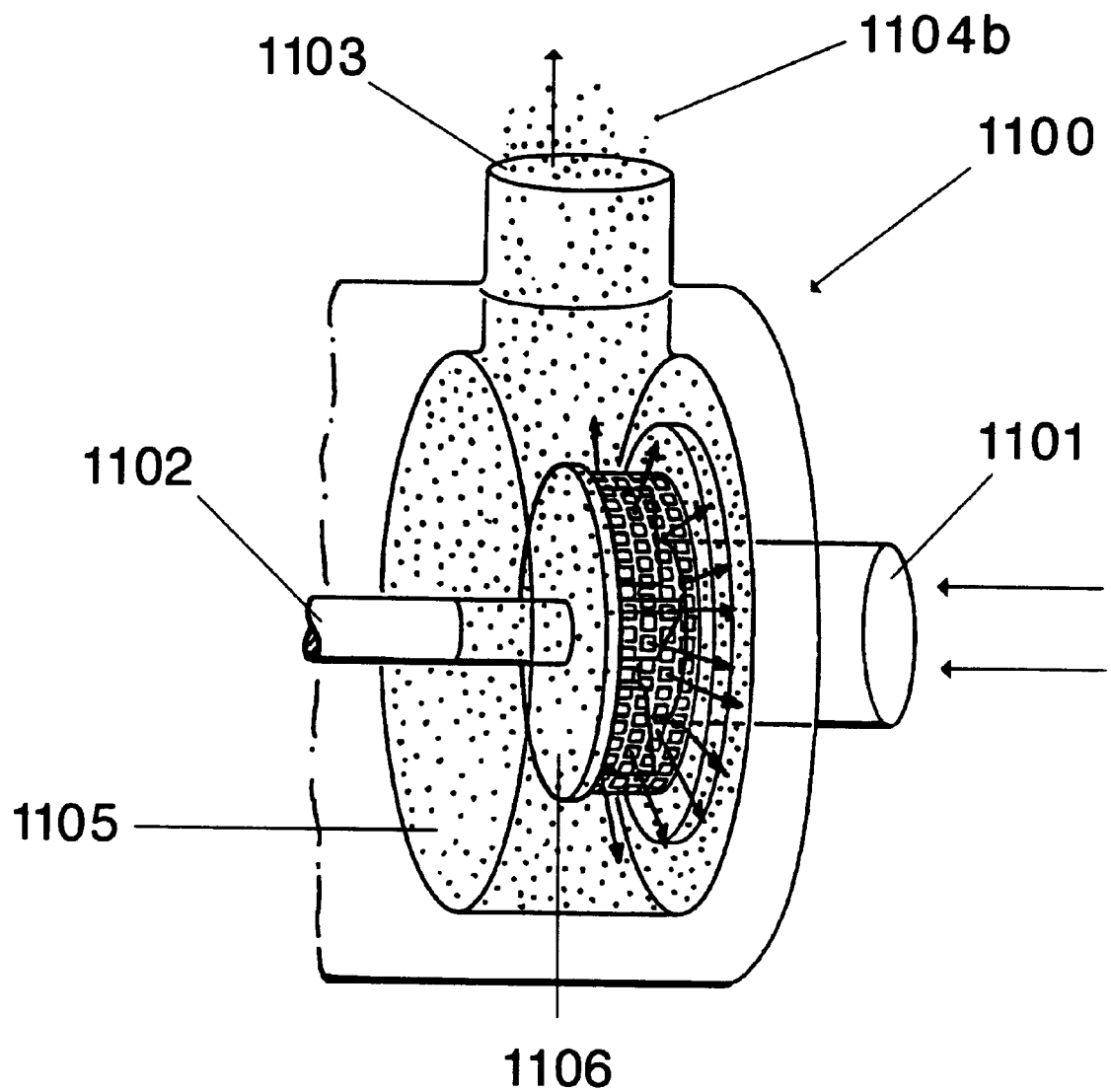

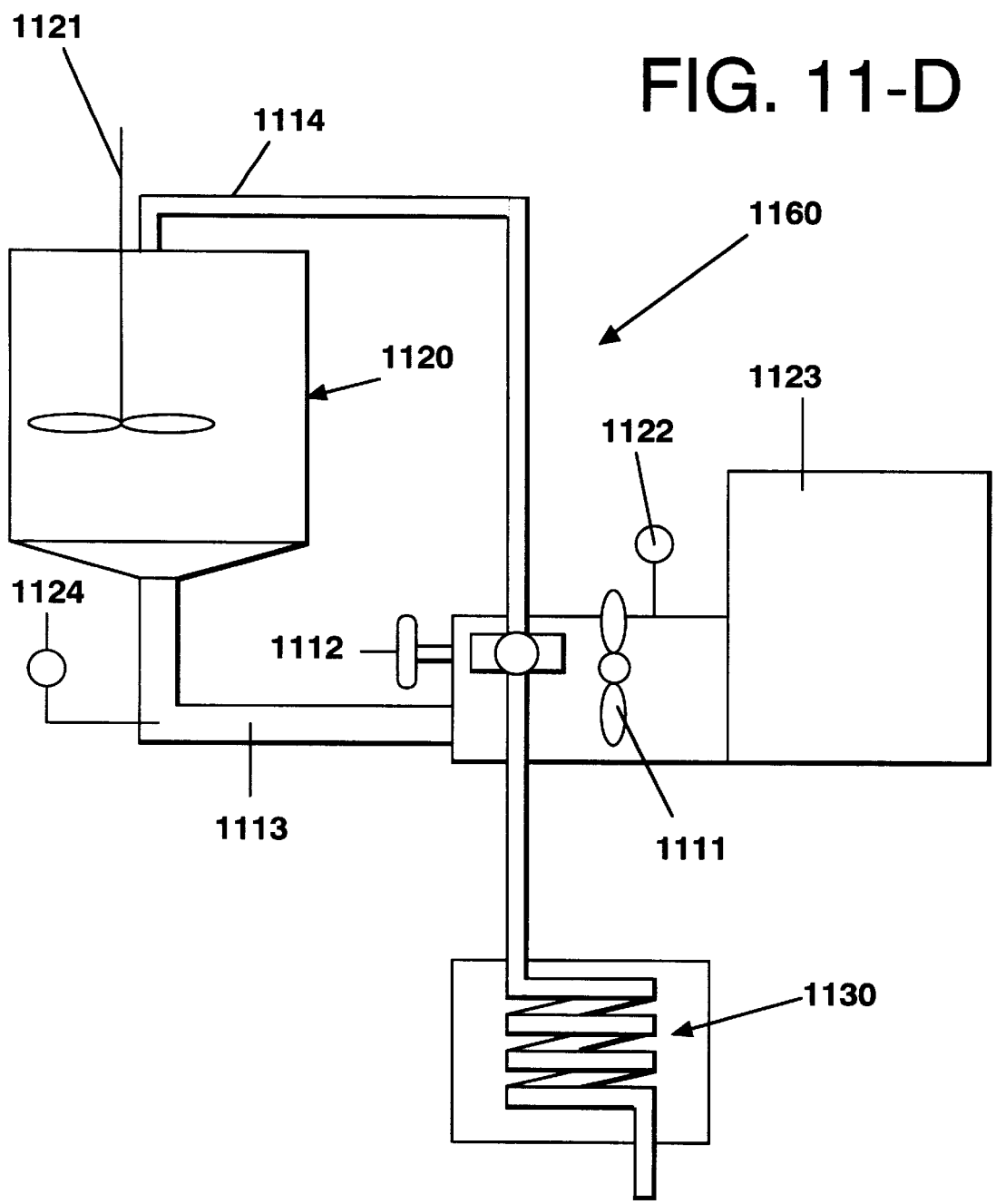
FIG. 11-D

FIG.11-E
PRIOR ART
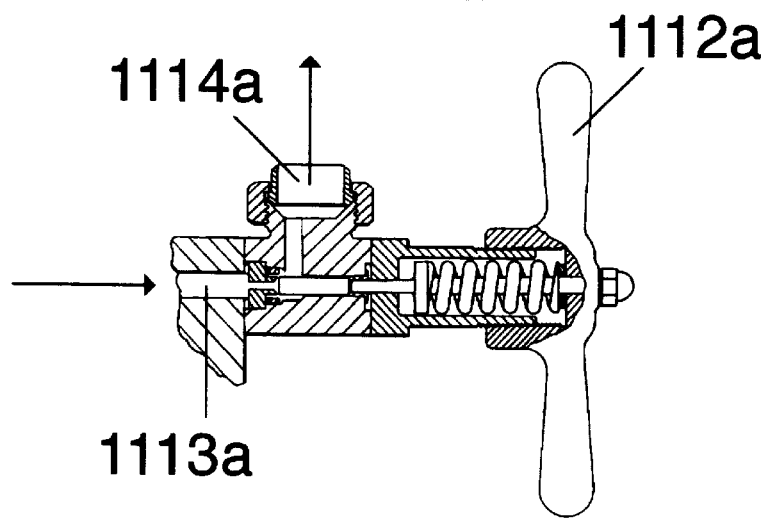
FIG.11-F
PRIOR ART
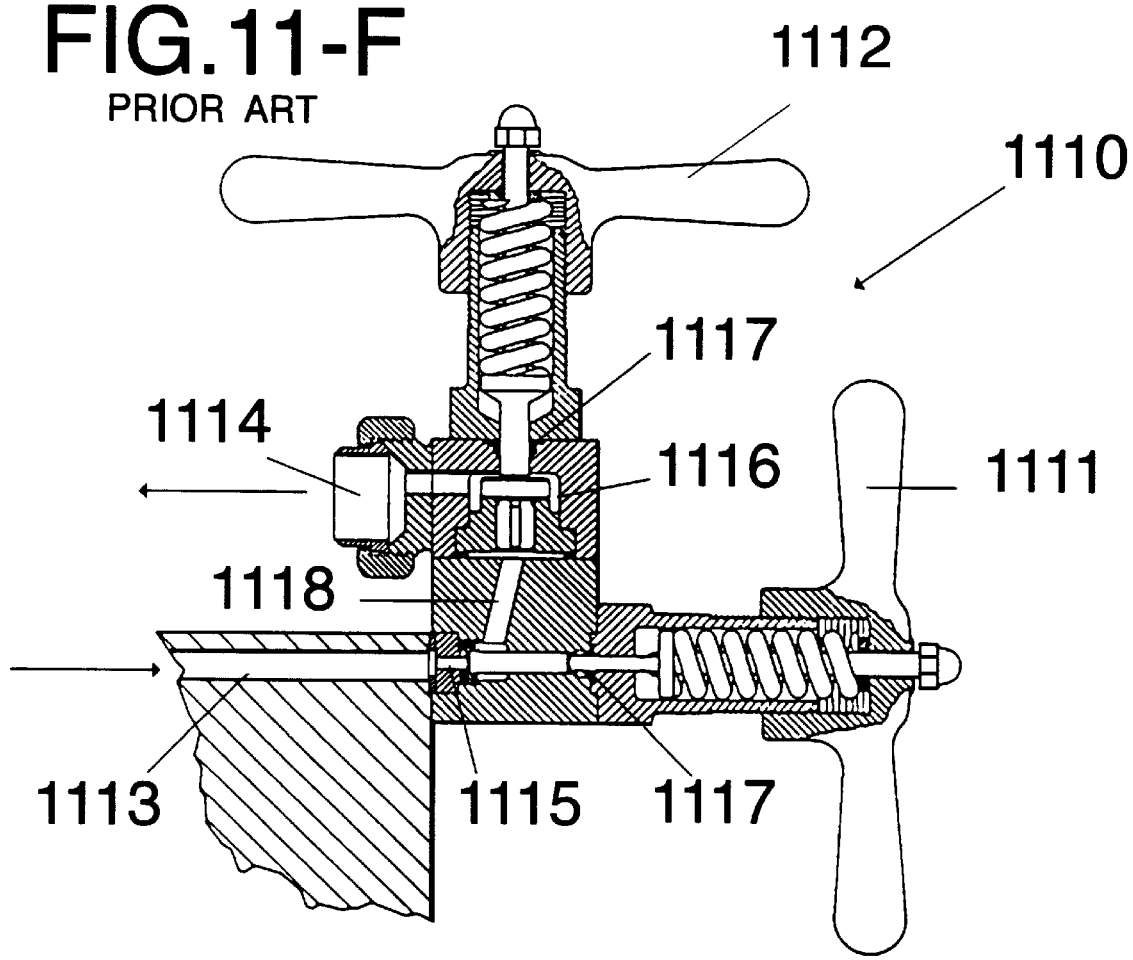

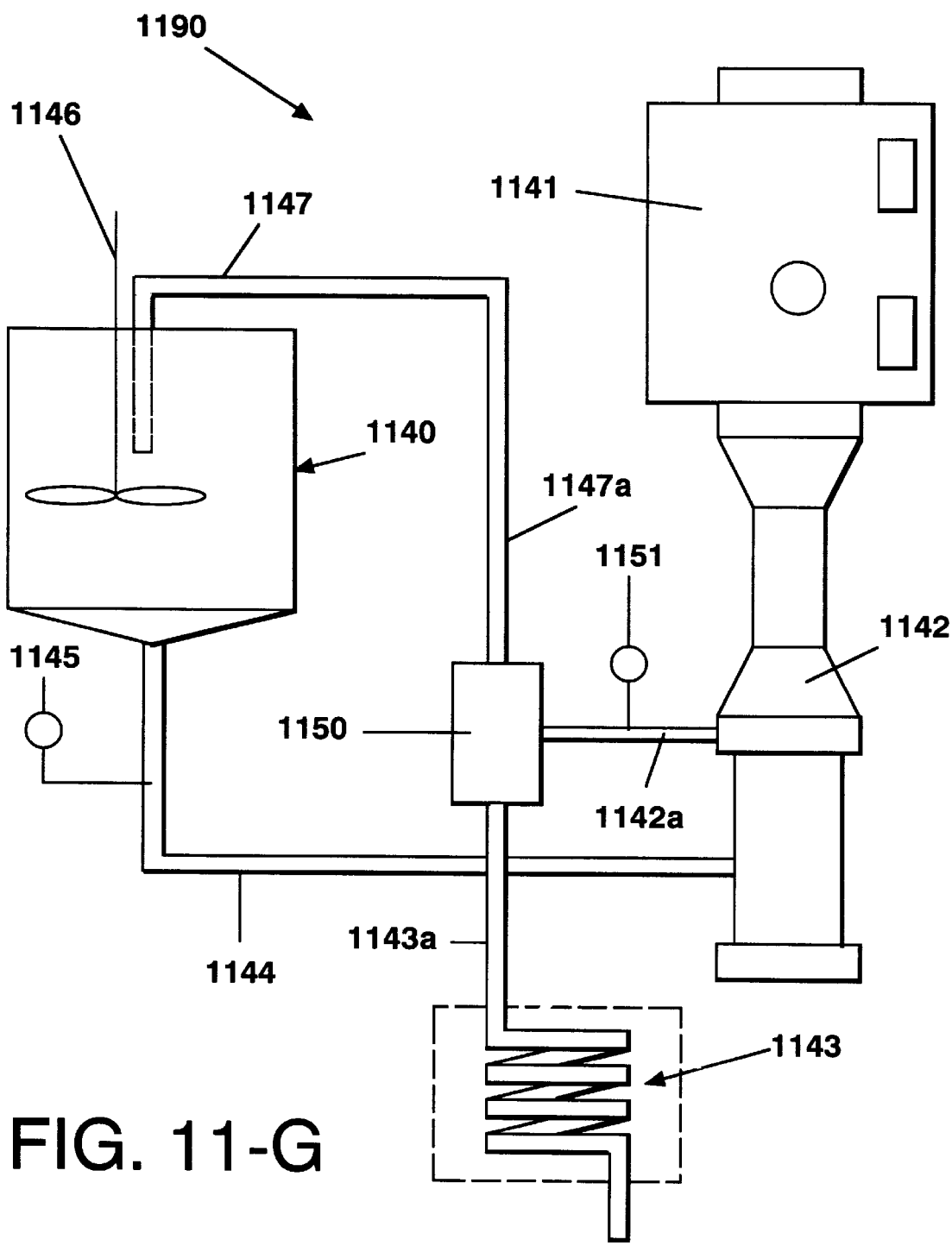
FIG. 11-G

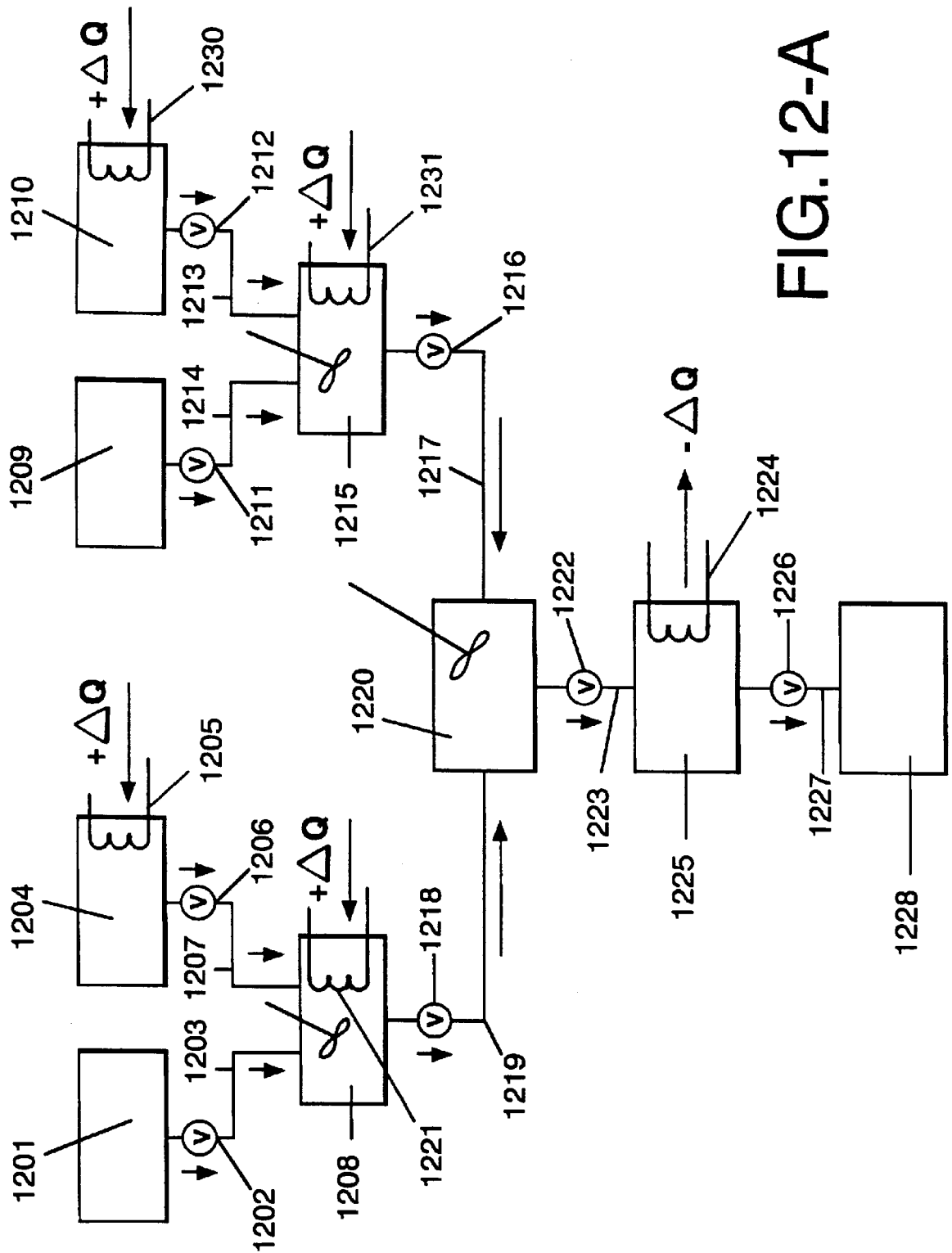
FIG.12-A

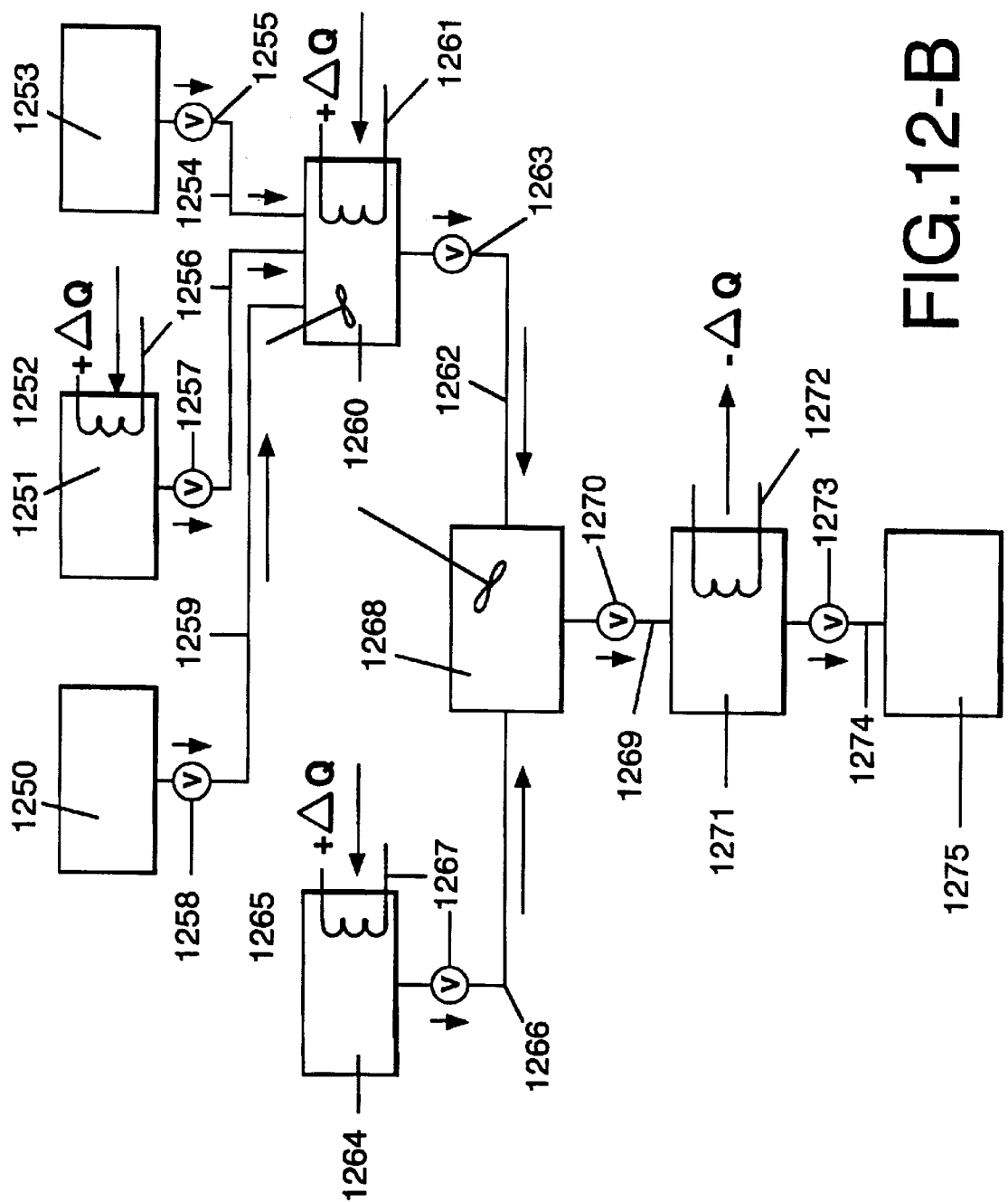
FIG.12-B

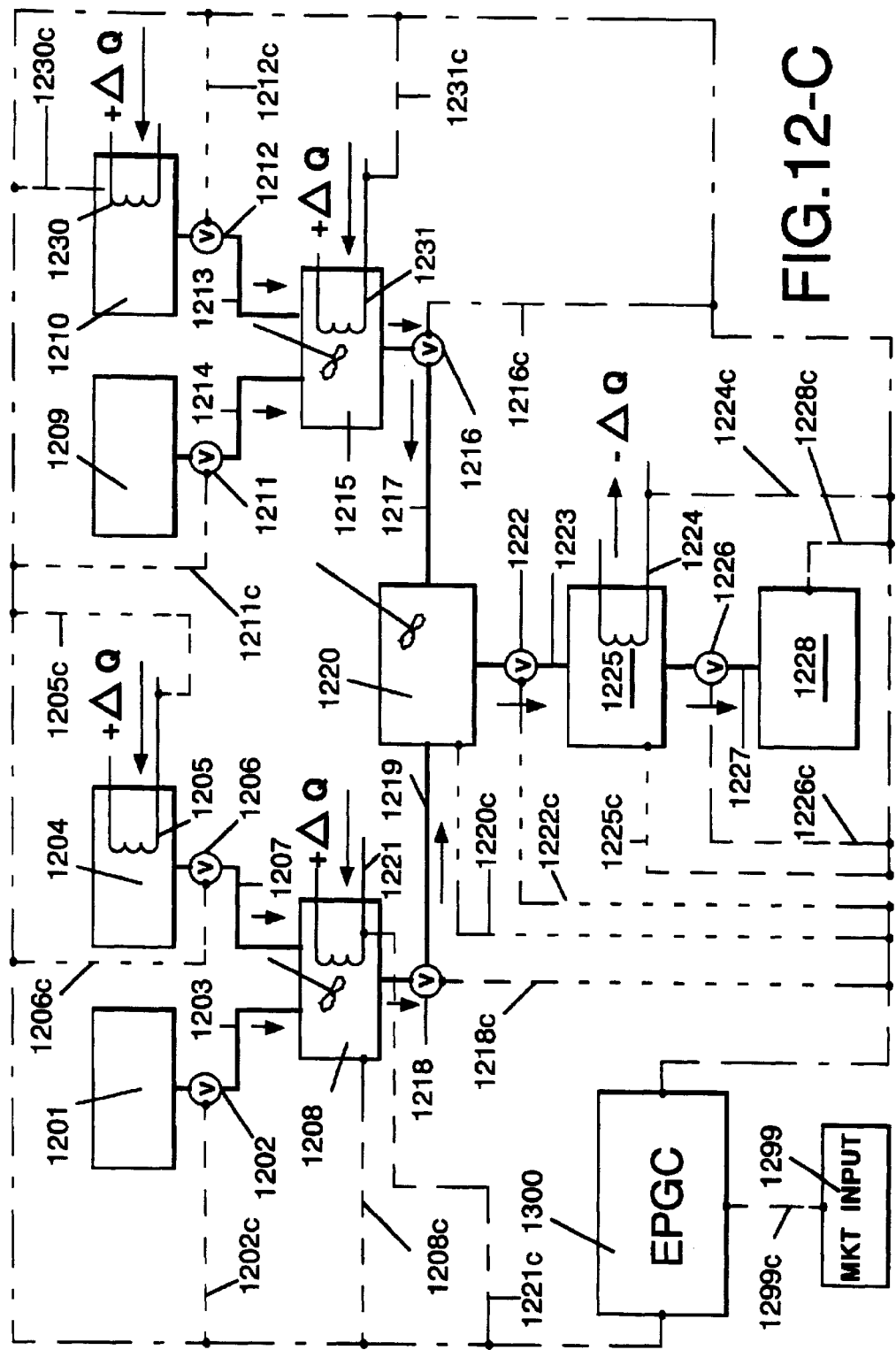
FIG.12-C

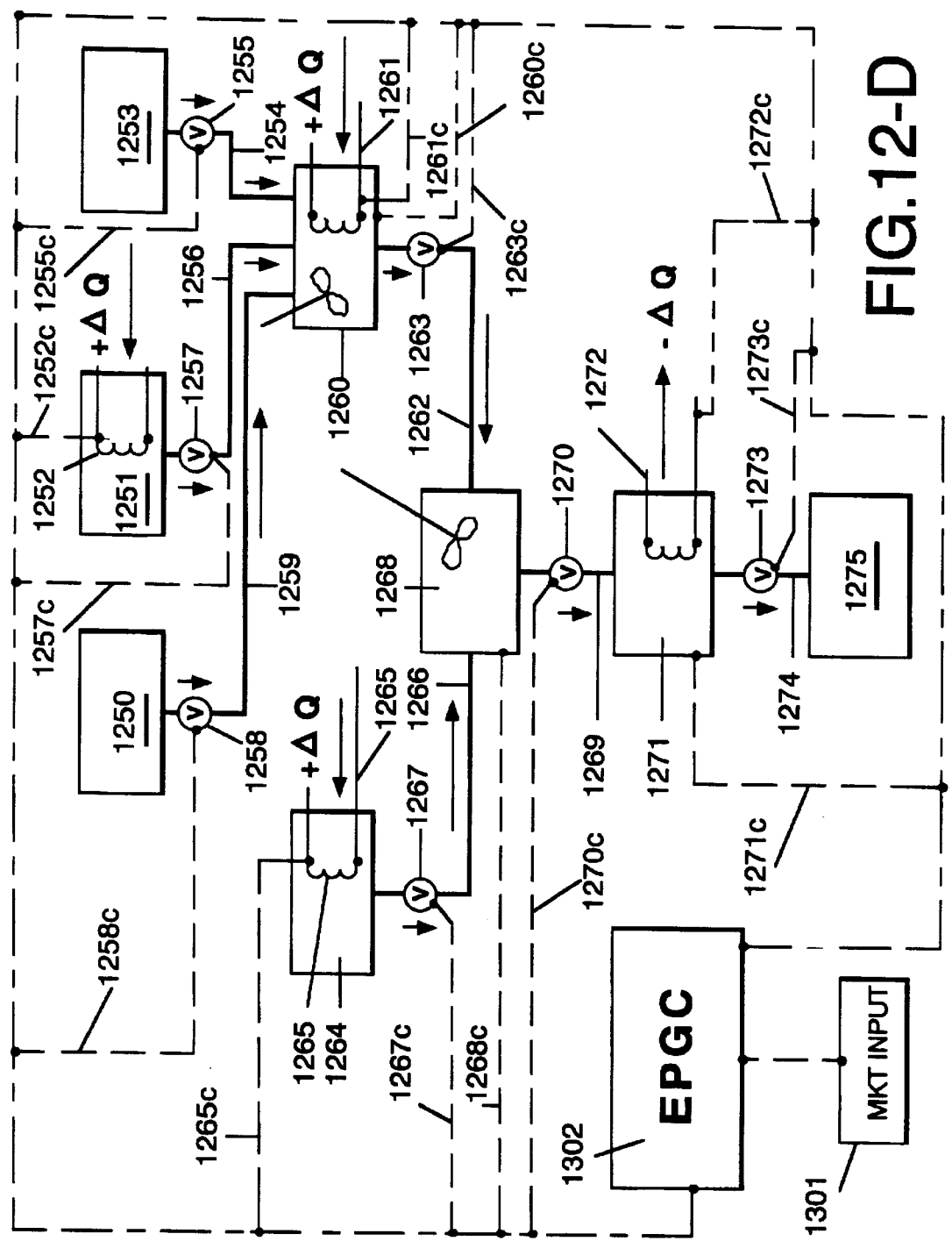
FIG. 12-D

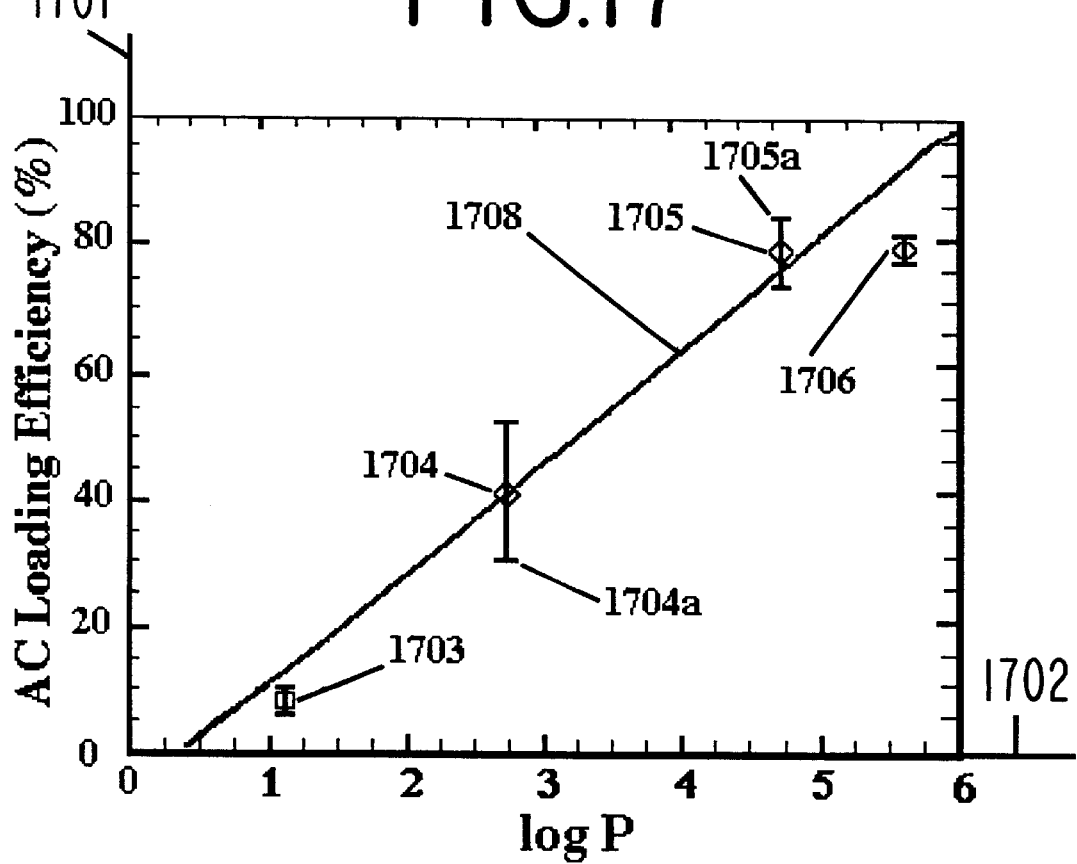

FIG. 18-A
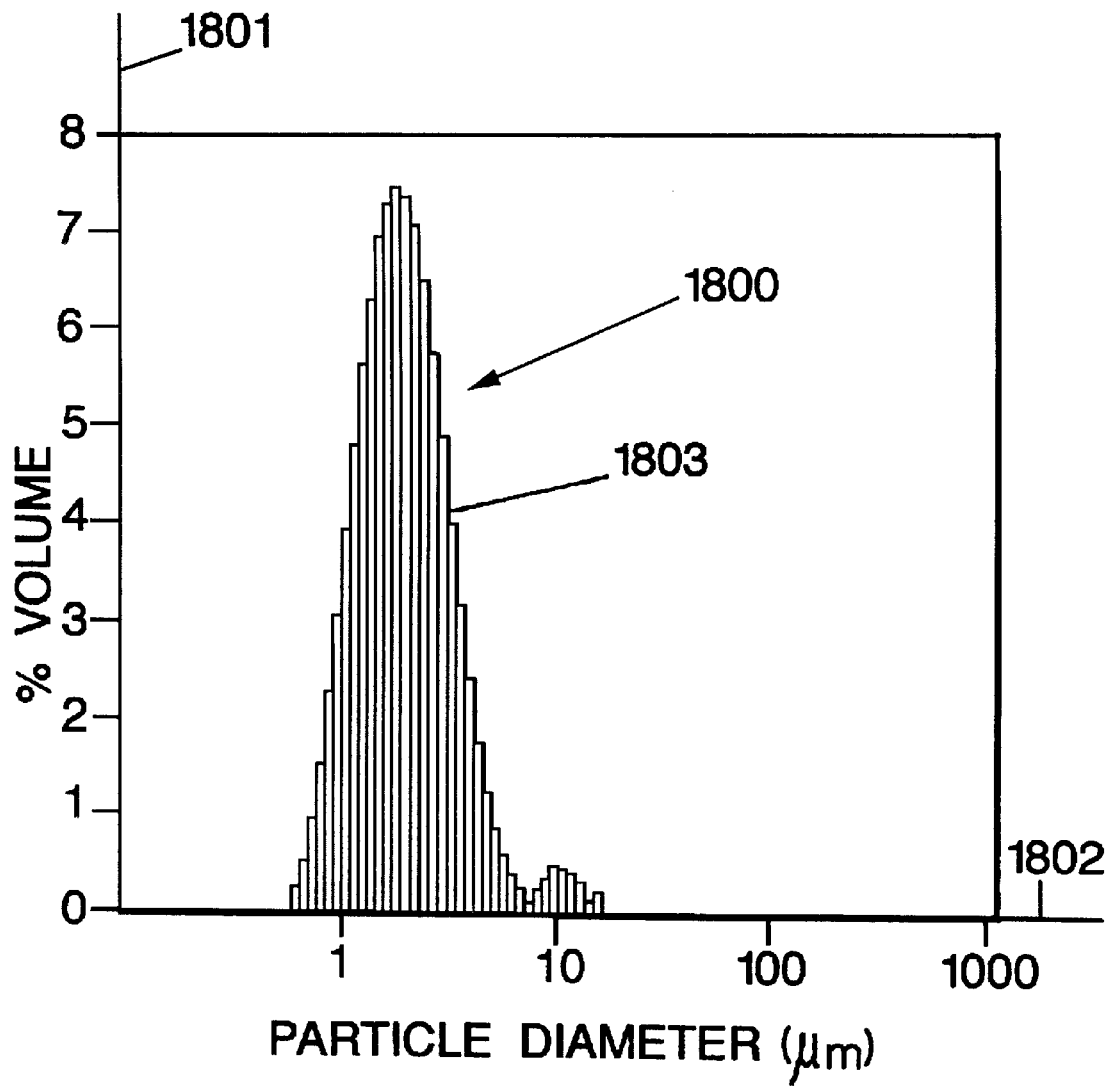

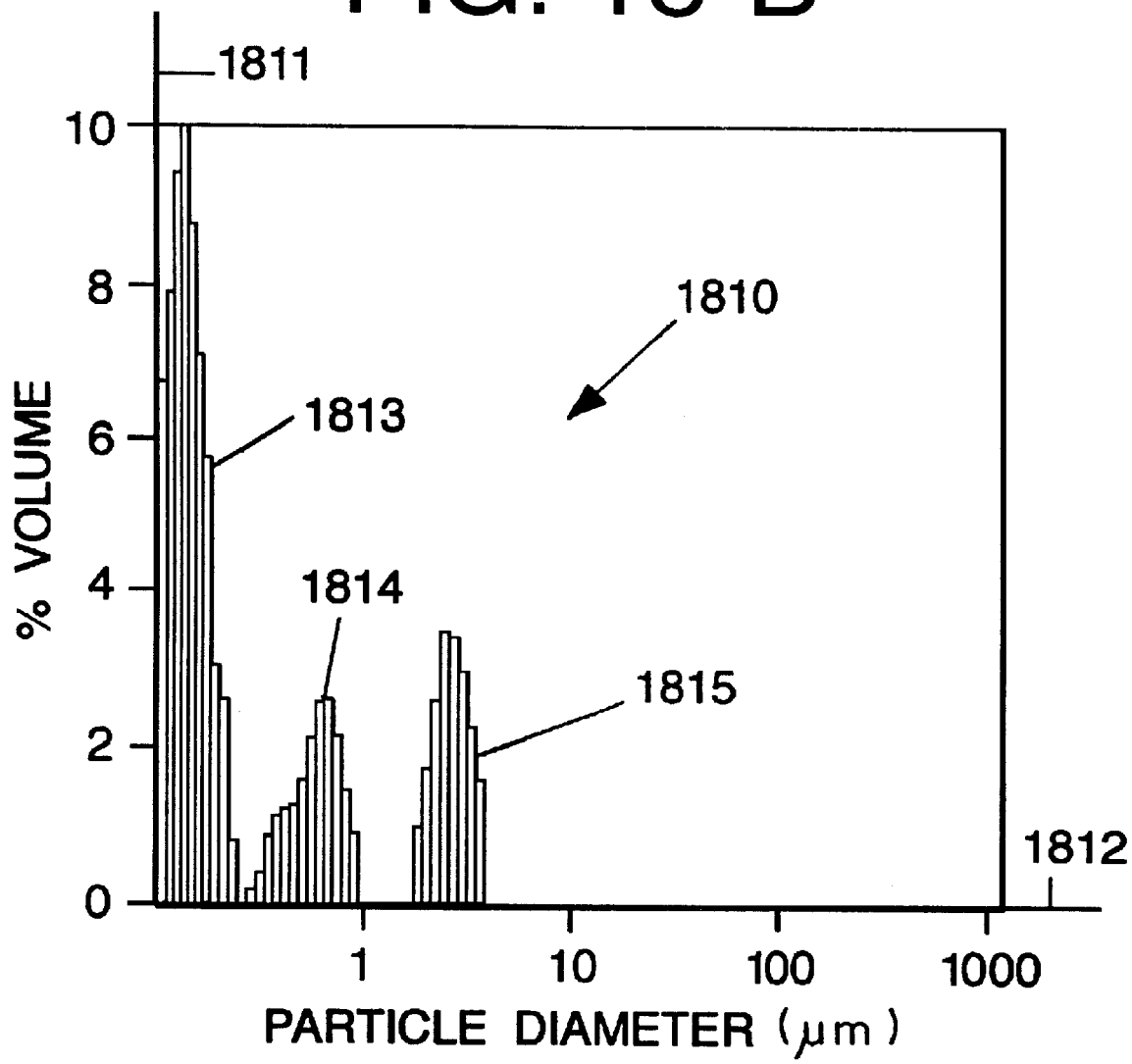
FIG. 18-B

PROCESS FOR TESTING DIFFUSIVITY, ODOR CHARACTER AND ODOR INTENSITY OF A FRAGRANCE MATERIAL AND FRAGRANCE DIFFUSION EVALUATION APPARATUS FOR CARRYING OUT SUCH PROCESS

BACKGROUND OF THE INVENTION

The primary use of air fresheners is to mask odor. A technically advanced air freshener is one that provides longer lasting performance. A need exists for the determination by means of the use of an effective testing system of physical-chemical properties that control the sustained performance of an air freshener fragrance.

It is, accordingly, an object of my invention to devise apparatus and a process for the simultaneous evaluation of an air freshener's performance for its hedonics, intensity, volatile content, diffusivity and weight loss as a function of time in a controlled environment of temperature and air mixing. It is another object of my invention to combine the advantages of a laboratory system that allows for only analytical measurements and a full scale test of odor performance in a specifically designed environment that allows only sensory testing.

Nothing in the prior art provides a system whereby a controlled environment that allows for both sensory and analytical measurements of a fragrance's performance as is the case in my invention.

THE INVENTION

My invention is directed to fragrance diffusion evaluation apparatus for testing the diffusivity, odor character and odor intensity of a fragrance material and a process for using same. The apparatus of my invention includes at least one hollow container having a test sample suspended therein, air flow means for passing air through the inside of the container means and an exit port for the air flow where the intensity and aroma character are measured as a function of time and as a function of temperature. The sample is weighed initially and at time intervals while the air is flowing through the cylinder(s) at a fixed or variable rate.

More specifically, my invention is directed to apparatus located at an X-Y-Z three-space for simultaneously testing the diffusivity, odor character and odor intensity of a fragrance material selected from the group consisting of one or more aroma chemicals and one or more fragrance compositions comprising:

(a) hollow vertically disposed substantially cylindrical container means having:
  (i) a central axis parallel to the Z axis;
  (ii) an inner void;
  (iii) a substantially circular non-interrupted base composed of a first solid nonporous substance located in a first X-Y plane, said base being substantially perpendicular to said Z axis and having an inner void side and an outside;
  (iv) vertically surrounding said inner void and parallel to and substantially equidistant from said Z axis, a continuous cylindrical sidewall composed of a second nonporous substance having an inner void side and an outside, having a top circular rim located in a second X-Y plane, an upper midportion, a lower midportion and a bottom rim located in said first X-Y plane, said bottom rim being fixedly sealed along its entire circumference to the circumference of said base, said sidewall having a first orifice therethrough located in the lower midportion thereof in a third X-Y plane and a second orifice therethrough substantially diametrically opposed to said first orifice located in a fourth X-Y plane, said fourth X-Y plane being located between and substantially parallel to said third X-Y plane and said first X-Y plane, said sidewall otherwise being non-interrupted;
  (v) a top substantially circular cover composed of a third solid nonporous substance and having an inner void side and an outside sealably attached along its entire outer circumference to the circumference of the top circular rim of said sidewall and located in said second X-Y plane, having a substantially circular top cover opening having an inner circumference, said inner circumference being substantially equidistant from said Z axis, said opening having a diameter of from about 20% up to about 40% of the outside diameter of the top cover;

(b) sealably mounted through said first orifice, a temperature probe having a temperature variation-sensitive end attached to support means, said temperature variation-sensitive end being located within said inner void, said support means seabably inserted through said first orifice and connected to temperature monitoring means outside said container means;

(c) sealably mounted through said second orifice, air flow means for supplying a stream of air into said inner void, said air flow means comprising a supply tube having an open end located within said inner void, being connected to said supply tube and located outside said container means, an air supply source; and (d) suspension means for suspending a test sample located within said inner void, said suspension means comprising a substantially flexible support fixedly attached at two substantially diametrically opposed attachment locations located in substantially the same X-Y plane proximate said second X-Y plane, each being proximate the top rim of said sidewall and having attached thereto and suspended therefrom at a location substantially midway between said attachment locations, said test sample initially having absorbed thereon said fragrance material whereby when the air supply means is engaged thereby causing air to flow through said air flow means, and the temperature monitor is engaged, air at a fixed temperature T or a variable temperature $T(\theta)$ will flow at a fixed flow rate Q or a variable flow rate $Q(\theta)$ past said sample having an area A initially holding $G_0$ grams of fragrance materials in a concentration of $C_0$ gram-moles per liter for a period of time $\theta$ at the end of which time said sample will hold $G_1$ grams of fragrance material in a concentration $C_1$ gram-moles per liter during which time $\theta$ the odor character and intensity is capable of being measured and determined proximate the intersection of said Z axis with said second X-Y plane.

My invention is further directed to such apparatus wherein (i) the temperature of the air supplied by the air supply means is controlled and (ii) the temperature probe has programmed feedback means connected to the air supply means.

My invention is further directed to such apparatus wherein the sidewall has a multiplicity of additional orifices at different locations, each of which has sealably mounted therethrough a temperature probe.

Such temperature probes each may have programmed feedback means connected to the air supply means and the temperature of the air supplied by the air supply means is controlled.

My invention is further directed to measurement of the odor character and intensity using an electronic aroma testing device.

My invention is further directed to a process for simultaneously testing the diffusivity, odor character and odor intensity of a fragrance material selected from the group consisting of one or more aroma chemicals and one or more fragrance compositions comprising the steps of:

(a) providing the apparatus as defined above;

(b) suspending a test sample containing a fragrance material in the suspension means of the apparatus described above; and (c) engaging the air supply means and temperature monitor means whereby when the air supply means is engaged to thereby causing air to flow through the air flow means and the temperature monitor is engaged, air at a fixed temperature T or a variable temperature T (θ) will flow at a fixed flow rate Q or a variable flow rate Q(θ) past said sample having an area A initially holding $G_0$ grams of fragrance materials in a concentration of $C_0$ gram-moles per liter for a period of time θ at the end of which time θ said sample will hold $G_1$ grams of fragrance material in a concentration $C_1$ gram-moles per liter during which time θ the odor character and intensity is capable of being measured and determined proximate the intersection of said Z axis with said second X-Y plane.

My invention is further directed to such apparatus as described above wherein the entirety of the inner void side of the base, the sidewall and the top cover is covered with an absorption-preventing substance such as aluminum foil in order to prevent absorption of the fragrance material into the base, the sidewall and the top cover.

My invention is further directed to apparatus consisting of two separate cylinders operated simultaneously in addition to simply using one single cylinder.

My invention is further more specifically directed to apparatus wherein the container means has:

(i) a height of between about 50 and about 75 cm;

(ii) a radius of between about 15 and about 30 cm;

(iii) a volume of between 0.1 and about 0.2 $m^3$;

(iv) a vertical distance of temperature probe to base of between about 10 and about 30 cm;

(v) a vertical distance of air flow means from base being from about 3 up to about 10 cm; and (vi) a diameter of inner opening in top cover being from about 15 up to about 30 cm.

My invention is further directed to the processes described above wherein the internal pressure of the inner void is maintained at from about 0.5 up to about 2 psig and the air flow rate is maintained in the range of from about 900 up to about 1,000 ml per minute.

BRIEF DESCRIPTION OF THE DRAWINGS

FIG. 1A is a diagram of magnified (2,000×) cloth treated by fabric softener without the use of the microparticulate compositions of my invention.

FIG. 1B is a diagram of magnified fabric (2,000×) washed with wax microparticles containing fragrance of my invention.

FIG. 2A is a diagram of a magnified (2,000×) strand of hair washed with shampoo without the use of the microparticulate composition of my invention.

FIG. 2B is a diagram of a magnified (2,000×) strand of hair washed with shampoo containing encapsulated fragrance in wax microparticles of my invention.

FIG. 2C is a diagram of a magnified strand of hair (1,500×) washed with conditioner without the use of the microparticulate composition of my invention.

FIG. 2D is a diagram of a magnified (1,500×) strand of hair washed with conditioner containing the wax microparticles of my invention.

FIG. 3A is a schematic representation of a typical fabric consisting of interwoven bundles which are made up of intertwined fibers. Illustrated is a microparticle entrapped in the pores between the bundles.

FIG. 3B is a schematic representation of a typical fabric consisting of interwoven bundles which are made up of intertwined fibers showing microparticle entrapment in the pores between the bundles as well as direct adhesion through physical forces between a microparticle and a bundle. The microparticles are depicted as black dots.

FIG. 4A is a cutaway side elevation view of apparatus used to carry out the IFF permeation test in order to determine the permeability of fragrances through a given polymer in the presence or in the absence of surfactant.

FIG. 4B is a perspective view of the permeation test (diffusion cell) of FIG. 4A.

FIG. 5A is a graph indicating the permeability of candelilla wax to the aroma chemicals, ethyl tiglate having the structure:

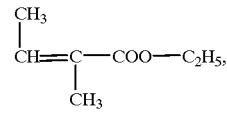

Figure 13:
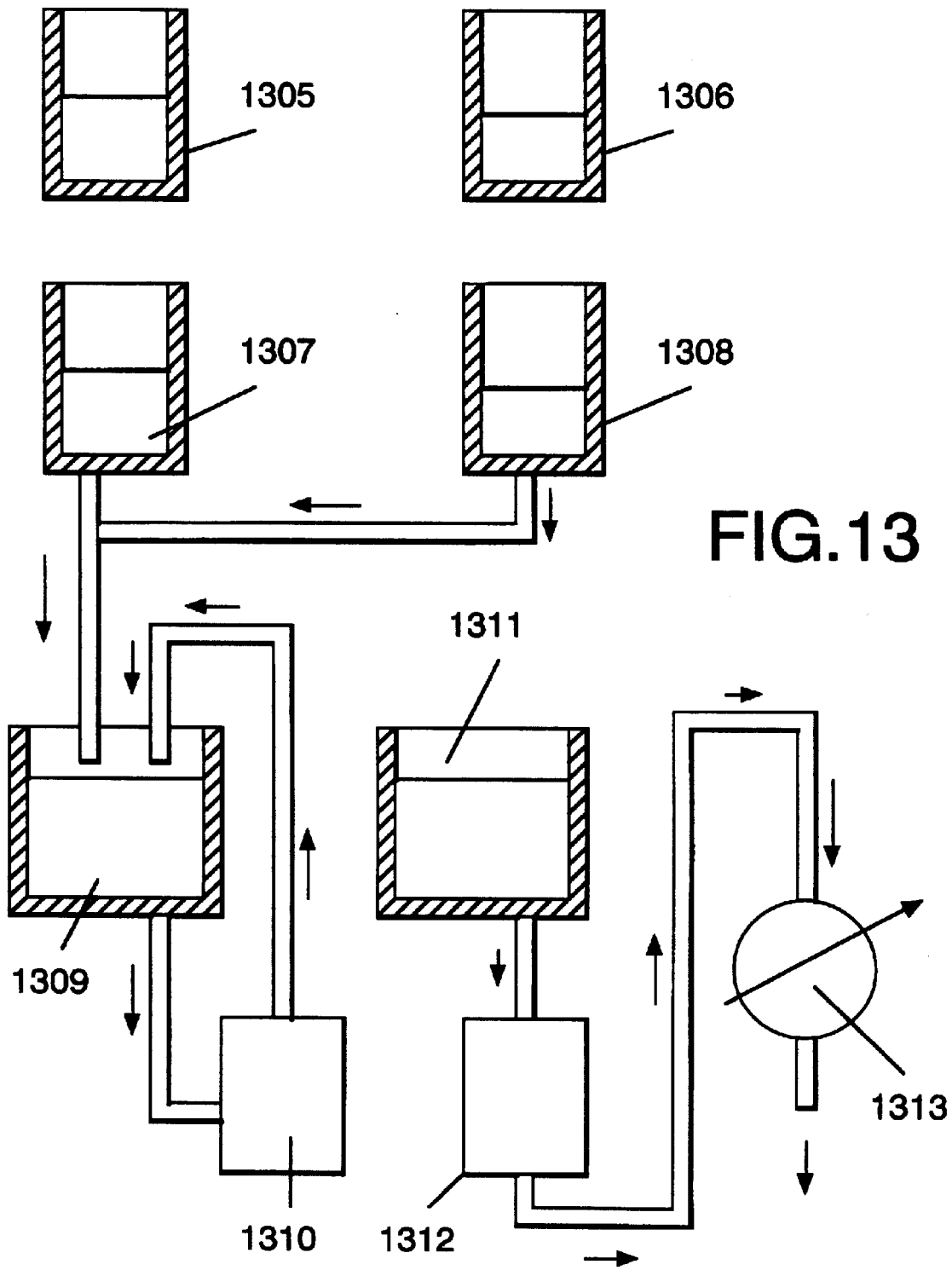

aldehyde C-8 having the structure:

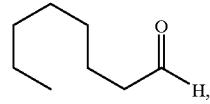

and β-pinene having the structure:

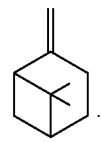

FIG. 5B is another graph showing the permeability of carnauba wax to the aroma chemicals: ethyl tiglate, aldehyde C-8 and β-pinene.

FIG. 5C is another graph showing the permeability of carnauba wax to the aroma chemicals: ethyl tiglate and β-pinene, using non-entrapped ethyl tiglate and β-pinene as controls.

FIG. 5D is a graph showing the permeability of polyethylene wax (molecular weight 500) to the aroma chemicals: ethyl tiglate, aldehyde C-8 and β-pinene determined by the apparatus of FIGS. 4A and 4B.

FIG. 5E is a graph showing the permeability of β-pinene through the waxes: cetyl palmitate (CUTINA® wax), carnauba wax, polyethylene wax (molecular weight 500), candelilla wax and a control.

FIG. 5E(A) is an enlargement of that part of FIG. 5E wherein the weight loss of product tested is between about zero and about $$1\frac{mg-mm}{cm^2}.$$

FIG. 5F is a graph showing the permeability of ethyl tiglate through the waxes: cetyl palmitate (CUTINA® wax), carnauba wax, polyethylene wax, candelilla wax and a control.

FIG. 5G is a graph showing the permeability of hydroxypropyl cellullose to the aroma chemicals: β-pinene and ethyl tiglate and showing the use of a control (without the use of the control release polymer or wax of my invention).

FIG. 5H is a graph showing the permeability of polyvinyl alcohol to the aroma chemicals: ethyl tiglate and β-pinene and also showing the use of a control without the use of the polyvinyl alcohol.

FIG. 6A sets forth a bar graph showing percent geraniol substantivity on cotton fabric swatches for neat geraniol and for geraniol encapsulated in candelilla wax microparticles. The substantivity is plotted on a logarithmic scale.

FIG. 6B sets forth geraniol substantivity on polyester fabric swatches for neat geraniol and for geraniol encapsulated in candelilla wax microparticles. The substantivity is plotted on a logarithmic scale.

FIG. 6C sets forth the substantivity of GALAXOLIDE® (trademark of International Flavors & Fragrances Inc. of New York, N.Y.), a mixture of compounds having the structures:

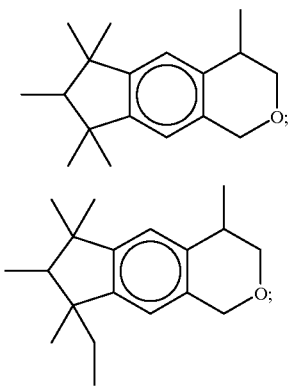

and

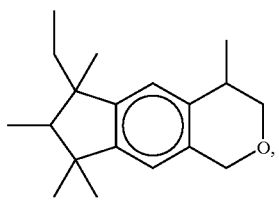

on cotton swatches for the neat GALAXOLIDE® and for GALAXOLIDE® encapsulated in candelilla wax particles.

FIG. 6D sets forth the substantivity of GALAXOLIDE® on polyester fabric swatches for the neat GALAXOLIDE® and for GALAXOLIDE® encapsulated in candelilla wax microparticles.

FIG. 7A is a graph showing the sustained release of GALAXOLIDE® over two days as the neat aroma chemical and when encapsulated in candelilla wax microparticles.

FIG. 7B sets forth a graph showing the release of geraniol having the structure:

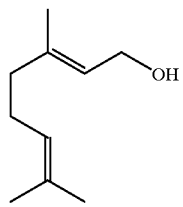

from the microparticle slurry which was applied to brown hair by washing in water. The release from the slurry includes contributions from both the neat and encapsulated aroma chemical, geraniol.

FIG. 8A is a graph showing odor intensity versus time for fragrance S in combination with encapsulated fragrance 361 and fragrance S in combination with unencapsulated fragrance 361.

FIG. 8B is a graph showing odor diffusivity versus time for mixtures of fragrance S with encapsulated fragrance 361 and fragrance S with unencapsulated fragrance 361.

FIG. 8C is a graph showing odor intensity versus time for fragrance S in combination with encapsulated fragrance 885 and fragrance S with unencapsulated fragrance 885.

FIG. 8D is a graph showing odor diffusivity versus time for fragrance S with encapsulated fragrance 885 and fragrance S with unencapsulated fragrance 885.

FIG. 8E is a graph showing odor intensity versus time for fragrance S with encapsulated fragrance 075 and fragrance S with unencapsulated fragrance 075, the encapsulation being in carnauba wax.

FIG. 8F is a graph showing odor diffusivity versus time for fragrance S with encapsulated fragrance 075 and fragrance S with unencapsulated fragrance 075, the encapsulation being in carnauba wax.

FIG. 8G is a graph showing odor intensity versus time for fragrance S and for fragrance S with encapsulated fragrance 361 in carnauba wax.

FIG. 8H is a graph showing odor diffusivity versus time for fragrance S alone and for fragrance S in combination with encapsulated fragrance 361 in carnauba wax.

FIG. 8I is a graph showing odor intensity versus time for fragrance S and for fragrance S in combination with encapsulated fragrance 885 in carnauba wax.

FIG. 8J is a graph showing odor diffusivity versus time for fragrance S alone and for fragrance S in combination with encapsulated fragrance 885 in carnauba wax.

FIG. 8K is a graph showing odor intensity versus time for fragrance S taken alone and for fragrance S in combination with encapsulated fragrance 075.

FIG. 8L is a graph showing odor diffusivity versus time for fragrance S taken alone and for fragrance S in combination with encapsulated fragrance 075 in carnauba wax.

FIG. 9A is a schematic diagram of a cutaway side elevation view of a microparticle of my invention showing substantially hydrophilic surfactant substantially entirely coated and fixedly bonded to the entirety of the outer surface of a single phase solid solution in the form of a continuous submicron layer of surfactant.

FIG. 9B shows a solid solution-microparticle of my invention wherein the substantially hydrophilic surfactant is located proximate to and immediately, substantially beneath the entirety of the outer surface of the solid solution and substantially within the internal matrix volume.

FIG. 9C shows a particle of my invention wherein the substantially hydrophilic surfactant is both (a) substantially entirely coated on and fixedly bonded to the entirety of said outer surface of said single phase solid solution in the form of a continuous submicron layer of surfactant and (b) located proximate to and immediately, substantially beneath the entirety of said outer surface of said solid solution and substantially within said internal matrix volume.

FIG. 10A is a schematic diagram showing the side view of a diffusivity testing apparatus for testing the diffusivity of entrapped and nonentrapped fragrance materials including aroma chemicals and fragrance compositions.

FIG. 10B is the top view of the apparatus of FIG. 10A.

FIG. 11A is a schematic perspective view of the first stage of the operation of a rotor/stator high shear mixer, wherein the high speed rotation of the rotor blades within the precision machined mixing workhead exerts a powerful suction drawing liquid and solid materials into the rotor/stator assembly.

FIG. 11B is a schematic perspective diagram of stage two of the operation of a rotor/stator high shear mixer used in the processes and apparatus of my invention where centrifical force drives materials towards the periphery of the workhead where they are subjected to a milling action in the precision machined clearance between the ends of the rotor blades and the inner wall of the stator.

FIG. 11C is a schematic perspective diagram of the operation of the third stage of a rotor/stator high shear mixer useful in the apparatus of my invention and in carrying out the processes of my invention, wherein the second stage is followed by intense hydraulic shear as the materials are forced, at high velocity, out through the perforations in the stator, then through the machine outlet and along the pipework; while at the same time, fresh materials are continually drawn into the workhead, maintaining the mixing and pumping cycle.

FIG. 11D is a schematic side view of the homogenizing equipment assembly for carrying out the blending step of the processes of my invention and as part of the apparatus of my invention.

FIG. 11E is a schematic cutaway, side elevation view of a single-stage homogenizing valve assembly for the homogenizing part of the apparatus of my invention.

FIG. 11F is a cutaway side elevation view of a two-stage homogenizing valve assembly for the homogenizing apparatus for the blending step of the processes of my invention and for the apparatus of my invention.

FIG. 11G is a schematic side elevation view of a rotor/stator mixing assembly useful in the apparatus of my invention and in carrying out the blending step of the processes of my invention.

FIG. 12A sets forth a block flow diagram showing the process steps of my invention in preparing particulate compositions of my invention. FIG. 12A also shows in schematic form the apparatus of my invention.

FIG. 12B is a schematic block flow diagram setting forth the process steps of my invention for the process useful in preparing the compositions of my invention. FIG. 12B also sets forth in schematic form the apparatus of my invention.

FIG. 12C shows a schematic diagram of the apparatus and process steps of FIG. 12A with an additional schematic representation of the utilization of an electronic program controller (e.g., computer system) whereby market demand information and the like can be utilized to cause automatic alterations in the process variables of the process of my invention where ingredients are admixed, blended, heated and cooled.

FIG. 12D shows a schematic diagram of the apparatus of FIG. 12B with an additional schematic representation of the utilization of an electronic program controller (e.g., computer system) whereby market demand information and the like can be utilized to cause automatic alterations and adjustments in the process variables (e.g. blending, heating, ratio of ingredients and cooling as well as flow rates) in the process of my invention and in the apparatus of my invention.

FIG. 13 is a schematic flow diagram showing the processing in schematic form of wax microparticles containing active or bioactive ingredients of my invention.

Figure 14:
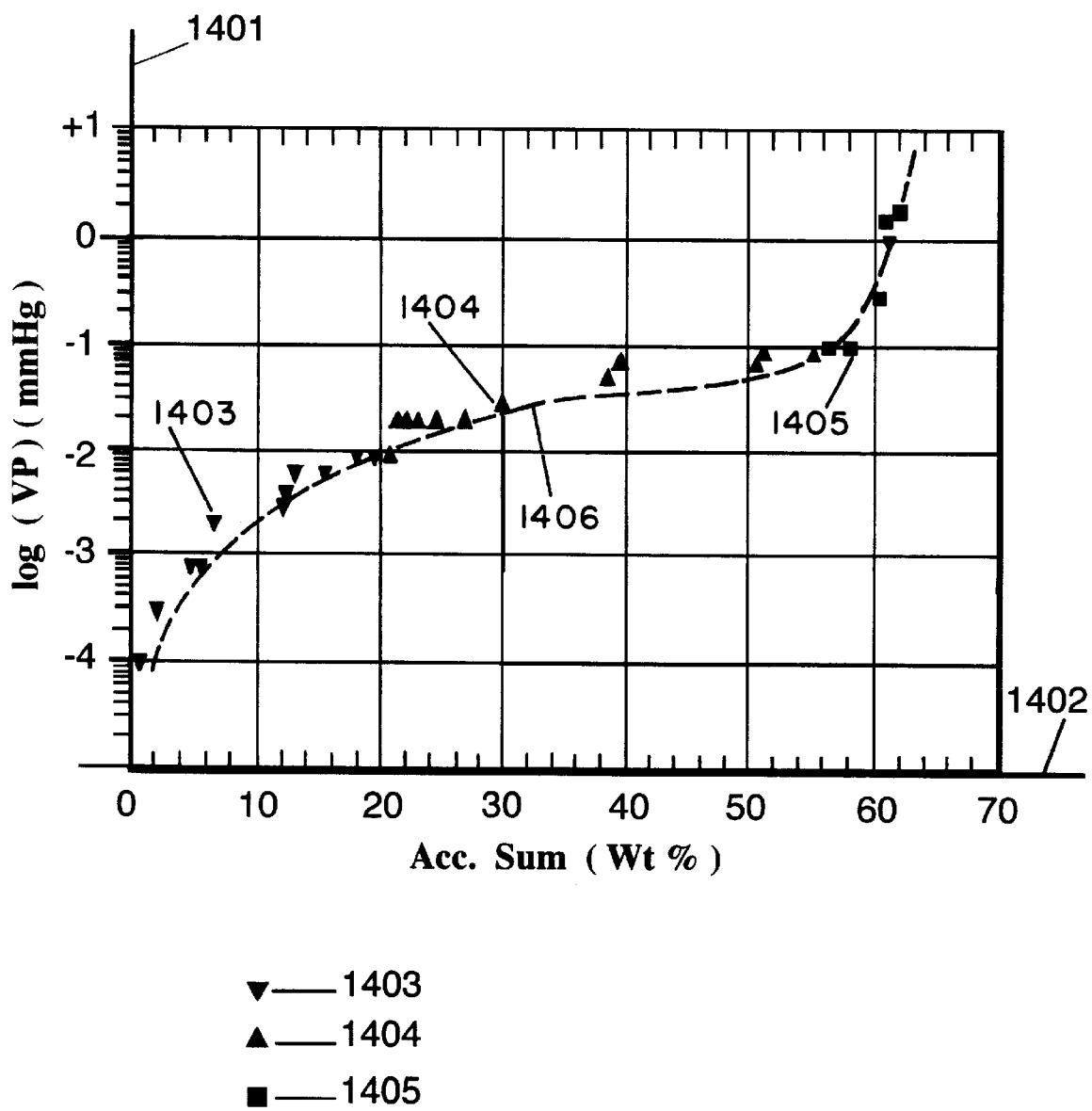

FIG. 14 is a graph showing log vapor pressure versus accumulated sum of fragrance ingredients for three different fragrances: fragrance A-1, fragrance A-2 and fragrance A-3. Each of the fragrances falls within the same graph.

Figure 15:
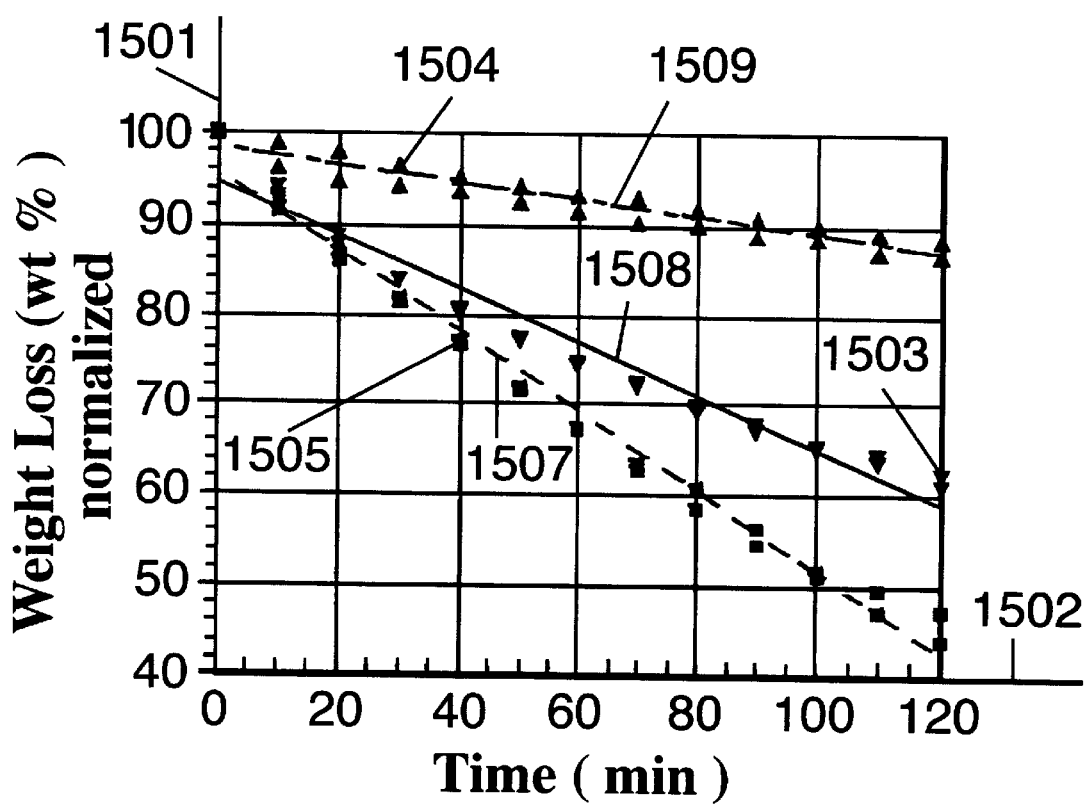

FIG. 15 is a graph showing weight loss (weight percent) normalized versus time for three different groups of ingredients: low vapor pressure materials, high vapor materials and mixtures of low and high vapor pressure materials.

Figure 16:
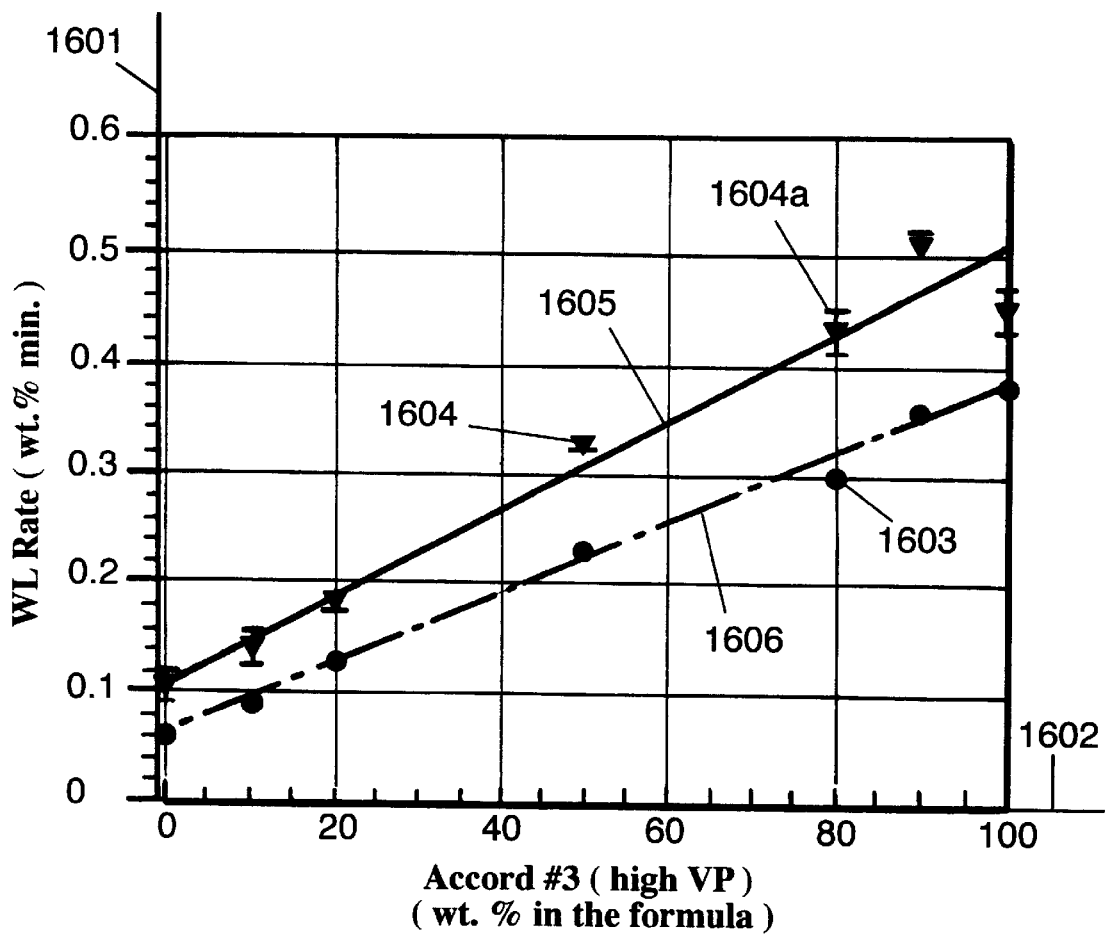

FIG. 16 is a graph showing weight loss rate (weight percent per minute) versus weight percent in the formula of fragrance A-3, a high vapor pressure fragrance, for both the fragrance diffusion evaluation system (as set forth in FIGS. 10A and 10 B) and for the prior art thermal gravimetric analysis system.

FIG. 17 is a graph showing aroma chemical loading efficiencies for the chemicals: benzyl alcohol, geraniol, farnesol having the structure:

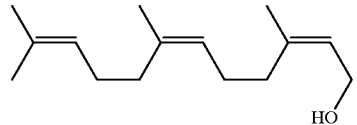

and GALAXOLIDE® (registered trademark of International Flavors & Fragrances Inc.) versus $\log_{10}P$ wherein P is the octanol-water partition coefficient for the aroma chemicals. The microparticles which are the subject of this graph are candelilla wax microparticles.

FIG. 18A sets forth a particle-size distribution for particles evolving out of the rotor/stator mixer using a composition containing 1.2% cetyl trimethyl ammonium chloride having the structure:

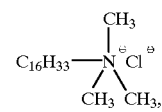

10% candelilla wax and 10% fragrance P-50448. The graph shows volume percent versus particle diameter.

FIG. 18B is a graph of volume percent versus particle diameter for particles evolving out of the homogenizer blending apparatus, which particles contain 5% cetyl trimethyl ammonium chloride, 10% candelilla wax and 10% fragrance IB-X-016.

Figure 19:
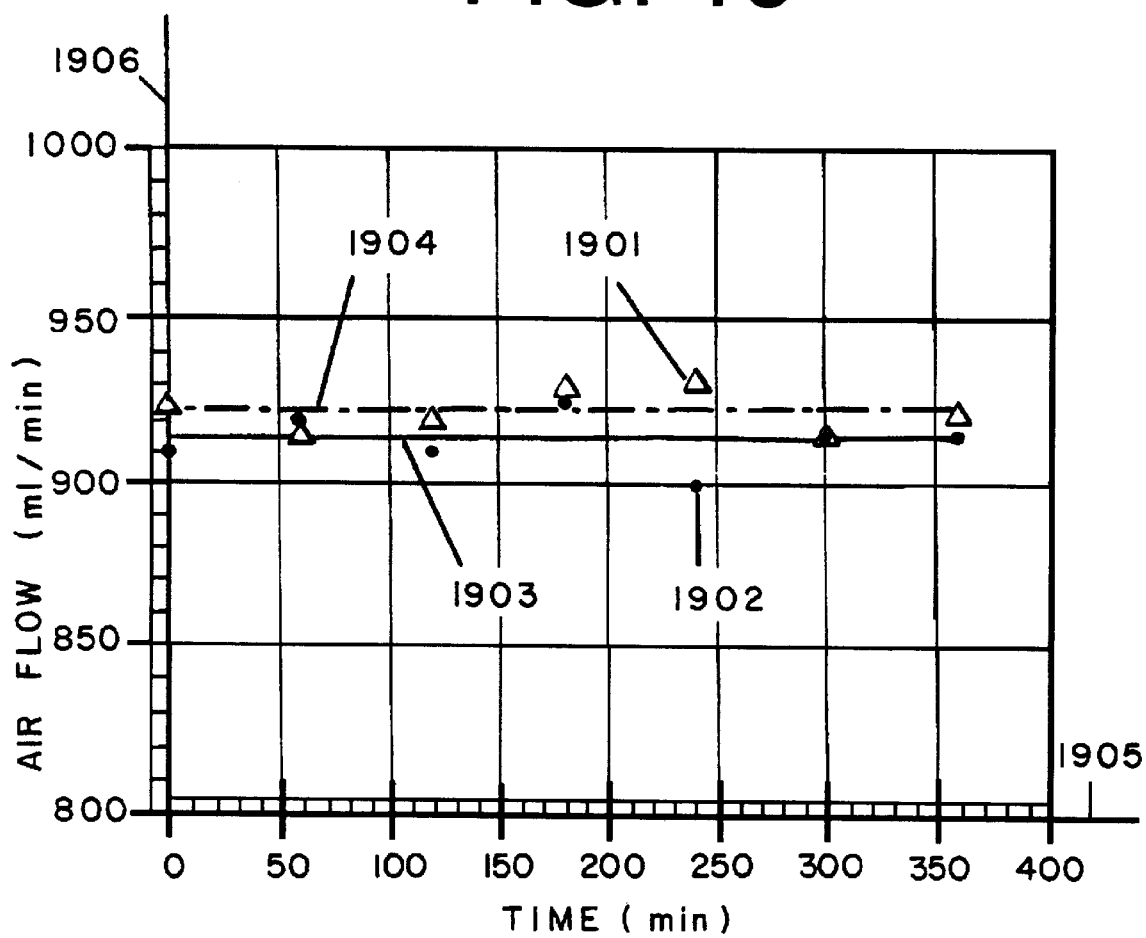

FIG. 19 is a graph of air flow (ml/minute) versus time (minute) showing a system of my invention using two cylinders as set forth in FIG. 10B described, supra, and described in detail, infra, with the two cylinders being connected in parallel.

DETAILED DESCRIPTION OF THE DRAWINGS

Referring to FIG. 1A, reference numeral 10 indicates the fiber itself and reference numeral 11 indicates the space between the fibers.

Referring to FIG. 1B and Figure reference numeral 12 refers to the wax microparticles located on the surface of the fabric.

Referring to FIG. 2A and Figure reference numeral 20 refers to the hair strand itself.

Referring to FIG. 2B and reference numeral 21 refers to the wax microparticles located on the surface of the hair strands.

Referring to FIG. 2C and reference numeral 23 refers to the strand of hair washed with a conditioner.

Referring to FIG. 2D and reference numeral 24 refers to the wax microparticles located on the surface of the hair strands.

Referring to FIG. 3A, the bundles of fibers are referred to by reference numerals 30a and 30b. The microparticle entrapped in the pores between the bundles is referred to by reference numeral 32. The space between the bundles is referred to by reference numeral 31. FIG. 3A is an enlargement of section 3A of FIG. 3B.

Referring to FIG. 3B, the fiber bundles are shown by reference numeral 33. The microparticle entrapped between the bundles is shown by reference numeral 36, being entrapped in space 37. The fiber bundles are shown by reference numerals 33a and 33b and, in addition, reference numerals 34 and 34b. The microparticle directly adhered through physical forces onto a bundle is shown by reference numeral 35.

Referring to FIGS. 4A and 4 B, fluid 46 is located in jar 44. Jar 44 has sidearm 45. The fluid 46 reaches fluid level 47. Directly in line with fluid level 47 is membrane 41. The diffusion membrane 41 is held in place with flanges 43 and jar lip 42, using bolts 401a and 401b which secures the flange in place. The sidearm 45 is closed using closure 49. The permeability apparatus is shown using reference numeral 40. The IFF permeability test is based on the use of the apparatus of FIGS. 4A and 4 B. The weight of membrane 41 is taken, initially, before being placed within the flange 43 and the jar lip 42. Substance 46 for which the permeability is to be measured is placed into jar 44 to fluid level 47. The apparatus containing fluid 46 remains in place for a fixed period of time. At the end of that period of time, bolts 401a and 401b as well as 401c are loosened, the flange 43 removed and membrane 41 is removed and weighed, thereby gathering sufficient data to determine the permeability of the particular substance 46. Referring to FIG. 5A, reference numeral 52 are data points for aldehyde C-8. Reference numeral 53 shows data points for ethyl tiglate. The Y axis measures weight loss and is indicated by reference numeral 54. The X axis shows time in minutes and is indicated by reference numeral 55. The weight loss is measured in $$\frac{mg-mm}{cm^2}.$$

Reference numeral 51 shows the standard deviation for the data.

In FIG. 5B, reference numeral 503 represents data points for aldehyde C-8. Reference numeral 502 represents data points for β-pinene. Reference numeral 58 represents data points for ethyl tiglate. Reference numeral 501 shows the graph for weight loss versus time for ethyl tiglate, thus showing the permeability of carnauba wax to ethyl tiglate. The Y axis for weight loss is indicated by reference numeral 56, and the X axis for time is indicated by reference numeral 57. Reference numeral 59 sets forth the standard deviation for the data for ethyl tiglate.

Referring to FIG. 5C, reference numeral 507 is for ethyl tiglate, encapsulated. Reference numeral 508 is for the graph of ethyl tiglate for weight loss versus time, showing the permeability of carnauba wax to ethyl tiglate. Reference numeral 506 shows the data points for β-pinene in carnauba wax. Reference numeral 510 shows data points for ethyl tiglate without being entrapped in any control release system such as carnauba wax. Reference numeral 509 shows data points for the β-pinene control in the absence of carnauba wax. Reference numeral 511 sets forth the graph of unentrapped ethyl tiglate. Reference numeral 512 sets forth the graph of unentrapped β-pinene. The Y axis showing weight loss is indicated by reference numeral 505. The X axis showing time in minutes is indicated by reference numeral 504.

Referring to FIG. 5D, reference numeral 515 sets forth the data points for ethyl tiglate in the polyethylene (molecular weight 500) wax. Reference numeral 520 is for the graph of time versus weight loss. Reference numeral 516 shows data points for aldehyde C-8 in polyethylene wax. Reference numeral 517 shows data points for β-pinene in polyethylene wax. Reference numeral 519 indicates the graph for aldehyde C-8 in polyethylene wax, showing the permeability of aldehyde C-8 through polyethylene wax. Reference numeral 520 shows the graph for ethyl tiglate in polyethylene wax showing the permeability of ethyl tiglate through polyethylene wax. The X axis is indicated by reference numeral 513, and the Y axis is indicated by reference numeral 514.

Referring to FIG. 5E, reference numeral 528 refers to cetyl palmitate (CUTINA® wax). Reference numeral 527 refers to data points for carnauba wax. Reference numeral 526 refers to data points for polyethylene wax. Reference numeral 525 refers to data points for candelilla wax. Reference numeral 523 refers to the control for β-pinene without wax. All data points set forth on FIG. 5E, except for the control, show the permeability of β-pinene through waxes. The X axis is indicated by reference numeral 521, showing time and minutes, and the Y axis is indicated by reference numeral 522, showing weight loss in $$\frac{mg-mm}{cm^2}.$$

FIG. 5E(A) shows that portion of FIG. 5E where the weight loss is between zero and 1.4 for the β-pinene contained in the waxes. In FIG. 5E(A), reference numeral 533 shows the standard deviation line. The X axis is indicated by reference numeral 521, and the Y axis is indicated by reference numeral 522 for weight loss. Reference numeral 528 shows data points for cetyl palmitate. Reference numeral 526 shows data points for polyethylene wax (molecular weight 500). Reference numeral 530 sets forth the graph for time versus weight loss for polyethylene wax containing β-pinene. Reference numeral 533a is the standard deviation line for the data points for polyethylene wax containing β-pinene. Reference numeral 529 shows the graph for carnauba wax containing β-pinene and sets forth the permeability of β-pinene through carnauba wax.

Referring to FIG. 5F, reference numeral 538 shows the data points for cetyl palmitate (CUTINA® wax). Reference numeral 540 shows data points for carnauba wax. Reference numeral 541 shows data points for polyethylene (molecular weight 500) wax. Reference numeral 542 shows data points for candelilla wax. Reference numeral 537 shows data points for the control, ethyl tiglate without wax. Reference numeral 536 is the graph showing the evaporation rate for the control, ethyl tiglate without wax. Reference numeral 539 is the graph showing permeability of ethyl tiglate through cetyl palmitate (CUTINA® wax). Reference numeral 543 sets forth the graph showing permeability of ethyl tiglate through carnauba wax. The X axis is indicated by reference numeral 534 for time (minutes). The Y axis is indicated by reference numeral 535 for weight loss $$\left(\frac{mg - mm}{cm^2}\right).$$

Referring to FIG. 5G, reference numeral 562 indicates data points for β-pinene contained in hydroxypropyl cellulose. Reference numeral 564 indicates data points for β-pinene not contained in any polymer, but merely showing the evaporation rate of the β-pinene. Reference numeral 569 shows the standard deviation for the data points for β-pinene without being contained in hydroxypropyl cellulose. Reference numeral 563 shows the data points for ethyl tiglate contained in hydroxypropyl cellulose. Reference numeral 565 sets forth the data points for ethyl tiglate not being contained in any polymer and showing the evaporation rate of ethyl tiglate. Reference numeral 567 sets forth the graph showing the permeability of ethyl tiglate through hydroxypropyl cellulose. Reference numeral 568 sets forth the graph showing the evaporation of ethyl tiglate (without being contained in any polymer). Reference numeral 566 sets forth the graph showing the evaporation of β-pinene without being present in any polymer. The X axis is indicated by reference numeral 561 showing time in minutes, and the Y axis is indicated by reference numeral 560 showing weight loss in mg–mm/cm².

Referring to FIG. 5H, reference numeral 552 shows the data points for ethyl tiglate contained in polyvinyl alcohol. Reference numeral 553 sets forth the data points for β-pinene contained in polyvinyl alcohol (99% hydrolyzed polyvinyl acetate). Reference numeral 554 sets forth the data points for ethyl tiglate not contained in polyvinyl alcohol and merely shows the evaporation rate of the ethyl tiglate. Reference numeral 555 sets forth the data points for β-pinene not being contained in any polyvinyl alcohol, but merely showing the evaporation rate of the β-pinene. Reference numeral 557 sets forth the graph showing the evaporation rate of β-pinene not being contained in any polyvinyl alcohol. Reference numeral 559 sets forth the standard deviation for the data points for ethyl tiglate and β-pinene not being contained in any polyvinyl alcohol. The X axis for time (minutes) is shown by reference numeral 551. The Y axis for weight loss $$\left(\frac{mg - mm}{cm^2}\right)$$

is shown by reference numeral 560.

Referring to FIG. 6A, percent substantivity is shown on the Y axis by reference numeral 60. The bar graph for neat geraniol using a plain water wash is shown by reference numeral 61a. The bar graph for geraniol contained in candelilla wax microparticles is shown by reference numeral 61b for a plain water wash. The bar graph for neat geraniol using a detergent is shown by reference numeral 62a. The bar graph for neat geraniol in candelilla wax microparticles is shown by reference numeral 62b for detergents. The bar graph for fabric softeners for neat geraniol is shown by reference numeral 63a. The bar graph for geraniol contained in candelilla wax microparticles in fabric softeners is shown by reference numeral 63b.

Referring to FIG. 6B, substantivity (percent) is shown on the Y axis indicated by reference numeral 64. Reference numeral 65a sets forth the substantivity of neat geraniol in a plain water wash on polyester fabric. Reference numeral 65a' sets forth the standard deviation line for the neat geraniol in a plain water wash. Reference numeral 65b sets forth the use of neat geraniol encapsulated in candelilla wax microparticles for a plain water wash. Reference numeral 65b' sets forth the standard deviation line for the encapsulated geraniol in candelilla wax using a plain water wash. Reference numeral 66a sets forth the use of neat geraniol in a detergent on polyester fabrics. Reference numeral 66b sets forth the use of geraniol encapsulated in candelilla wax microparticles used in a detergent. Reference numeral 67a sets forth the use of neat geraniol in a fabric softener on polyester fabrics. Reference numeral 67b sets forth the use of geraniol encapsulated in candelilla wax microparticles used in a fabric softener on polyester fabrics.

Referring to FIG. 6C, the Y axis shows substantivity in terms of percentages and is shown by reference numeral 601. Reference numeral 602a sets forth the use of neat GALAXOLIDE® in a detergent on cotton fabric. Reference numeral 602b sets forth the use of GALAXOLIDE® encapsulated in candelilla wax microparticles on cotton fabrics in a detergent. Reference numeral 603a sets forth the use of neat GALAXOLIDE® in a fabric softener on cotton fabrics. Reference numeral 603b sets for th the use of GALAXOLIDE® encapsulated in candelilla wax microparticles in fabric softener on cotton fabrics.

Referring to FIG. 6D, substantivity (percent) is set forth on the Y axis using reference numeral 604. In FIG. 6D, reference numeral 605a refers to the use of neat GALAXOLDE® in a detergent on polyester fabrics. Reference numeral 605b refers to the use of GALAXOLIDE® encapsulated in candelilla wax microparticles in a detergent for use on polyester fabrics. Reference numeral 605b' refers to the standard deviation for the use of GALAXOLIDE® encapsulated in candelilla wax microparticles with a detergent on polyester fabrics. Reference numeral 606a refers to the use of neat GALAXOLIDE® in a fabric softener on polyester fabrics. Reference numeral 606a' refers to the standard deviation of the data of neat GALAXOLIDE® in a fabric softener for use on polyester fabrics. Reference numeral 606b refers to the use of GALAXOLIDE® encapsulated in candelilla wax microparticles in a fabric softener for use on polyester fabrics. Reference numeral 606b' refers to the standard deviation of the data for GALAXOLIDE® encapsulated in candelilla wax microparticles for use with a fabric softener on polyester fabrics.

Referring to FIG. 7A, showing the sustained release of GALAXOLIDE® over a period of two days as the neat aroma chemical and when encapsulated in candelilla wax microparticles. Reference numeral 70 indicates the Y axis. Reference numeral 71 indicates the X axis in time in days. Reference numeral 72 sets forth the graph for the use of the neat GALAXOLIDE®. Reference numeral 72' sets forth the data points for the neat GALAXOLIDE®. Reference numeral 73 sets forth the graph for the GALAXOLIDE® contained in the candelilla wax microparticles. Reference numeral 703 sets forth the data points for the GALAXOLIDE® encapsulated in candelilla wax microparticles. Reference numeral 704 sets forth the standard deviation for the data points for GALAXOLIDE® encapsulated in candelilla wax microparticles.

Referring to FIG. 7B, reference numeral 74 refers to the Y axis which refers to the percent of aroma chemical (geraniol) remaining on brown hair, and reference numeral 75 refers to the X axis indicating time of release in days. Reference numeral 76 sets forth the graph showing the rate of release of neat geraniol. Reference numeral 701 sets forth the data points for the neat geraniol. Reference numeral 702 sets forth the standard deviation for the data points for the neat geraniol. Reference numeral 77 sets forth the graph for the rate of release of geraniol encapsulated in candelilla wax microparticles. Reference numeral 79 sets forth the data points for geraniol encapsulated in candelilla wax microparticles. Reference numeral 78 sets forth the standard deviation for the data points for geraniol encapsulated in candelilla wax microparticles.

Referring to FIG. 8A, the Y axis indicating odor intensity on a scale of 1–10 is indicated by reference numeral 80. The X axis indicating time in hours is indicated by reference numeral 81. Reference numeral 82 refers to the graph of odor intensity versus time for fragrance S in combination with encapsulated fragrance 361. Reference numeral 83 refers to the graph of odor intensity versus time for the combination of fragrance S and encapsulated fragrance 361.

Referring to FIG. 8B, the Y axis is indicated by reference numeral 84 for odor diffusivity on a scale of 1–10. The X axis is indicated by reference numeral 85 for time in hours. Reference numeral 86 indicates the graph of odor diffusivity versus time for fragrance S in combination with encapsulated fragrance 361. Reference numeral 87 indicates the graph of odor diffusivity versus time for fragrance S in combination with unencapsulated fragrance 361.

Referring to FIG. 8C, reference numeral 801 indicates the graph of odor intensity versus time for fragrance S and encapsulated fragrance 885. Reference numeral 802 indicates the graph of odor intensity versus time for fragrance S and unencapsulated fragrance 885.

Referring to FIG. 8D, reference numeral 803 shows the graph of odor diffusivity versus time for fragrance S and encapsulated fragrance 885. Reference numeral 804 indicates the graph for odor diffusivity versus time for fragrance S in combination with unencapsulated fragrance 885.

Referring to FIG. 8E, reference numeral 805 indicates the graph of odor intensity versus time for fragrance S and encapsulated fragrance 075. Reference numeral 806 sets forth the graph of odor intensity versus time for fragrance S and unencapsulated fragrance 075.

Referring to FIG. 8F, reference numeral 807 shows the graph of odor diffusivity versus time for fragrance S and encapsulated fragrance 075. Reference numeral 808 sets forth the graph of odor diffusivity versus time for fragrance S and unencapsulated fragrance 075. These graphs suggest that the carrier retains the topnotes during storage and adheres to the hair.

Referring to FIG. 8G, reference numeral 809 sets forth the graph for odor intensity versus time for fragrance S taken alone. Reference numeral 810 sets forth the graph of odor intensity versus time for fragance S taken together with encapsulated fragrance 361.

Referring to FIG. 8H, reference numeral 811 sets forth the graph of odor diffusivity versus time for fragance S taken alone. Reference numeral 812 sets forth the graph of odor diffusivity versus time for fragrance S taken in combination with encapsulated fragrance 361. The system containing the encapsulated fragrance clearly provides an advantage over the neat oil. The observed difference in intensity between these systems is large enough to provide a perceived difference.

Referring to FIG. 8I, the graph indicated by reference numeral 813 is for the odor intensity versus time for fragrance S taken alone. The graph indicated by reference numeral 814 is for odor intensity versus time for fragrance S taken together with encapsulated fragrance 885.

Referring to FIG. 8J, the graph indicated by reference numeral 815 is for odor diffusivity versus time for fragrance S taken alone. The graph indicated by reference numeral 816 is for odor diffusivity versus time for fragrance S taken together with encapsulated fragrance 885.

Referring to FIG. 8K, the graph indicated by reference numeral 817 is for odor intensity versus time for fragrance S taken alone. The graph indicated by reference numeral 818 is for odor intensity versus time for fragrance S taken together with encapsulated fragrance 075.

Referring to FIG. 8L, the graph indicated by reference numeral 819 is for odor diffusivity versus time for fragrance S taken alone. The graph indicated by reference numeral 820 is for odor diffusivity versus time for fragrance S taken together with encapsulated fragrance 075. These graphs show that the volume and the tenacity of encapsulated fragrance 075 is higher than that of fragrance S taken alone up to 5 hours. The encapsulation system may be used to increase substantivity.

Referring to FIG. 9A, the substantially hydrophilic surfactant 93 is substantially, entirely coated on and fixedly bonded to the entirety of the outer surface 95 of the single phase solid solution 91 in the form of a continuous submicron layer of surfactant 92. The particle having surfactant coated thereon in a submicron layer is indicated by reference numeral 90.

Referring to FIG. 9B, the substantially hydrophilic surfactant 903 is located proximate to and immediately substantially beneath the entirety of the outer surface 905 of the solid solution 901 and substantially within the internal matrix volume. The charge on the particle is shown using reference numeral 904, and the particle itself is shown by reference numeral by reference numeral 900.

Referring to FIG. 9C, the substantially hydrophilic surfactant 917/913 is both (a) substantially, entirely coated on and fixedly bonded to the entirety of the outer surface 915 of the single phase solid solution 911 in the form of a continuous submicron layer of surfactant 912 and (b) located proximate to and immediately, substantially beneath the entirety of the outer surface of said solid solution 915 and substantially within the internal matrix volume. The surfactant within the matrix volume is indicated by reference numeral 917. The surfactant within the submicron layer is indicated by reference numeral 913. The particle is indicated by reference numeral 910. The charge on the outer surface 916, the particle, is indicated by reference numeral 914.

FIGS. 10A and 10B set forth the fragrance diffusion evaluation system for determining the diffusivity and permeability of fragrance materials and other active and bioactive ingredients used in the practice of my invention. The test sample on blotters indicated by reference numeral 1001 are supported by support 1002 in container 1003 having opening 1004 to the atmosphere. Air flow through line 1010 is supplied from air supply 1005 through tube 1006, having pressure gauge 1007 measuring the air flow. Container 1003 has side wall 1012 through which temperature probe 1009 is located. Temperature probe 1009 is attached to temperature monitor 1008. Container 1003 has base 1011. The overall apparatus is indicated by reference numeral 1000. FIG. 10B sets forth a top view of the apparatus of FIG. 10A showing the use two tandem chambers 1003*a* and 1003*b*. Container 1003*a* is supplied with air flow through tube 1010*a* having pressure gauge 1007b in the air flow line. Container 1003b is supplied with air flow through tube 1010b with pressure gauge 1007a in its line. Air supply from location 1005 supplies air through line 1006a having pressure gauge 1007 in the line to measure air flow. The air flow is then split between line 1006b (for air flowing into container 1003a) and line 1006c (for air flowing to container 1003b). Temperature probe 1009a is used for container 1003a, and temperature probe 1009b is used for container 1003b. Temperature probe 1009b is attached to temperature monitor 1008b. Temperature probe 1009a is attached to temperature monitor 1008a. Container 1003a has opening 1004a at the top of same. Container 1003b has opening 1004b at the opening thereof. The overall apparatus having tandem containers for testing purposes is indicated by reference numeral 1000'.

The system shown in FIGS. 10A and 10B has as its primary purpose the simultaneous evaluation of an air freshener's performance for its hedonics, intensity, volatile content and weight loss as a function of time in a controlled environment of temperature and air mixing. The fragrance diffusion evaluation system is a midway station between a laboratory system that allows only analytical measurements and a full scale test of odor performance in a specially designed room that allows only sensory testing. The fragrance diffusion evaluation system provides a controlled environment that allows for both sensory and analytical measurements of a fragrance's performance at low cost.

The fragrance diffusion evaluation system, shown in FIGS. 10A and 10B, comprises a cylinder having a height of between about 50 and about 75 cm, a radius of between about 15 and 30 cm and a volume of between about 0.1 and 0.2 m$^3$. The interior is coated with aluminum foil to ensure that no fragrance absorbs into the walls. The air flow is provided by a tube through the side between about 3 and about 10 cm from the bottom extending to the center of the chamber. The temperature is continuously monitored by a gauge located between about 10 and about 30 cm from the bottom. An opening with a diameter of between 15 and 30 cm is at the top of the cylinder to allow air flow and odor intensity testing. The air flow is, on average, between about 900 and 1,000 ml per minute. This air flow replaces the whole volume of the fragrance diffusion evaluation system with fresh air every 2 hours. The air flow through the chamber is constant at a pressure of between about 0.5 and 2 psig.

Referring to FIG. 11A, the high speed rotation of the rotor blades 1106 within the precision machine mixing workhead exerts a powerful suction at location 1301 drawing liquid and solid materials 1104a into the rotor stator assembly 1100. The rotation is effected at access 3102. The output from the assembly is at location 1103. The workhead is indicated by reference numeral 1105. The overall device is indicated by reference numeral 1100. Referring to FIG. 11B, centrifugal force then drives materials 1104a towards the periphery of the workhead where they are subjected to a milling action in the precision machined clearance between the ends of the rotor blades and the inner wall of the stator.

Referring to FIG. 11C, stage 2 is followed by intense hydraulic shear as the materials 1104b are forced at high velocity out through the perforations in the stator 1106, then through the machine outlet and along the pipework 1103. At the same time, fresh materials are continually drawn into the workhead at 1101, maintaining the mixing and pumping cycle.

Referring to FIG. 11E, the single-stage homogenizing valve assembly, valve handle 1112a is used to adjust the flow inwardly at location 1113a and outwardly at location 1114a.

Referring to FIG. 11F, FIG. 11F sets forth a two-stage valve assembly for the homogenizer. Valve handle 1111 is used to adjust the first stage, and valve handle 1112 is used to adjust the second stage. The two-stage valve assembly contains seals 1117 and gaps 1115 and 1116. Reference numeral 1113 refers to the inlet to the two-stage valve assembly, and reference numeral 1114 refers to the outlet of the two-stage valve assembly. Reference numeral 1118 refers to the passageway between the inlet 1113 and the outlet 1114. The overall two-stage valve assembly is indicated by reference numeral 1110. Referring to FIG. 11D, FIG. 11D is the homogenizing equipment assembly. Mixer 1120 containing mixing shaft 1112 is a steam-heated feeder tank. The homogenizing equipment assembly is shown with the two-stage pressure adjustment system wherein the first-stage hand wheel is shown by reference numeral 1111, and the second-stage hand wheel is shown by reference numeral 1112. Pressure gauge 1122 is used to monitor the flow of fluid containing emulsion through a three-way bypass valve to cooling coils 1130 and recycle line 1114. Temperature gauge 1124 monitors the temperature of fluid flowing through line 1113 into the two-stage valve assembly which is attached to gear box 1123. The overall homogenizing equipment assembly is indicated by reference numeral 1160.

Referring to FIG. 11G, the rotor/stator mixing assembly, the initial blending operation is carried out in steam-heated feeder tank 1140 equipped with stirrer 1146. Fluid flows through line 1144 into rotor/stat-or mixing head 1142 controlled through control box 1141. The fluid then flows through line 1144 into three-way valve 1150. The fluid flows through cooling coils 1143 and 1143a. The fluid also flows past the three-way valve through recycle lines 1147 and 1147a back into feeder tank 1140. The rotor/stator mixing assembly is indicated by reference numeral 1190.

Referring to FIG. 12A, fragrance material from container 1201 flows through line 1203 controlled by valve 1202. Simultaneously, polymer and/or wax from container 1204 heated using heater 1205 flows through line 1207 controlled by valve 1206. Both fragrance material, polymer and/or wax flowing through lines 1203 and 1207 are blended in mixing tank 1208 which is also equipped with heater 1212. The thus-formed blend passes through line 1219 controlled by valve 1218 into blender 1220 simultaneously with product evolving from mixer 121.5. Thus, surfactant from container 1209 flows through line 1214 past control valve 1211, and simultaneously, water or aqueous mixture from container 1210, preheated using heater 1230, flows through line 1213 past control valve 1212 into mixing vessel 1215, also equipped with heater 1231. The surfactant/aqueous mixture is then passed through line 1217 past control valve 1216 into blender 1220 along with product from line 1219. Blender 1220 is a homogenizer and/or rotor/stator high shear mixer. Subsequent to the blending using the homogenizer and/or rotor/stator high shear mixer, product is passed through line 1223 past control valve 1222 into solid phase particle formation vessel 1225 equipped with cooling coils 1224, or apparatus components 1220 and 1225 can be combined into assembly 1190 as shown in FIG. 11G or assembly 1110 as shown in FIG. 11D. The resulting particulate slurry is then passed through line 1227 past control valve 1226 into a vessel for further utilization.

Referring to FIG. 12B, fragrance material from container 1250 is passed through line 1259 past control valve 1258 into mixer 1260 equipped with heater 1261. Simultaneously, polymer and/or wax from container 1251 equipped with heater 1252 is passed through control line 1256 past valve 1257 into mixer 1260. Simultaneously, surfactant from container 1253 is passed through line 1254 past valve 1255 into mixing vessel 1260. While mixing vessel 1260 is engaged in mixing fragrance material, polymer or wax and surfactant, aqueous composition heated through heater 1265 in container 1264 is then passed through line 1266 past control valve 1267 into blender 1268. Product mixed in container 1260 is passed through line 1262 past control valve 1263 into blender 1268. Blender 1268 can be a homogenizer and/or a rotor/stator high shear mixer. The resulting product is then passed through line 1269 past valve 1270 into solid phase particle formation vessel 1271 equipped with cooling coils 1272. In the alternative, apparatus components 1271 and 1268 can be combined into assemblies 1190, as shown in FIG. 11G, or 1110, as shown in FIG. 11D. The resulting product containing solid particulate particles having continuous surfaces is then passed through line 1273 past valve 1274 into container 1275 for utilization of the slurry.

The apparatus of FIG. 12A can be used in conjunction with electronic program controller 1300 as shown in FIG. 12C. Electronic program controller 1300 uses marketing input information from source 1299 via control line 1299c feeding into the electronic program controller 1300 and controlling the apparatus as illustrated in FIGS. 12A and 12C via control lines. Thus, the apparatus shown in schematic diagram in FIG. 12A is also shown in schematic form in FIG. 12C as associated with the electronic program controller (computer mechanism) via control lines.

More specifically, the control of fragrance material from container 1201 through line 1203 past control valve 1202 is controlled via control line 1202c. By the same token, flow of polymer and/or wax from container 1204 through line 1207 past valve 1206 is controlled through control line 1206c. The rate of heating and amount of heat energy into container 1204 using heater 1205 is controlled through control line 1205c. The mixing vessel 1208 mixing fragrance material, polymer and/or wax is heated through heater 1221 which is controlled through control line 1221c. The energy of mixing in mixing vessel 1208 is controlled through control line 1208c. Surfactant contained in container 1209 is fed through line 1214 past valve 1211 into mixing vessel 1215, and water or aqueous solution from container 1210 is heated using heater 1230 and flows past valve 1212 into mixing vessel 1215. The flow of the aqueous solution from container 1210 past valve 1212 is controlled through control line 1212c. The amount of heat energy into the aqueous solution in container 1210 is controlled through control line 1230c. The rate of flow of surfactant from container 1209 into mixing vessel 1215 is controlled through control line 1211c. The heat input into mixing vessel 1215 through heater 1231 is controlled through control line 1231c. The surfactant/aqueous solution mixture created in container 1215 is passed through line 1217 into blender 1220. The mixing energy in blender 1220 is controlled through control line 1220c. The flow of product from container 1208 into blending vessel 1220 (e.g., homogenizer) through line 1219 past valve 1218 is controlled through control line 1218c. The control of surfactant/aqueous composition from mixing vessel 1215 through line 1217 past valve 1216 into blender 1220 is controlled through control line 1216c. The flow of microemulsion from blender 1220 through line 1223 past control valve 1222 is controlled through control line 1222c, and the cooling energy using cooler 1224 for solid phase particle formation vessel 1225 is controlled through control line 1224c. The mixing energy in the solid phase particle formation vessel 1225 is controlled through control line 1225c. The flow from the solid phase particle formation vessel 1225 to utilization/storage/inventory vessel 1228 is controlled through control line 1226c, and marketing input information and output information are gathered through control line 1228c.

By the same token, the apparatus of FIG. 12B can be used in conjunction with electronic program controller 1302 which uses marketing input information from source 1301 via a control line feeding into the electronic program controller 1302 and controlling the apparatus as illustrated in FIG. 12B and FIG. 12D via control lines. Thus, the apparatus shown in schematic diagram in FIG. 12B is also shown in schematic form in FIG. 12D as associated with the electronic program controller (computer mechanism) via control lines.

More specifically, fragrance material from container 1250 passing through line 1259 past valve 1258 has its flow controlled through control line 1258c. The polymer and/or wax from container 1251 passing through line 1256 past control valve 1257 has its flow controlled through control line 1257c. Simultaneously, the heat input into container 1251 for heating the polymer and/or wax material using heater 1252 is controlled through control line 1252c. Simultaneously, surfactant from container 1253 flowing through line 1254 past valve 1255 has its flow controlled through control line 1255c. The surfactant, the polymer and/or wax and the fragrance material are mixed in mixing vessel 1260, and the mixing energy is controlled through control line 1260c and the heat input to the mixing vessel is controlled through control line 1261c. Aqueous composition is heated in container 1264 through heating element 1265 which is controlled through control line 1265c. The aqueous composition flow through line 1266 past valve 1267 is controlled through control line 1267c. The mixture of fragrance material, polymer and/or wax and surfactant in mixing vessel 1260 then flows through line 1262 past control valve 1263, and the flow of this mixture into blender (e.g., homogenizer) 1268 is controlled through control line 1263c. The flow of aqueous composition into the blender (e.g., homogenizer) from container 1264 through line 1266 past valve 1267 is controlled through control line 1267c. The homogenizing energy for blender 1268 is controlled through control line 1268c. The product emanating from blender 1268 through line 1269 past valve 1270 has its flow controlled through control line 1270c. The solid phase particle formation component of the apparatus of my invention 1271 is equipped with cooling coils 1272, controlled through control line 1272c. Operation of the solid phase particle formation component of the apparatus of my invention is controlled through control line 1271c. Flow from the solid phase particle formation vessel into the utilization of slurry, storage, inventory and marketing vessel 1275 past valve 1273 through line 1274 is controlled through control line 1273c. Marketing input and output to location 1275 is controlled through control line 1275c.

Referring to FIG. 13, the wax phase from location 3306 is admixed with fragrance oil and optional additives at location 1308 and fed into vessel 1309, simultaneously with water with emulsifier heated to 90° C. from location 1305 mixed with surfactant from location 1307 also flowing into vessel 1309. Fluid from vessel 1309 is passed through mixer or homogenizer 1310 and recycled back into vessel 1309 for a given period of time, e.g., one minute. The resulting fluid shown at location 1311 is then again passed through homogenizer 1312 and then quenched to solidify microparticles using a heat exchanger at location 1313.

Referring to FIG. 14, reference numeral 1403 refers to the data points for fragrance A-1. Reference numeral 1404 refers to the data points for fragrance A-2. Reference numeral 1405 refers to the data points for fragrance A-3. Reference numeral 1406 refers to the graph for data points 1403, 1404 and 1405. The Y axis is referred to using reference numeral 1401 for the {log$_{10}$[VP]} (of vapor pressure). The X axis is indicated by reference numeral 1402 and is for the accumulated sum (in weight percent) of the fragrance ingredients, fragrances A-1, A-2 and A-3. The graph 1406 is also described using the equation:

$$\{\log_{10}[VP]\} = (0.046)S^3 + (1.673)S^2 - (16.41)S - 4$$

wherein S represents the accumulated sum (weight percent) of the fragrance ingredients and {log$_{10}$[VP]} represents the log of the vapor pressure of each of the fragrance ingredients.

Referring to FIG. 15, the Y axis is indicated by reference numeral 1501 and represents weight loss (weight percent), normalized and shown by the symbol W. The X axis represents time and is indicated by reference numeral 1502 with time being shown by the symbol θ. Reference numeral 1503 indicates data points for the 50:50 mixture of high and low vapor pressure substances. Reference numeral 1504 represents data points for low vapor pressure substances (that is, <0.01 mm/Hg); and reference numeral 1505 represents data points for high vapor pressure substances (>0.1 mm/Hg). Reference numeral 1508 is the graph for weight loss versus time for the mixture of high and low vapor pressure substances (50:50) and is represented by the equation:

$$W = 94.583 - 0.29497\,\theta.$$

Reference numeral 1509 is the equation for weight loss versus time for low vapor pressure materials and is represented by the equation:

$$W = 98.679 - 0.09478\,\theta;$$

and reference numeral 1507 is the graph for weight loss versus time for high vapor pressure materials arid is represented by the equation:

$$W = 95.679 - 0.43843\,\theta.$$

With respect to FIG. 16 concerning the fragrance diffusion evaluation system, the Y axis concerning weight loss rate (weight percent per minute) is indicated by reference numeral 1601 and is shown by the term $$\left(\frac{dW}{d\theta}\right).$$

The X axis representing weight percent in the formula of fragrance A-3 is indicated by reference numeral 1602 and is also represented by the term W. Reference numeral 1603 represents the data points for the weight loss rate versus weight percent in the formula as measured by thermal gravimetric analysis (TGA). Reference numeral 3 604 represents the data points for the weight loss rate versus weight percent in the formula as measured by the fragrance diffusion evaluation system (FES) of FIGS. 10A and 10B. Reference numeral 1604a shows the standard deviation for the data points 1604. Reference numeral 1605 is the graph for weight loss rate versus weight percent in the formula as measured by the fragrance diffusion evaluation system and is represented by the equations:

$$\left(\frac{dW}{d\theta}\right) = 0.10675 + 0.003965\,W$$

and $$\mathrm{Ln}_e(0.10675 + 0.00395\,W) = \theta.$$

The reference numeral 1606 is for the graph of weight loss rate versus weight percent in the formula as measured by thermal gravimetric analysis and is represented by the equations:

$$\left(\frac{dW}{d\theta}\right) = 0.061929 + 0.00319\,W$$

and $$\mathrm{Ln}_e(0.061929 + 0.00319\,W) = \theta.$$

The thermogravimetric analysis (TGA) of the prior art is described in detail in Kroschwitz, "Polymers: Polymer Characterization and Analysis" published by John Wiley and Sons, 1990 at pages 837–848 (Chapter entitled: "Thermal Analysis") incorporated by reference herein.

With reference to FIG. 17, the Y axis is indicated by reference numeral 1701 and is for aroma chemical loading efficiency indicated by the symbol: ε. The X axis is indicated by reference numeral 1702 and is for the log$_{10}$P wherein P is the n-octanol-water partition coefficient for the materials benzyl alcohol, geraniol, farnesol and GALAXOLIDE®. Reference numeral 1703 is the data point for benzyl alcohol. Reference numeral 1704 is the data point for geraniol. Reference numeral 1704a shows the standard deviation for the data point for geraniol. Reference numeral 1705 is the data point for farnesol having the structure:

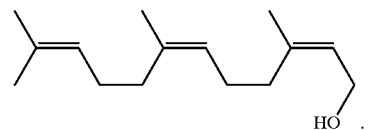

Reference numeral 1705a represents the standard deviation for the data point for farnesol. Reference numeral 1706 is the data point for GALAXOLIDE®. Reference numeral 1708 is the graph of aroma chemical loading efficiency versus log$_{10}$P wherein P is the n-octanol-water partition coefficient for the aroma chemicals The graph is also represented by the equation:

$$\varepsilon = 16.1433\{\log_{10}P\} - 5.922.$$

Aroma chemical loading efficiency is shown by the equation:

$$\varepsilon = \left(\frac{m_c}{m_T}\right) \times 100,$$

wherein the term: $m_c$ represents the mass of aroma chemicals encapsulated in the microparticles and the term: $m_T$ represents the total mass of the aroma chemical in the microparticle slurry.

The n-octanol/water partitioning coefficient of a perfume material indicated by the term "P" is the ratio between its equilibrium concentrations in n-octanol and in water. The perfume materials of my invention have an n-octanol/water partitioning coefficient P of between about 10 and about $10^8$. Since the partitioning coefficients of the perfume compositions of this invention have values between 10 and $10^8$, they are more conveniently given in the form of their logarithm to the base 10, $\log_{10}P$. Thus, the perfume materials useful in the practice of my invention have a $\log_{10}P$ of between about 1 and about 8 as indicated, supra.

The $\log_{10}P$ of many perfume ingredients have been reported; for example, the Pomona 92 database, available from Daylight Chemical Information Systems, Inc. (Daylight CIS), Irvine, Calif., contains many, along with citations to the original literature. However, the $\log_{10}P$ values are most conveniently calculated by the "CLOGP" program, also available from Daylight CIS. This program also lists experimental $\log_{10}P$ values when they are available in the Pomona 92 database. The "calculated $\log_{10}P$" is determined by the fragment approach of Hansch and Leo (*Comprehensive Medicinal Chemistry*, Volume 4, C. Hansch, P. G. Sammens, J. B. Taylor and C. A. Ramsden, Editors, page 295, Pergamon Press, 1990, incorporated by reference herein). The fragment approach is based on the the chemical structure of each component of the perfume material and takes into account the numbers and types of atoms, the atom connectivity and chemical bonding. The calculated $\log_{10}P$ values, which are the most reliable and widely used estimates for this physicochemical property, are preferably used instead of the experimental $\log_{10}P$ values in the selection of perfume materials useful in the practice of my invention.

FIG. 18A shows the rotor/stator mixer particle size distribution using 1.2% cetyl trimethyl ammonium chloride having the structure:

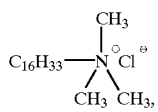

10% candelilla wax and 10% fragrance P-50448. The particle size distribution is set forth using reference numeral 1803. The X axis is represented by reference numeral 1802 which sets forth the particle diameter in microns. The Y axis sets forth the volume percent for each particular particle diameter and is represented by reference numeral 1801. The mean particle size of the particles is 2.4 microns and the distribution is as follows:

90% of particles are finer than: 3.8 microns;
75% of particles are finer than: 2.8 microns;
50% of particles are finer than: 2.0 microns;
25% of particles are finer than: 1.4 microns; and
10% of particles are finer than: 1.1 microns.

Referring to FIG. 18B, FIG. 18B shows a homogenized particle size distribution using a mixture containing 0.5% cetyl trimethyl ammonium chloride having the structure:

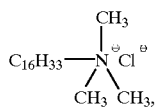

10% candelilla wax and 10% fragrance IB-X-016. The particle size distribution is as follows:

mean particle size: 0.74 microns;
90% of particles are finer than: 2.60 microns;
75% of particles are finer than: 0.70 microns;
70% of particles are finer than: 0.19 microns;
25% of particles are finer than: 0.14 microns; and
10% of particles are finer than: 0.12 microns.

The X axis is represented by reference numeral 1812 and indicates particle diameter in microns. The Y axis is indicated by reference numeral 1811 and indicates volume percent of particles of particular particle diameter. Reference numeral 1813 shows those particles having a particle diameter of from zero up to about 0.4 microns. Reference numeral 1814 shows those particles having a particle diameter of from about 0.4 up to about 3 micron. Reference numeral 1915 shows those particles having a particle diameter of from about 1.3 up to about 1.6 microns.

Referring to FIG. 19, the Y axis is indicated by reference numeral 1906 and the X axis indicating time in minutes is indicated by reference numeral 1905. Reference numeral 1901 represents data points for air flow in the second of two cylinders. Reference numeral 1902 indicates data points for air flow in the first of the two cylinders of FIG. 10B. Reference numeral 1903 shows the graph of time versus air flow for the first of the two cylinders in FIG. 10B. Reference numeral 1904 sets forth the graph of air flow versus time in the first of the two cylinders as set forth in FIG. 10B.

The following examples illustrate embodiments of this invention. All parts, percentages and proportions referred to herein and in the appended claims are by weight, unless otherwise indicated.

EXAMPLE A

| FRAGRANCE COMPOSITION The following fragrance composition is prepared for use in Examples I–IV, infra. | |
|---|---|
| Ingredients | Parts by Weight |
| hexyl cinnamic aldehyde | 15 |
| cis-3-hexenyl salicylate | 9 |
| ISO E SUPER ® (Trademark of International Flavors & Fragrances Inc. of New York, NY) having the structure: 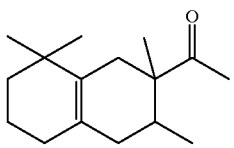 | 9 |
| LILIAL ® (Trademark of Givaudan, Inc. of Clifton, NJ) | 30 |
| β-ionone | 8 |
| γ-methyl ionone | 6 |
| citronellol | 25 |
| methyl nonyl acetaldehyde | 15 |
| allyl cyclohexyl propane | 5 |
| α-terpineol | 6 |
| borneol | 5 |
| β-phenyl ethyl alcohol | 25 |
| linalool | 9 |
| allyl amyl glycolate | 7 |
| linalyl acetate | 12 |
| dihydromyrcenol | 5 |
| isobornyl acetate | 20 |
| methyl chavicol | 5 |
| benzyl acetate | 9 |
| camphor | 15 |
| styralyl acetate | 5 |
| eucalyptus oil | 13 |
| cis-3-hexenyl acetate | 4 |

EXAMPLE I

Preparation of Microparticles using Silverson L4R Laboratory Mixer of FIG. 11G

The following procedure is used for the preparation of microparticles with the fragrance of Example A and candelilla wax using a Silverson L4R laboratory mixer as set forth in FIG. 11G and described, supra. The resulting formulation is:

84.7%, water;
10% candelilla wax;
5% fragrance of Example A; and
0.3% cetyl trimethyl ammonium chloride having the structure:

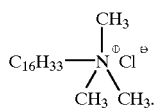

(1) 37.5 Grams of candelilla wax is placed in an oven at 125° C. and allowed to melt.

(2) 314.87 Grams of deionized water is placed into a steam jacket in a one gallon tank.

(3) The bottom of the tank is piped into the suction side of a Silverson in-line model L4R laboratory rotar/stator mixer. The discharge of the mixer was piped back into the tank to allow for recirculation.

(4) The mixer is turned on slowly and the water is drawn into the mixer and pumped back into the tank.

(5) 3.88 Grams of 29% cetyl trimethyl ammonium chloride solution in water is added to the water.

(6) Steam is turned on the jacket and the water/surfactant solution is heated to 90° C. A counter-rotating propeller mixer mounted in the tank ensures that the temperature of the water is homogeneous.

(7) Candelilla wax is removed from the oven and 18.75 grams of the fragrance of Example A is mixed into the wax by hand with a glass rod.

(8) The fragrance/wax mixture is poured into the tank. The counter-rotating propeller mixer speed is increased to disperse the wax/oil into the water and keep the emulsion homogeneous.

(9) The mixer is turned on maximum speed and is allowed to emulsify for one minute. The steam rate is adjusted to maintain a product temperature of 90° C.

(10) The mixer speed is reduced to a minimum and the three-way valve located on the mixer discharge is turned to divert the emulsion through a Parker dual heat transfer coil to solidify the emulsified wax and reduce the slurry temperature to ambient.

EXAMPLE II

Preparation of Microparticles using a Gaulin 15MR Homogenizer as set Forth in FIG. 11D and using the Homogenizer Pressure Adjustment Valve System of FIG. 11F The following procedure is for the preparation of microparticles with the fragrance of Example A in candelilla wax using a Gaulin 15MR homogenizer. The formulation is:

84.7% water;
10% candelilla wax;
5% fragrance of Example A; and
0.3% cetyl trimethyl ammonium chloride having the structure:

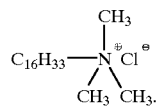

The steps are as follows:

(1) 75 Grams of candelilla wax is placed in an oven at 125° C. and allowed to melt.

(2) 629.74 Grams of deionized water is placed into a steam-jacketed one gallon tank.

(3) The bottom of the tank is piped into the suction side of a Gaulin 15MR-8TA laboratory homogenizer. The discharge of the homogenizer is piped back into the tank to allow for recirculation.

(4) The homogenizer is turned on with the secondary pressure set at 500 psig. The water is drawn into the homogenizer and pumped back into the tank.

(5) 7.78 Grams of a 29% active cetyl trimethyl ammonium chloride solution in water is added to the water (6) Steam is turned on the jacket and the water/surfactant solution is heated to 90° C. A counter-rotating propeller mixer mounted in the tank ensures that the temperature of the water is homogeneous.

(7) The candelilla wax is removed from the oven and 37.5 grams of the fragrance of Example A is mixed with the wax by hand with a glass rod.

(8) The fragrance/wax mixture is poured into the tank. The counter-rotating propeller mixer speed is increased to disperse the wax/oil into the water and keep the emulsion homogeneous.

(9) The second-stage pressure of the homogenizer is set at 6,000 psig and it is allowed to emulsify for one minute. Steam rate is adjusted to maintain 90° C. product temperature.

(10) A three-way mixing valve located on the homogenizer discharge is turned to divert the emulsion through a Parker dual heat transfer coil to solidify the emulsified wax and to reduce the slurry temperature to ambient.

The products produced in Examples I–IV, supra, give rise to aesthetically pleasing, long lasting fragrance effects when used in hair care preparation in accordance with the use of Examples:

U.S. Pat. No. 5,653,968 issued on Aug. 5, 1997, entitled "RINSE-OFF HAIR CARE COMPOSITIONS"; and U.S. Pat. No. 5,653,969 issued on Aug. 5, 1997, entitled "LOW RESIDUE HAIR CARE COMPOSITIONS".

EXAMPLE III

Use Of Shampoo/Conditioner 0.98 Grams of the slurry of Example I is admixed with 14 grams of a shampoo composition, as described in U.S. Pat. No. 5,658,868 issued on Aug. 19, 1997, incorporated by reference herein and containing:

5% (weight) 2-decenyl sulfonate;
15% (weight) sodium sulfosuccinate ester of n-decanolamide;
25% (weight) lauroamphocarboxyglycinate;
4% (weight) coconut amide;
3% (weight) glycol distearate;
4% (weight) aloe vera;

1% (weight) wheat germ oil; and

43% (weight) water.

The resultant mixture is applied to hair in a washing procedure. The hair is left to dry. After 24 hours, the dried hair thus washed has an aesthetically pleasing aroma having:

(1) a substantivity of 9 on a scale of 1–10;

(2) a quality of 10 on a scale of 1–10; and (3) an intensity of 3 on a scale of 1–10.

EXAMPLE IV

Use Of Fabric Softner 2.25 Grams of the slurry of Example II is admixed with 25 grams of a fabric softener composition as described in U.S. Pat. No. 5,656,585 issued on Aug. 12, 1997 and incorporated by reference herein.

100 Grams of unfragranced powder detergent as described in U.S. Pat. No. 5,658,875 issued on Aug. 19, 1997, the specification for which is incorporated by reference herein, and the above fabric softener mixture are then placed in a KENMORE® washing machine containing 14 hand towels (fabricated with cotton fabric, having the dimensions: 6"×6" and weighing 100 grams each).

After the washing procedure is carried out, the towels are line-dried for a period of 24 hours. 24 hours thereafter, each of the(thus-dried towels has an aesthetically pleasing aroma having:

(1) a substantivity of 9 on a scale of 1–10;

(2) a quality of 10 on a scale of 1–10; and (3) an intensity of 5 on a scale of 1–10.

What is claimed is:

1. Apparatus located in an X-Y-Z three-space for simultaneously testing the diffusivity, odor character and odor intensity of a fragrance material selected from the group consisting of one or more aroma chemicals and one or more fragrance compositions comprising:

(a) hollow vertically-disposed cylindrical container means consisting of one cylinder or two separate cylinders, each of which has:

(i) a central axis parallel to the Z axis;

(ii) an inner void;

(iii) a substantially circular non-interrupted base composed of a first solid nonporous substance located in a first X-Y plane, said base being substantially perpendicular to said Z axis and having all inner void side and an outside;

(iv) vertically surrounding said inner void and parallel to and substantially equidistant from said Z axis, a continuous cylindrical sidewall composed of a second solid nonporous substance having an inner void side and an outside, having a top circular rim located in a second X-Y plane, an upper midportion, a lower midportion and a bottom rim located in said first X-Y plane, said bottom rim being fixedly sealed along its entire circumference to the circumference of said base, said sidewall having a first orifice therethrough located in the lower midportion thereof in a third X-Y plane and a second orifice therethrough substantially diametrically opposed to said first orifice located in a fourth X-Y plane, said fourth X-Y plane being located between and substantially parallel to said third X-Y plane and said first X-Y plane, said sidewall otherwise being non-interrupted;

(v) a top substantially circular cover composed of a third solid nonporous substance and having an inner void side and an outside sealably attached along its entire outer circumference to the circumference of the top circular rim of said sidewall and located in said second X-Y plane, having a substantially circular top cover opening having an inner circumference, said inner circumference being substantially equidistant from said Z axis, said opening having a diameter of from about 20% up to about 40% of the outside diameter of the top cover;

(b) sealably mounted through said first orifice, a temperature probe having a temperature variation-sensitive end attached to support means, said temperature variation-sensitive end being located within said inner void, said support means seabably inserted through said first orifice and connected to temperature monitoring means outside said container means;

(c) sealably mounted through said second orifice, air flow means for supplying a stream of air into said inner void, said air flow means comprising a supply tube having an open end located within said inner void, being connected to said supply tube and located outside said container means, an air supply source; and (d) suspension means for suspending a test sample located within said inner void, said suspension means comprising a substantially flexible hanging support fixedly attached at two substantially diametrically opposed attachment locations located in substantially the same X-Y plane proximate said second X-Y plane, each being proximate the top rim of said sidewall and having attached thereto and suspended therefrom at a location substantially midway between said attachment locations, said test sample, initially having absorbed thereon said fragrance material.

2. The apparatus of claim 1 wherein (i) the temperature of the air supplied by the air supply means is controlled and (ii) the temperature probe has programmed feedback means connected to the air supply means.

3. The apparatus of claim 1 wherein each sidewall has a multiplicity of additional orifices at different locations, each of which has sealably mounted therethrough a temperature probe.

4. The apparatus of claim 3 wherein (i) the temperature of the air supplied by the air supply means is controlled and (ii) each of the temperature probes has programmed feedback means connected to the air supply means.

5. The apparatus of claim 1 wherein the measurement of the odor character and intensity is performed using an electronic aroma testing device.

6. A process for simultaneously testing the diffusivity, odor character and odor intensity of a fragrance material selected from the group consisting of one or more aroma chemicals and one or more fragrance compositions comprising the steps of:

(a) providing the apparatus of claim 1;

(b) suspending at least one test sample containing a fragrance material in the suspension means of said apparatus; and (c) engaging the air supply means and the temperature monitor means whereby when the air supply means is engaged to thereby causing air to flow through the air flow means and the temperature monitor is engaged, air at a fixed temperature T or a variable temperature $T(\theta)$ will flow at a fixed flow rate Q or a variable flow rate $Q(\theta)$ past each of said samples, each having an area A initially holding $G_0$ grams of fragrance materials in a concentration of $C_0$ gram-moles per liter for a period of time θ at the end of which time θ said sample will hold $G_1$ grams of fragrance material in a concentration $C_1$ gram-moles per liter during which time θ the odor character and intensity is capable of being measured and determined proximate the intersection of said Z axis with said second X-Y plane.

7. The process of claim 6 using apparatus wherein (i) the temperature of the air supplied by the air supply means is controlled and (ii) the temperature probe has programmed feedback means connected to the air supply means.

8. The process of claim 6 wherein in the apparatus provided, each sidewall has a multiplicity of additional orifices at different locations, each of which has sealably mounted therethrough a temperature probe.

9. The process of claim 8 wherein in the apparatus provided, (i) the temperature of the air supplied by the air supply means is controlled and (ii) the temperature probe has programmed feedback means connected to the air supply means.

10. The process of claim 6 wherein in the apparatus, the measurement of the odor character and intensity is performed using an electronic aroma testing device.

11. The process of claim 7 wherein in the apparatus provided, the measurement of the odor character and intensity is performed using an electronic aroma testing device.

12. The apparatus of claim 1 wherein the entirety of the inner void side of the base, the sidewall and the top cover is covered with an absorption-preventing substance to prevent absorption of said fragrance material into said base, said sidewall and said top cover.

13. The apparatus of claim 12 wherein the absorption-preventing substance is aluminum foil.

14. The apparatus of claim 1 wherein the container means consists of two separate cylinders.

15. The apparatus of claim 1 wherein the container means consists of one single cylinder.

16. The apparatus of claim 1 wherein the container means has:

(i) a height of in the range of from about 50 up to about 75 cm;

(ii) a radius in the range of from about 15 up to about 30 cm;

(iii) a volume in the range of from about 0.1 up to about 0.2 $m^3$;

(iv) a vertical distance of temperature probe to base of between about 10 and about 30 cm;

(v) a vertical distance of air flow means from base from about 3 up to about 10 cm; and (vi) a diameter of inner opening in top cover of from about 15 up to about 30 cm.

17. The process of claim 6 wherein the internal pressure in the inner void is maintained at from about 0.5 up to about 2 psig and the air flow rate is maintained in the range of from about 900 up to about 1,000 ml/minute.

18. The process of claim 6 wherein in the apparatus provided, the container means has:

(i) a height of container of from about 50 up to about 75 cm;

(ii) a radius of container means of from about 15 up to about 30 cm;

(iii) a volume of from about 0.1 up to about 0.2 $m^3$;

(iv) a vertical distance of temperature probe from base of from about 10 and about 30 cm;

(v) a vertical distance of air flow means from base from about 3 up to about 10 cm; and (vi) a diameter of inner opening in top cover of from about 15 up to about 30 cm.

19. The process of claim 18 wherein the internal pressure in the inner void is maintained at from about 0.5 up to about 2 psig and the air flow rate is maintained in the range of from about 900 up to about 1,000 ml/minute.

\* \* \* \* \*